(12) United States Patent
Fujiwara

(10) Patent No.: US 11,440,832 B2
(45) Date of Patent: Sep. 13, 2022

(54) GLASS FILLER AND METHOD FOR PRODUCING THE SAME

(71) Applicant: Nippon Sheet Glass Company, Limited, Tokyo (JP)

(72) Inventor: Kosuke Fujiwara, Mie (JP)

(73) Assignee: NIPPON SHEET GLASS COMPANY, LIMITED, Tokyo (JP)

( * ) Notice: Subject to any disclaimer, the term of this patent is extended or adjusted under 35 U.S.C. 154(b) by 407 days.

(21) Appl. No.: 16/343,334

(22) PCT Filed: Nov. 9, 2017

(86) PCT No.: PCT/JP2017/040459
§ 371 (c)(1),
(2) Date: Apr. 18, 2019

(87) PCT Pub. No.: WO2018/088488
PCT Pub. Date: May 17, 2018

(65) Prior Publication Data
US 2019/0315650 A1    Oct. 17, 2019

(30) Foreign Application Priority Data
Nov. 10, 2016   (JP) .............................. JP2016-219907

(51) Int. Cl.
*C03C 3/083*   (2006.01)
*C08K 7/14*   (2006.01)
(Continued)

(52) U.S. Cl.
CPC ............... *C03C 3/083* (2013.01); *A61K 8/25* (2013.01); *C03C 12/00* (2013.01); *C03C 13/00* (2013.01);
(Continued)

(58) Field of Classification Search
None
See application file for complete search history.

(56) References Cited

U.S. PATENT DOCUMENTS 2,921,342 A * 1/1960 Siefert .................... C03B 37/06
65/476
5,192,809 A * 3/1993 Jones ....................... C08J 11/10
521/49
(Continued)

FOREIGN PATENT DOCUMENTS

DE     29819347 U1 *  1/2000
JP     S63201041      8/1988
(Continued)

OTHER PUBLICATIONS

Extended European Search report issued in corresponding European Patent Application No. 17870365.8, dated Jun. 4, 2020, 8 pages.
(Continued)

*Primary Examiner* — Tae H Yoon
(74) *Attorney, Agent, or Firm* — Hamre, Schumann, Mueller & Larson, P.C.

(57) ABSTRACT

A glass filler of the present disclosure includes glass having a composition, the composition including iron oxide. For the content in mass % of the iron oxide in the composition, $0.005 \leq FeO \leq 0.30$ and $0.01 \leq T\text{-}Fe_2O_3 \leq 0.80$ ($T\text{-}Fe_2O_3$ represents total iron oxide calculated as $Fe_2O_3$) are satisfied. For the iron oxide in the composition, $Fe^{2+}/(Fe^{2+}+Fe^{3+})$, which represents the proportion by mass of $Fe^{2+}$ to total iron, is 0.15 or more and 1.00 or less. The glass filler of the present disclosure is a glass filler having a new composition including a coloring component, the glass filler having a high visible transmittance and a controlled color which can be, for example, within a range of colors different from those of conventional glass fillers that have a low visible transmittance.

18 Claims, 6 Drawing Sheets

(51) Int. Cl.

| | | |
|---|---|---|
| *C08K 3/40* | (2006.01) | |
| *C09D 5/02* | (2006.01) | |
| *A61K 8/26* | (2006.01) | |
| *C03C 12/00* | (2006.01) | |
| *C03C 13/00* | (2006.01) | |
| *C03C 17/10* | (2006.01) | |
| *C03C 17/25* | (2006.01) | |
| *C09D 11/322* | (2014.01) | |
| *A61K 8/25* | (2006.01) | |

(52) U.S. Cl.
CPC .............. *C03C 17/10* (2013.01); *C03C 17/25* (2013.01); *C08K 3/40* (2013.01); *C08K 7/14* (2013.01); *C09D 5/028* (2013.01); *C09D 11/322* (2013.01)

(56) References Cited

U.S. PATENT DOCUMENTS

| | | | |
|---|---|---|---|
| 5,346,864 A | 9/1994 | Maugendre et al. | |
| 7,562,538 B2* | 7/2009 | Landa | C03C 1/004 |
| | | | 501/56 |
| 9,237,994 B2* | 1/2016 | Fujiwara | A61K 8/29 |
| 9,658,437 B2* | 5/2017 | Goodwin | B32B 17/10119 |
| 2006/0048679 A1 | 3/2006 | Fujiwara et al. | |
| 2007/0042890 A1 | 2/2007 | Hemmings et al. | |
| 2007/0225424 A1 | 9/2007 | Schulz et al. | |
| 2009/0261307 A1 | 10/2009 | Hayakawa et al. | |
| 2011/0064951 A1 | 3/2011 | Fujiwara et al. | |
| 2011/0151261 A1* | 6/2011 | Fujiwara | A61K 8/26 |
| | | | 428/402 |
| 2012/0178611 A1 | 7/2012 | Ajiki et al. | |
| 2014/0326314 A1 | 11/2014 | Dogimont et al. | |

FOREIGN PATENT DOCUMENTS

| | | | |
|---|---|---|---|
| JP | H03122029 | | 5/1991 |
| JP | 403162456 A | * | 7/1991 |
| JP | 2003212594 | | 7/2003 |
| JP | 2007145700 | | 6/2007 |
| JP | 2007217192 | | 8/2007 |
| JP | 2008057745 | | 3/2008 |
| JP | 2011105587 | | 6/2011 |
| JP | 2011132109 | | 7/2011 |
| JP | 2011521869 | | 7/2011 |
| JP | 2014108897 | | 6/2014 |
| WO | 2004076372 | | 9/2004 |
| WO | 2009154064 | | 12/2009 |
| WO | 2010024283 | | 3/2010 |
| WO | 2012011232 | | 1/2012 |

OTHER PUBLICATIONS

International Search Report issued for International Patent Application No. PCT/JP2017/040459, dated Jan. 30, 2018, 5 pages including English translation.

* cited by examiner

GLASS FILLER AND METHOD FOR PRODUCING THE SAME

The present application is the national stage entry of international application PCT/JP2017/040459, filed Nov. 9, 2017, which claims the benefit of Japanese application JP2016-219907, filed Nov. 10, 2016.

TECHNICAL FIELD

The present invention relates to: a glass filler that can be used for incorporation in a resin composition, an paint, an ink composition, or a cosmetic and that can exhibit excellent color and gloss; and a method for producing the glass filler. The present invention further relates to a resin composition, a paint, an ink composition, and a cosmetic that contain the glass filler.

BACKGROUND ART

Dispersing a glass filler in a resin matrix can improve the strength or dimensional accuracy of a resin molded product. Known fillers for this purpose include glass fillers in the form of, for example, flakes, fibers, a powder, or beads. Glass fillers may be incorporated in paints to be applied as a lining material to the surface of a metal or concrete. Known fillers for this purpose include glass fillers in the form of, for example, flakes. As well as being used as reinforcing fillers, glass fillers may be incorporated, for example, as a pigment in various products such as resin compositions, paints, ink compositions, and cosmetics.

Coating the surface of a glass filler with a metal allows the glass filler to show a metallic color. Coating the surface of a glass filler with a metal oxide allows the glass filler to show an interference color due to interference of reflected light. Glass fillers (coated glass fillers) having a surface coating containing a metal or metal oxide as a main component can be used, for example, as bright pigments and are becoming widely used in applications where the color and gloss are important, such as in paints or cosmetics. Known fillers for incorporation as bright pigments in paints or cosmetics include glass fillers in the form of flakes.

In view of the purposes of glass fillers, the glass needs to have high chemical durability. Patent Literature 1 discloses glass flakes having C-glass composition formulated with a focus on chemical durability, glass flakes having E-glass composition developed for electrical appliances, and glass flakes having a common glass composition for glass sheets. Patent Literature 2 discloses glass flakes with improved heat resistance, chemical durability, and formability which are achieved by controlling the content of $SiO_2$, the content of $Al_2O_3$, and the total content of alkali metal oxides (($Li_2O$+$Na_2O$+$K_2O$). Patent Literature 3 discloses glass flakes having excellent visible light-absorbing ability, the glass flakes having a composition in which the content of total iron oxide (T-$Fe_2O_3$) calculated as $Fe_2O_3$ is more than 10 mass %. Patent Literature 4 discloses glass flakes having a composition in which the content of CuO is within a given range. Patent Literature 5 discloses glass flakes having a composition in which the content of CoO is within a given range.

CITATION LIST

Patent Literature

Patent Literature 1: JP 63(1988)-201041 A
Patent Literature 2: WO 2010/024283 A1
Patent Literature 3: WO 2004/076372 A1
Patent Literature 4: JP 2011-105587 A
Patent Literature 5: JP 2011-132109 A

SUMMARY OF INVENTION

Technical Problem

The glass flakes of Patent Literatures 1 and 2 are colorless, or even when they exhibit any color, the type of the color is not taken into consideration. That is, the composition of the glass includes no coloring component, or even when the composition includes any coloring component, the composition is not controlled in view of the color exhibited by the glass flakes.

The glass flakes of Patent Literature 3 have a low visible transmittance. For example, glass flakes disclosed as examples in this literature have a visible transmittance of 30% or less and have colors ranging from brown to black. The use of the glass flakes of Patent Literature 3 as a base material for producing coated glass flakes makes it possible to reduce the influence of the color of the glass flakes as the base material on the color exhibited by the coated glass flakes. However, the range of colors that the glass flakes themselves can have is considerably narrow, and providing a coating to the glass flakes may, depending on the application of the glass flakes, fail to produce a desired color.

An object of the present invention is to provide a glass filler having a new composition including a coloring component, the glass filler having a high visible transmittance and a controlled color which can be, for example, within a range of colors different from those of conventional glass fillers that have a low visible transmittance.

Solution to Problem

The present inventors have found that such a glass filler can be obtained by using iron oxide as a coloring component in a glass composition and by specifying, for the content of the iron oxide in the glass composition, the content of FeO and the content of T-$Fe_2O_3$ (T-$Fe_2O_3$ represents total iron oxide calculated as $Fe_2O_3$) and specifying, for the iron oxide in the glass composition, the ratio "$Fe^{2+}/(Fe^{2+}+Fe^{3+})$" representing the proportion by mass of $Fe^{2+}$ to total iron.

A glass filler of the present invention has a glass composition including iron oxide, wherein: for the content of the iron oxide in mass %, $0.005 \leq FeO \leq 0.30$ and $0.01 \leq T\text{-}Fe_2O_3 \leq 0.80$ are satisfied, wherein T-$Fe_2O_3$ denotes total iron oxide calculated as $Fe_2O_3$; and for the iron oxide in the composition, $Fe^{2+}/(Fe^{2+}+Fe^{3+})$ is 0.15 or more and 1.00 or less, wherein $Fe^{2+}/(Fe^{2+}+Fe^{3+})$ represents the proportion by mass of $Fe^{2+}$ to total iron.

A coated glass filler of the present invention includes the above glass filler of the present invention and a coating formed on a surface of the glass filler, wherein the coating contains a metal or a metal oxide as a main component.

The glass filler or coated glass filler can be used for addition to various compositions such as resin compositions, paints, ink compositions, and cosmetics. A resin composition, a paint, an ink composition, and a cosmetic of the present invention contain the above glass filler of the present invention or the above coated glass filler of the present invention.

A method for producing a glass filler according to the present invention is a method for producing the above glass filler or coated glass filler of the present invention, the method including controlling glass raw materials and/or an atmosphere where the glass filler is formed, thereby controlling, for the iron oxide in the glass composition, the content of FeO, the content of T-$Fe_2O_3$, and $Fe^{2+}/(Fe^{2+}+Fe^{3+})$ representing the proportion by mass of $Fe^{2+}$ to total iron to obtain the glass filler having a desired color.

Advantageous Effects of Invention

The present invention makes it possible to achieve a glass filler having a new composition including a coloring component, the glass filler having a high visible transmittance and a controlled color which can be, for example, within a range of colors different from those of conventional glass fillers that have a low visible transmittance.

DESCRIPTION OF EMBODIMENTS

Figure 1A:
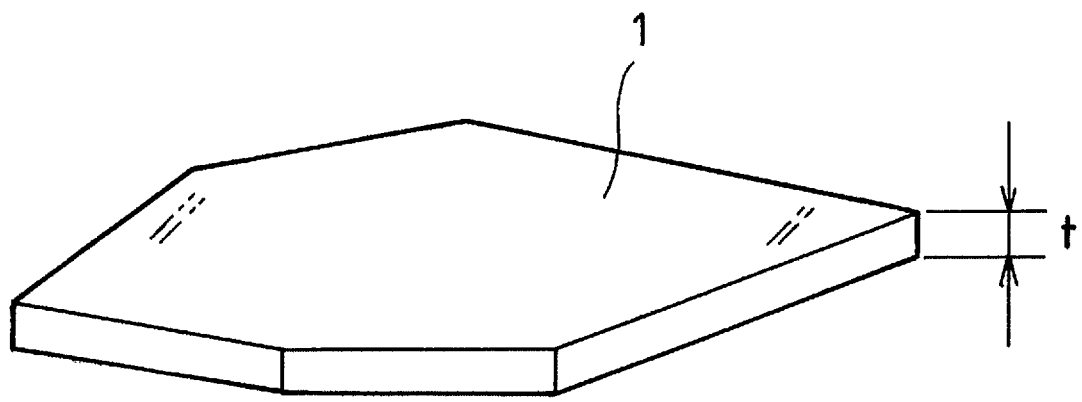
FIG. 1A is a perspective view schematically showing an exemplary glass flake which is a type of the glass filler of the present invention.

A first aspect of the present disclosure provides a glass filler including glass having a composition, the composition including iron oxide, wherein
for the content of the iron oxide in mass %, the following are satisfied:
0.005≤FeO≤0.30; and
0.01≤T-$Fe_2O_3$≤0.80, wherein T-$Fe_2O_3$ represents total iron oxide calculated as $Fe_2O_3$, and
for the iron oxide in the composition, $Fe^{2+}/(Fe^{2+}+Fe^{3+})$ is 0.15 or more and 1.00 or less, wherein $Fe^{2+}/(Fe^{2+}+Fe^{3+})$ represents the proportion by mass of $Fe^{2+}$ to total iron.

A second aspect of the present disclosure provides the glass filler according to the first aspect, wherein for the content of the iron oxide in mass %, the following is satisfied: 0.01≤T-$Fe_2O_3$<0.50.

A third aspect of the present disclosure provides the glass filler according to the first or second aspect, wherein the composition further includes $SiO_2$, $Al_2O_3$, and an alkaline-earth metal oxide.

A fourth aspect of the present disclosure provides the glass filler according to the first or second aspect, wherein the composition further includes the following components, in mass %:
60≤$SiO_2$≤75,
2≤$B_2O_3$≤8,
2≤$Al_2O_3$≤8,
5<$B_2O_3$+$Al_2O_3$≤15,
3≤CaO≤20,
6≤$Na_2O$≤20, and
9≤($Li_2O$+$Na_2O$+$K_2O$)≤20.

A fifth aspect of the present disclosure provides the glass filler according to the first or second aspect, wherein the composition further includes the following components, in mass %:
50≤$SiO_2$≤60,
2≤$B_2O_3$≤15,
10≤$Al_2O_3$≤20,
15≤CaO≤30, and
0≤($Li_2O$+$Na_2O$+$K_2O$)≤2.

A sixth aspect of the present disclosure provides the glass filler according to the first or second aspect, wherein the composition further includes the following components, in mass %:
57≤$SiO_2$≤65,
8≤$Al_2O_3$≤15,
1≤MgO≤5,
15≤CaO≤30, and
0≤($Li_2O$+$Na_2O$+$K_2O$)≤4.

A seventh aspect of the present disclosure provides the glass filler according to the first or second aspect, wherein the composition further includes the following components, in mass %:
65<$SiO_2$≤70,
5≤$Al_2O_3$≤15,
1≤MgO≤10,
10≤CaO≤25, and
0≤($Li_2O$+$Na_2O$+$K_2O$)≤4.

An eighth aspect of the present disclosure provides the glass filler according to the first or second aspect, wherein the composition further includes the following components, in mass %:
60≤$SiO_2$≤70,
5≤$Al_2O_3$≤15,
1≤MgO≤10,
10≤CaO≤25, and
4<($Li_2O$+$Na_2O$+$K_2O$)<9.

A ninth aspect of the present disclosure provides the glass filler according to the first or second aspect, wherein the composition further includes the following components, in mass %:
60≤$SiO_2$≤75,
5<$Al_2O_3$≤15,
5≤CaO≤20,
6≤$Na_2O$≤13, and
9≤($Li_2O$+$Na_2O$+$K_2O$)≤13.

A tenth aspect of the present disclosure provides the glass filler according to the first or second aspect, wherein the composition further includes the following components, in mass %:
60≤$SiO_2$≤75,
5<$Al_2O_3$≤15,
3≤CaO≤15,
9≤$Na_2O$≤20, and
13<($Li_2O$+$Na_2O$+$K_2O$)≤20.

An eleventh aspect of the present disclosure provides the glass filler according to the first or second aspect, wherein the composition further includes the following components, in mass %:
60≤$SiO_2$≤80,
5≤$B_2O_3$≤20,
5≤$Al_2O_3$≤15,
0.1≤(MgO+CaO)<1, and
9<$Na_2O$<13.

A twelfth aspect of the present disclosure provides the glass filler according to the first or second aspect, wherein the composition further includes the following components, in mass %:

50≤SiO$_2$≤75,
15≤Al$_2$O$_3$≤30,
5≤MgO≤25, and
0≤(Li$_2$O+Na$_2$O+K$_2$O)≤4.

A thirteenth aspect of the present disclosure provides the glass filler according to the first or second aspect, wherein the composition further includes the following components, in mass %:

60≤SiO$_2$≤75,
0.1≤(MgO+CaO)≤20,
9≤(Li$_2$O+Na$_2$O+K$_2$O)≤20, and
5≤ZrO$_2$≤20.

A fourteenth aspect of the present disclosure provides the glass filler according to any one of the first to thirteenth aspects, wherein a visible transmittance, as calculated for a thickness of 15 μm of the glass filler, is 87% or more.

A fifteenth aspect of the present disclosure provides the glass filler according to any one of the first to fourteenth aspects, wherein a light transmittance T$_{750nm}$ at a wavelength of 750 nm, as calculated for a thickness of 1 mm of the glass filler, is 71 to 91%.

A sixteenth aspect of the present disclosure provides the glass filler according to any one of the first to fifteenth aspects, wherein a light transmittance T$_{350nm}$ at a wavelength of 350 nm, as calculated for a thickness of 1 mm of the glass filler, is 5 to 84%.

A seventeenth aspect of the present disclosure provides the glass filler according to any one of the first to sixteenth aspects, wherein the glass filler is at least one selected from the group consisting of a glass flake, a chopped strand, a glass powder, and a glass bead.

An eighteenth aspect of the present disclosure provides the glass filler according to any one of the first to seventeenth aspects, wherein the glass filler is a glass flake.

A nineteenth aspect of the present disclosure provides a coated glass filler including the glass filler according to any one of the first to eighteenth aspects and a coating formed on a surface of the glass filler, wherein the coating contains a metal or a metal oxide as a main component.

A twentieth aspect of the present disclosure provides a resin composition including the glass filler according to any one of the first to eighteenth aspects or the coated glass filler according to the nineteenth aspect.

A twenty-first aspect of the present disclosure provides a paint including the glass filler according to any one of the first to eighteenth aspects or the coated glass filler according to the nineteenth aspect.

A twenty-second aspect of the present disclosure provides an ink composition including the glass filler according to any one of the first to eighteenth aspects or the coated glass filler according to the nineteenth aspect.

A twenty-third aspect of the present disclosure provides a cosmetic including the glass filler according to any one of the first to eighteenth aspects or the coated glass filler according to the nineteenth aspect.

A twenty-fourth aspect of the present disclosure provides a method for producing the glass filler according to any one of the first to eighteenth aspects or the coated glass filler according to the nineteenth aspect, the method including controlling glass raw materials and/or an atmosphere where the glass filler is formed, thereby controlling, for the iron oxide in the glass composition, the content of FeO, the content of T-Fe$_2$O$_3$, and Fe$^{2+}$/(Fe$^{2+}$+Fe$^{3+}$) representing the proportion by mass of Fe$^{2+}$ to total iron to obtain the glass filler having a desired color.

[Glass Filler]

The specific form of the glass filler of the present invention is not limited and, for example, is at least one selected from the group consisting of glass flakes, chopped strands, a glass powder, and glass beads. It should be noted that these specific forms are not strictly distinguished from each other. The glass filler of the present invention may include a combination of two or more different forms of glass fillers and may be, for example, a mixture of two or more different forms of glass fillers. The glass filler of the present invention can be produced by forming a melt of a glass composition into a desired shape.

Figure 1B:
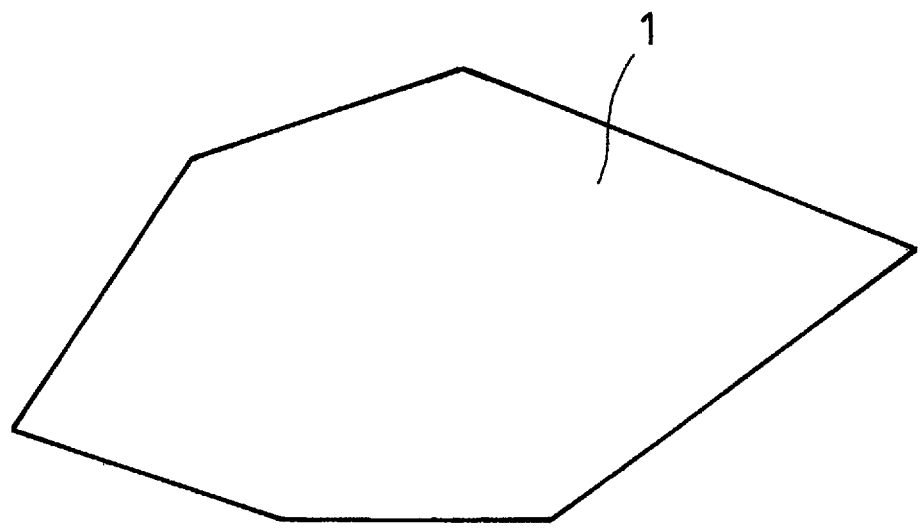
FIG. 1B is a plan view of the glass flake of FIG. 1A as seen from above.

In the present specification, "glass flakes" refer to platelet-like particles having an average thickness t of 0.1 μm or more and 15 μm or less, an average particle diameter a of 0.2 μm or more and 15000 μm or less, and an aspect ratio (average particle diameter a/average thickness t) of 2 or more and 1000 or less (see FIGS. 1A and 1B; FIGS. 1A and 1B illustrate an example of a glass flake 1 of the present invention).

The average thickness t of glass flakes can be determined as follows: at least 100 glass flakes are chosen, the thickness of each of the chosen glass flakes is measured with a microscope such as a scanning electron microscope (SEM), and the sum of the measured thickness values is divided by the number of the glass flakes subjected to the measurement. The average particle diameter a of glass flakes can be D50 determined by conducting particle size distribution analysis of at least 0.1 g of the glass flakes using a laser diffraction-scattering method (D50 refers to a particle diameter at a cumulative volume percentage of 50%).

Chopped strands used as the glass filler are glass fibers having dimensions with a fiber diameter of 1 to 50 μm and an aspect ratio (fiber length/fiber diameter) of 2 to 1000. The chopped strands may be circular or non-circular in cross-section and may have, for example, a flattened cross-section. The fiber diameter of a chopped strand is defined as the diameter of a circle having the same area as the cross-section of the strand.

A glass powder can be produced by pulverizing glass. A glass powder used as the glass filler has an average particle diameter of, for example, 1 to 500 μm. The particle diameter of a glass powder is defined as the diameter of a sphere having the same volume as the particles of the powder. The average particle diameter of a glass powder can be D50 determined by conducting particle size distribution analysis of at least 0.1 g of the glass powder using a laser diffraction-scattering method (D50 refers to a particle diameter at a cumulative volume percentage of 50%).

Glass beads can be produced by forming a glass composition into a spherical or nearly spherical shape. Glass beads used as the glass filler have a particle diameter of, for example, 1 to 500 μm. The particle diameter of a glass bead is defined as the diameter of a sphere having the same volume of the glass bead. The average particle diameter of glass beads can be D50 determined by conducting particle size distribution analysis of at least 0.1 g of the glass beads using a laser diffraction-scattering method (D50 refers to a particle diameter at a cumulative volume percentage of 50%).

<Composition>

The composition of the glass filler of the present invention will be described hereinafter.

(Iron Oxide) The composition (hereinafter referred to as "glass composition A") of the glass filler includes iron oxide.

In the glass composition A, the amount of the iron oxide, which is a coloring component absorbing visible light, is such that the content of T-$Fe_2O_3$ is 0.01 mass % or more and 0.80 mass % or less (T-$Fe_2O_3$ represents total iron oxide calculated as $Fe_2O_3$). If the content of T-$Fe_2O_3$ is less than 0.01 mass %, the effect of the iron oxide on coloring and color control of the glass filler cannot be obtained. If the content of T-$Fe_2O_3$ is more than 0.80 mass %, the visible transmittance of the glass filler decreases, and control of the color of the glass filler is difficult.

The lower limit of the content of T-$Fe_2O_3$ is preferably 0.02 mass % or more, more preferably 0.03 mass % or more, and most preferably 0.04 mass % or more. The upper limit of the content of T-$Fe_2O_3$ is preferably less than 0.50 mass %, more preferably 0.40 mass % or less, even more preferably 0.30 mass % or less, particularly preferably 0.25 mass % or less, and most preferably less than 0.20 mass %. The upper limit of the content of T-$Fe_2O_3$ may be 0.15 mass % or less. The content of T-$Fe_2O_3$ can be in a range defined by any combination of these upper and lower limits.

Additionally, for the iron oxide in the glass composition A, the content of FeO, which is a blue coloring component, and the content of $Fe_2O_3$, which is a yellow coloring component, are also controlled. Specifically, in the glass composition A, the content of FeO is 0.005 mass % or more and 0.30 mass % or less, and $Fe^{2+}/(Fe^{2+}+Fe^{3+})$ representing the proportion by mass of $Fe^{2+}$ to total iron (hereinafter, this proportion will be simply referred to as "$Fe^{2+}/(Fe^{2+}+Fe^{3+})$") is 0.15 or more and 1.00 or less. If the content of FeO is less than 0.005 mass %, control of the color of the glass filler is difficult. If the content of FeO is more than 0.30 mass %, control of the color of the glass filler is difficult, and the visible transmittance of the glass filler decreases. If $Fe^{2+}/(Fe^{2+}+Fe^{3+})$ is less than 0.15, control of the color of the glass filler is difficult.

The lower limit of the content of FeO is preferably 0.008 mass % or more and more preferably 0.01 mass % or more. The upper limit of the content of FeO is preferably 0.25 mass % or less, more preferably 0.20 mass % or less, even more preferably 0.15 mass % or less, particularly preferably 0.12 mass % or less, and most preferably 0.10 mass % or less. The content of FeO can be in a range defined by any combination of these upper and lower limits.

The lower limit of $Fe^{2+}/(Fe^{2+}+Fe^{3+})$ is preferably 0.20 or more, more preferably 0.25 or more, even more preferably 0.30 or more, particularly preferably 0.35 or more, and most preferably 0.40 or more. The upper limit of $Fe^{2+}/(Fe^{2+}+Fe^{3+})$ is preferably 0.90 or less, more preferably 0.85 or less, even more preferably 0.80 or less, particularly preferably 0.75 or less, and most preferably 0.70 or less. The upper limit of $Fe^{2+}/(Fe^{2+}+Fe^{3+})$ may be 0.60 or less. $Fe^{2+}/(Fe^{2+}+Fe^{3+})$ can be in a range defined by any combination of these upper and lower limits.

The content of FeO, the content of T-$Fe_2O_3$, and $Fe^{2+}/(Fe^{2+}+Fe^{3+})$ in a glass composition or a formed glass product such as a glass filler can be determined according to a total iron content determination method (o-phenanthroline spectrophotometric method) as specified in JIS R 3101:1995 and JIS R 3105:1995. Specifically, the content of T-$Fe_2O_3$ can be determined by the determination method. The content of FeO can be determined by a method similar to the determination method, except that an ascorbic acid solution is not added to a sample solution, in particular a sample solution (A) as specified in JIS R 3101 and JIS R 3105 (this means that $Fe^{3+}$ in the sample solution is not reduced into $Fe^{2+}$), and that a curve representing the relationship between the $Fe^{2+}$ concentration and the absorbance at a wavelength of 510 nm is used as a calibration curve. The calibration curve is made beforehand according to "Preparation of Calibration Curve" in 8.2.4 of JIS R 3101 and JIS R 3105 using a standard solution which is prepared by adding an adequate amount of ascorbic acid solution (concentration: 50 g/L) to a standard ferric oxide solution as specified in JIS R 3101 and JIS R 3105. $Fe^{2+}/(Fe^{2+}+Fe^{3+})$ can be calculated from the content of FeO and the content of T-$Fe_2O_3$ which have been determined as above.

Such control of the content and oxidation-reduction state of the iron oxide can be accomplished, for example, by controlling glass raw materials when mixing the glass raw materials to form molten glass, in particular by controlling the types and amounts of the glass raw materials. In a more specific example, the control of the content and oxidation-reduction state of the iron oxide can be accomplished by adding a reductant and/or an oxidant when mixing glass raw materials to form molten glass. In this example, the content of T-$Fe_2O_3$, the content of FeO, and $Fe^{2+}/(Fe^{2+}+Fe^{3+})$ in the glass composition can be controlled by selecting and controlling the type and amount of the raw material to be converted to iron oxide in the glass and by controlling the type and amount of the reductant and/or oxidant to be added. The reductant is, for example, a carbon-based reductant such as carbon or may be sugar or tin oxide. The oxidant is, for example, a sulfuric acid salt such as sodium sulfate or calcium sulfate or a nitric acid salt such as sodium nitrate or potassium nitrate.

In another specific example, the control of the oxidation-reduction state of the iron oxide can be accomplished by controlling a formation temperature and formation atmosphere where the glass filler is formed. The formation temperature is, for example, the temperature of the atmosphere with which molten raw glass 11 shown in FIGS. 2 and 3 referenced below is in contact until it is finally processed into a glass filler. The formation atmosphere is, for example, the atmosphere with which the molten raw glass 11 shown in FIGS. 2 and 3 referenced below is in contact until it is finally processed into a glass filler. An atmosphere that allows iron in the molten raw glass to undergo oxidation is an oxidizing atmosphere, an example of which is an atmosphere containing an oxidizing gas such as air or oxygen gas. An atmosphere that allows iron in the molten raw glass to undergo reduction is a reducing atmosphere or an inert atmosphere. The reducing atmosphere is, for example, an atmosphere of a reducing gas such as a mixed gas containing hydrogen, and the inert atmosphere is, for example, an atmosphere of an inert gas such as nitrogen gas, helium gas, or argon gas. A reductant and/or an oxidant may be used in conjunction with control of the formation atmosphere where the glass filler is formed.

The control concerning the iron oxide in the glass composition A can result in a glass filler having a composition including a coloring component, the glass filler having a high visible transmittance and a controlled color.

The color of the glass filler can be evaluated by light transmittances T of the glass filler at specific different wavelengths. Light transmittance $T_{750nm}$ at a wavelength of 750 nm may be, for example, 71 to 91%. When $T_{750nm}$ is in this range, the flexibility in controlling the color of the glass filler can be increased while a high visible transmittance is ensured. If $T_{750nm}$ is less than 71%, the transmittance in the long-wavelength visible region decreases, and accordingly the color of the glass filler tends to become bluish. The lower limit of $T_{750nm}$ may be 73% or more, 75% or more, 77% or more, 79% or more, 80% or more, or even 81% or more, depending on the composition of the glass forming the glass filler. The upper limit of $T_{750nm}$ may be 90% or less, depending on the composition of the glass forming the glass filler. Glass flakes disclosed in Patent Literature 3 have a composition including iron oxide; however, this glass product cannot have $T_{750nm}$ within the above range. $T_{750nm}$ of this glass product is much lower than 71% or cannot be measured because of low visible transmittance.

Light transmittance $T_{350nm}$ at a wavelength of 350 nm may be, for example, 5 to 84%. When $T_{350nm}$ is in this range, it is possible to further increase the flexibility in controlling the color of glass to a color that is desired for incorporation in resin compositions, paints, ink compositions, or cosmetics and that cannot be exhibited by conventional glass fillers with low visible transmittance. If $T_{350nm}$ is less than 5%, the transmittance in the short-wavelength visible region decreases, and accordingly the color of the glass filler tends to become yellowish. The lower limit of $T_{350nm}$ may be 10% or more, 15% or more, 20% or more, 23% or more, 27% or more, 30% or more, 35% or more, 40% or more, 45% or more, or even 50% or more, depending on the composition of the glass forming the glass filler. The upper limit of $T_{350nm}$ may be 83% or less, depending on the composition of the glass forming the glass filler. Glass flakes disclosed in Patent Literature 3 have a composition including iron oxide; however, this glass material cannot have $T_{350nm}$ within the above range. $T_{350nm}$ of this glass material is much lower than 5%.

The light transmittance of the glass filler can be a value determined for the glass filler with a thickness of 1 mm. When the thickness of the glass filler to be measured is less than 1 mm, a light transmittance value determined for a 1-mm-thick glass sheet having the same composition as the glass filler can be employed as the light transmittance of the glass filler.

Specific examples of the glass filler's color achieved by the above-mentioned control concerning the iron oxide in the glass composition A include blue, bluish green, green, yellowish green, and yellow. The color can be transparent thanks to the high visible transmittance.

(Components Other than Iron Oxide)

For the glass composition A of the glass filler, the types and contents of components other than iron oxide can be arbitrarily chosen. It should be understood, however, that in order for a material to be glass, the glass composition A includes a component (network former) forming glass skeleton. The network former includes, for example, at least one selected from $SiO_2$, $B_2O_3$, and $Al_2O_3$. The glass composition A may include at least one selected from $SiO_2$, $B_2O_3$, and $Al_2O_3$ and may include at least one selected from $SiO_2$ and $Al_2O_3$.

In an example, the glass composition A further includes $SiO_2$ and $Al_2O_3$. The content of $SiO_2$ in this glass composition A is, for example, 40 mass % or more and 80 mass % or less and may be 45 mass % or more and 75 mass % or less. The content of $Al_2O_3$ is, for example, 0.1 mass % or more and 35 mass % or less and may be 2 mass % or more and 30 mass % or less.

The glass composition A may include $B_2O_3$. The content of $B_2O_3$ in the glass composition A can be chosen depending on the application of the glass filler. The content of $B_2O_3$ is, for example, 0 mass % or more and 45 mass % or less and may be 0.1 mass % or more and 40 mass % or less. The glass composition A may be a composition substantially free of $B_2O_3$.

The glass composition A may include an alkaline-earth metal oxide. The alkaline-earth metal oxide (RO) includes at least one selected from MgO, CaO, SrO, and BaO and may include at least one selected from MgO, CaO, and SrO or at least one selected from MgO and CaO. The content of the alkaline-earth metal oxide in the glass composition A can be chosen depending on the application of the glass filler. The content of RO is, for example, 0 mass % or more and 45 mass % or less and may be 0.1 mass % or more and 40 mass % or less.

In an example, the glass composition A further includes $SiO_2$, $Al_2O_3$, and an alkaline-earth metal oxide.

The glass composition A may include an alkali metal oxide. The alkali metal oxide ($R'_2O$) includes at least one selected from $Li_2O$, $Na_2O$, and $K_2O$. The content of the alkali metal oxide in the glass composition A can be chosen depending on the application of the glass filler. The content of the alkali metal oxide is, for example, 0 mass % or more and 25 mass % or less and may be 0.1 mass % or more and 20 mass % or less. The glass composition A may be an alkali-free glass composition substantially free of any alkali metal oxide.

That is, the glass composition A may further include the following components, in mass %:
$40 \leq SiO_2 \leq 80$,
$0 \leq B_2O_3 \leq 45$,
$0.1 \leq Al_2O_3 \leq 35$,
$0 \leq RO \leq 45$, and
$0 \leq R'_2O \leq 25$.

The glass composition A may consist essentially of the above components or may consist of the above components. In these cases, the contents of the components in the glass composition A and the balance between the components may be such that the contents of the components are within the above numerical ranges including the preferred ranges.

(Specific Examples of Glass Composition A)

(Composition A-1)

In a specific example, the glass composition A further includes the following components, in mass %:
$60 \leq SiO_2 \leq 75$,
$2 \leq B_2O_3 \leq 8$,
$2 \leq Al_2O_3 \leq 8$,
$5 < B_2O_3 + Al_2O_3 \leq 15$,
$3 \leq CaO \leq 20$,
$6 \leq Na_2O \leq 20$, and
$9 \leq (Li_2O + Na_2O + K_2O) \leq 20$ (composition A-1).

The glass composition A-1 corresponds to C-glass composition. The contents of the components in the glass composition A-1 are limited within a range in the same manner as the contents of the components in the C-glass composition. A glass filler having the glass composition A-1 exhibits high chemical durability attributed to the high proportion of the components (network formers) forming the skeleton of the glass and has excellent mechanical properties, as does a glass filler having the C-glass composition. A glass filler having the glass composition A-1 also exhibits excellent mechanical and chemical stability in a product, such as a resin composition, which contains the glass filler.

Hereinafter, the components in the glass composition A-1 will be described.

($SiO_2$)

Silicon dioxide ($SiO_2$) is a component involved in formation of the skeleton of the glass and is a main component (whose content is highest) in the composition A-1. In the composition A-1, $SiO_2$ is a component responsible for adjusting the devitrification temperature and viscosity during glass forming and for improving the acid resistance.

When the content of $SiO_2$ in the composition A-1 is 60 mass % or more and 75 mass % or less, the devitrification temperature of the glass is prevented from being so high as to make production of the glass filler difficult, and the acid resistance of the glass is increased. When the content of $SiO_2$ is in this range, the melting point of the glass cannot be excessively high, and the uniformity of melting of raw materials is improved. The lower limit of the content of $SiO_2$ may be 63 mass % or more, and may be more than 64 mass % or even more than 65 mass %. The upper limit of the content of $SiO_2$ may be 72 mass % or less and may be 70 mass % or less. The upper and lower limits of the content can be arbitrarily combined, and the same applies to other components described hereinafter (including components contained in other specific examples of the glass composition A).

($B_2O_3$)

Diboron trioxide ($B_2O_3$) is a component involved in formation of the skeleton of the glass. $B_2O_3$ is a component responsible also for adjusting the devitrification temperature and viscosity during glass forming. However, the inclusion of excess $B_2O_3$ reduces the acid resistance of the glass. When the content of $B_2O_3$ in the composition A-1 is 2 mass % or more and 8 mass % or less, the devitrification temperature of the glass is prevented from being so high as to make production of the glass filler difficult, and the acid resistance of the glass is increased. Additionally, the melting point of the glass cannot be excessively high, and the uniformity of melting of raw materials is improved. The lower limit of the content of $B_2O_3$ may be 3 mass % or more and may be 4 mass % or more. The upper limit of the content of $B_2O_3$ may be 7 mass % or less and may be 6 mass % or less, or even 5 mass % or less.

($Al_2O_3$)

Aluminum oxide ($Al_2O_3$) is a component involved in formation of the skeleton of the glass. $Al_2O_3$ is a component responsible also for adjusting the devitrification temperature and viscosity during glass forming and for improving the water resistance of the glass. However, the inclusion of excess $Al_2O_3$ reduces the acid resistance of the glass. When the content of $Al_2O_3$ in the composition A-1 is 2 mass % or more and 8 mass % or less, the devitrification temperature of the glass is prevented from being so high as to make production of the glass filler difficult, and the acid resistance of the glass is increased. Additionally, the melting point of the glass cannot be excessively high, and the uniformity of melting of raw materials is improved. The lower limit of the content of $Al_2O_3$ may be 3 mass % or more and may be 3.5 mass % or more, or even 4 mass % or more. The upper limit of the content of $Al_2O_3$ may be 7 mass % or less and may be 6 mass % or less, or even 5 mass % or less.

($B_2O_3+Al_2O_3$)

For the composition A-1, ($B_2O_3+Al_2O_3$) representing the sum of the contents of $B_2O_3$ and $Al_2O_3$ is a key parameter when the ease of formation and the acid resistance of the glass filler are given priority. When ($B_2O_3+Al_2O_3$) in the composition A-1 is more than 5 mass % and 15 mass % or less, the devitrification temperature of the glass is prevented from being so high as to make production of the glass filler difficult, and the acid resistance of the glass is increased. Additionally, the melting point of the glass cannot be excessively high, and the uniformity of melting of raw materials is improved. The lower limit of ($B_2O_3+Al_2O_3$) may be 6 mass % or more and may be 7 mass % or more, or even 8 mass % or more. The upper limit of ($B_2O_3+Al_2O_3$) may be 14 mass % or less and may be 13 mass % or less, less than 12 mass %, 11 mass % or less, or even 10 mass % or less.

(MgO)

The composition A-1 may further include magnesium oxide (MgO). MgO included in the composition A-1 is a component responsible for adjusting the devitrification temperature and viscosity during glass forming. Thus, the lower limit of the content of MgO in the composition A-1 may be 0.1 mass % or more and may be 1 mass % or more, or even 2 mass % or more. The upper limit of the content of MgO may be 10 mass % or less and may be 8 mass % or less, 6 mass % or less, 5 mass % or less, or even 4 mass % or less.

(CaO)

In the composition A-1, calcium oxide (CaO) is a component responsible for adjusting the devitrification temperature and viscosity during glass forming.

When the content of CaO in the composition A-1 is 3 mass % or more and 20 mass % or less, excessive increase in the devitrification temperature of the glass can be prevented, and the devitrification temperature and the viscosity at melting of the glass can be controlled within ranges suitable for production of the glass filler. The lower limit of the content of CaO may be 4 mass % or more. The upper limit of the content of CaO may be 15 mass % or less and may be 11 mass % or less, or even 9 mass % or less.

(SrO)

The composition A-1 may further include strontium oxide (SrO). SrO included in the composition A-1 is a component responsible for adjusting the devitrification temperature and viscosity during glass forming. However, the inclusion of excess SrO reduces the acid resistance of the glass. Thus, the upper limit of the content of SrO in the composition A-1 may be 10 mass % or less and may be 5 mass % or less, 2 mass % or less, or even less than 0.1 mass %. The composition A-1 may be substantially free of SrO.

(BaO)

The composition A-1 may further include barium oxide (BaO). BaO included in the composition A-1 is a component responsible for adjusting the devitrification temperature and viscosity during glass forming. However, the inclusion of excess BaO reduces the acid resistance of the glass. Thus, the upper limit of the content of BaO in the composition A-1 may be 10 mass % or less and may be 5 mass % or less, 2 mass % or less, or even less than 0.1 mass %. The composition A-1 may be substantially free of BaO.

(ZnO)

The composition A-1 may further include zinc oxide (ZnO). ZnO included in the composition A-1 is a component responsible for adjusting the devitrification temperature and viscosity during glass forming. However, ZnO is prone to evaporation and can be lost into the atmosphere during melting, and the inclusion of excess ZnO therefore increases the evaporation-induced variation in glass component proportions, making difficult control of the glass composition. The lower limit of the content of ZnO in the composition A-1 may be 0.1 mass % or more and may be 1 mass % or more. The upper limit of the content of ZnO may be 10 mass % or less and may be 8 mass % or less, 6 mass % or less, or even 5 mass % or less.

($Li_2O$, $Na_2O$, and $K_2O$)

In the composition A-1, alkali metal oxides ($Li_2O$, $Na_2O$, and $K_2O$) are components are responsible for adjusting the devitrification temperature and viscosity during glass forming with retention of the heat resistance of the glass.

The composition A-1 may further include lithium oxide ($Li_2O$). The lower limit of the content of $Li_2O$ in the composition A-1 may be 0.1 mass % or more and may be 0.5 mass % or more. The upper limit of the content of $Li_2O$ may be 5 mass % or less and may be less than 2 mass %, or even less than 1 mass %.

When the content of sodium oxide ($Na_2O$) in the composition A-1 is 6 mass % or more and 20 mass % or less, excessive increase in the devitrification temperature of the glass can be prevented, and the devitrification temperature and viscosity of molten glass can be controlled within ranges suitable for production of the glass filler. Additionally, the increase in the melting point of the glass can be limited to achieve more uniform melting of glass raw materials, and at the same time excessive decrease in the glass transition temperature can be avoided to ensure high heat resistance of the glass Further, with the content of $Na_2O$ falling within in the above range, the chemical durability of the glass can also be improved. The lower limit of the content of $Na_2O$ may be 7 mass % or more and may be 8 mass % or more, 9 mass % or more, 9.5 mass % or more, or even 10 mass % or more. The upper limit of the content of $Na_2O$ may be 17 mass % or less and may be 15 mass % or less, 13 mass % or less, or even 12 mass % or less.

The composition A-1 may further include potassium oxide ($K_2O$). The lower limit of the content of $K_2O$ in the composition A-1 may be 0.1 mass % or more and may be 0.5 mass % or more. The upper limit of the content of $K_2O$ in the composition A-1 may be 5 mass % or less and may be 3 mass % or less, less than 2 mass %, or even 1 mass % or less.

When ($Li_2O+Na_2O+K_2O$) representing the total content of alkali metal oxides is 9 mass % or more and 20 mass % or less in the composition A-1, excessive increase in the devitrification temperature of the glass can be prevented, and the devitrification temperature and viscosity of molten glass can be controlled within ranges suitable for production of the glass filler. Additionally, the increase in the melting point of the glass can be limited to achieve more uniform melting of glass raw materials, and at the same time excessive decrease in the glass transition temperature can be avoided to ensure high heat resistance of the glass The lower limit of ($Li_2O+Na_2O+K_2O$) may be 9.5 mass % or more and may be 10 mass % or more, 10.5 mass % or more, or 11 mass % or more. The upper limit of ($Li_2O+Na_2O+K_2O$) may be 18 mass % or less and may be 16 mass % or less, 15 mass % or less, 14 mass % or less, 13 mass % or less, or even 12 mass % or less.

($TiO_2$)

The glass composition A-1 may further include titanium oxide ($TiO_2$). $TiO_2$ included in the composition A-1 is a component responsible for improving the meltability and chemical durability of the glass and improving the ultraviolet absorption property of the glass. The upper limit of the content of $TiO_2$ in the composition A-1 may be 5 mass % or less and may be less than 2 mass %, 1 mass % or less, 0.5 mass % or less, or even 0.2 mass % or less. When the content of $TiO_2$ is below such an upper limit, the devitrification temperature of molten glass can be prevented from being so high due to the inclusion of $TiO_2$ that the production of the glass filler is affected. The composition A-1 may be substantially free of $TiO_2$.

($ZrO_2$)

The glass composition A-1 may further include zirconium oxide ($ZrO_2$). $ZrO_2$ included in the composition A-1 is a component responsible for adjusting the devitrification temperature and viscosity during glass forming. The upper limit of the content of $ZrO_2$ in the composition A-1 may be 5 mass % or less and may be 2 mass % or less, 1 mass % or less, or even less than 0.1 mass %. When the content of $ZrO_2$ is below such an upper limit, the devitrification temperature of molten glass can be prevented from being so high due to the inclusion of $ZrO_2$ that the production of the glass filler is affected. The composition A-1 may be substantially free of $ZrO_2$.

(Composition A-2)

In another specific example of the glass composition A, the composition further includes the following components, in mass %:

$50 \leq SiO_2 \leq 60$,
$2 \leq B_2O_3 \leq 15$,
$10 \leq Al_2O_3 \leq 20$,
$15 \leq CaO \leq 30$, and
$0 \leq (Li_2O+Na_2O+K_2O) \leq 2$ (composition A-2).

The glass composition A-2 corresponds to E-glass composition. The contents of the components in the glass composition A-2 are limited within a range in the same manner as the contents of the components in the E-glass composition. A glass filler having the glass composition A-2 exhibits high electrical insulation performance and chemical durability attributed to the low content of alkali metal oxides and has good mechanical properties, as does a glass filler having the E-glass composition. A glass filler having the glass composition A-2 exhibits high mechanical and chemical stability also in a product, such as a resin composition, which contains the glass filler.

The components in the glass composition A-2 will be described hereinafter.

($SiO_2$)

$SiO_2$ is a component involved in formation of the skeleton of the glass and is a main component (whose content is highest) in the composition A-2. In the composition A-2, $SiO_2$ is a component responsible for adjusting the devitrification temperature and viscosity during glass forming and for improving the water resistance. When the content of $SiO_2$ in the composition A-2 is 50 mass % or more and 60 mass % or less, the devitrification temperature of the glass is prevented from being so high as to make production of the glass filler difficult, and the water resistance of the glass is increased. When the content of $SiO_2$ is in this range, the melting point of the glass cannot be excessively high, and the uniformity of melting of raw materials is improved. The lower limit of the content of $SiO_2$ may be 51 mass % or more and may be 52 mass % or more, 53 mass % or more, or even 54 mass % or more. The upper limit of the content of $SiO_2$ may be 58 mass % or less, 57 mass % or less, or even 56 mass % or less.

($B_2O_3$)

$B_2O_3$ is a component involved in formation of the skeleton of the glass. $B_2O_3$ is a component responsible also for adjusting the devitrification temperature and viscosity during glass forming. However, the inclusion of excess $B_2O_3$ reduces the water resistance of the glass. When the content of $B_2O_3$ in the composition A-2 is 2 mass % or more and 15 mass % or less, the devitrification temperature of the glass is prevented from being so high as to make production of the glass filler difficult, and the water resistance of the glass is increased. Additionally, the melting point of the glass cannot be excessively high, and the uniformity of melting of raw materials is improved. The lower limit of the content of $B_2O_3$ may be 3 mass % or more, and may be 4 mass % or more, or even 5 mass % or more. The upper limit of the content of $B_2O_3$ may be 13 mass % or less and may be 10 mass % or less, 8 mass % or less, 7 mass % or less, or even 6 mass % or less.

($Al_2O_3$)

$Al_2O_3$ is a component involved in formation of the skeleton of the glass. $Al_2O_3$ is a component responsible also for adjusting the devitrification temperature and viscosity during glass forming and for improving the water resistance of the glass. When the content of $Al_2O_3$ in the composition A-2 is 10 mass % or more and 20 mass % or less, the devitrification temperature of the glass is prevented from being so high as to make production of the glass filler difficult, and the water resistance of the glass is increased. Additionally, the melting point of the glass cannot be excessively high, and the uniformity of melting of raw materials is improved. The lower limit of the content of $Al_2O_3$ may be 11 mass % or more and may be 12 mass % or more, 13 mass % or more, or even 14 mass % or more. The upper limit of the content of $Al_2O_3$ may be 18 mass % or less, 17 mass % or less, 16 mass % or less, or even 15 mass % or less.

(MgO)

The composition A-2 may further include MgO. MgO included in the composition A-2 is a component responsible for adjusting the devitrification temperature and viscosity during glass forming. The lower limit of the content of MgO in the composition A-2 may be 0.1 mass % or more. The upper limit of the content of MgO may be 10 mass % or less and may be 8 mass % or less, 6 mass % or less, 5 mass % or less, or even 4 mass % or less.

(CaO)

In the composition A-2, CaO is a component responsible for adjusting the devitrification temperature and viscosity during glass forming.

When the content of CaO in the composition A-2 is 15 mass % or more and 30 mass % or less, excessive increase in the devitrification temperature of the glass can be prevented, and the devitrification temperature and the viscosity at melting of the glass can be controlled within ranges suitable for production of the glass filler. The lower limit of the content of CaO may be 16 mass % or more and may be 17 mass % or more, 18 mass % or more, or even 19 mass % or more. The upper limit of the content of CaO may be 28 mass % or less and may be 26 mass % or less, or even 25 mass % or less.

(SrO)

The composition A-2 may further include SrO. SrO included in the composition A-2 is a component responsible for adjusting the devitrification temperature and viscosity during glass forming. The upper limit of the content of SrO in the composition A-2 may be 10 mass % or less and may be 5 mass % or less, 2 mass % or less, 1 mass % or less, 0.5 mass % or less, 0.2 mass % or less, or even less than 0.1 mass %. The composition A-2 may be substantially free of SrO.

(BaO)

The composition A-2 may further include BaO. BaO included in the composition A-2 is a component responsible for adjusting the devitrification temperature and viscosity during glass forming. The upper limit of the content of BaO in the composition A-2 may be 10 mass % or less and may be 5 mass % or less, 2 mass % or less, 1 mass % or less, 0.5 mass % or less, 0.2 mass % or less, or even less than 0.1 mass %. The composition A-2 may be substantially free of BaO.

(ZnO)

The composition A-2 may further include ZnO. ZnO included in the composition A-2 is a component responsible for adjusting the devitrification temperature and viscosity during glass forming. However, ZnO is prone to evaporation and can be lost into the atmosphere during melting, and the inclusion of excess ZnO therefore increases the evaporation-induced variation in glass component proportions, making difficult control of the glass composition. The upper limit of the content of ZnO in the composition A-2 may be 10 mass % or less and may be 5 mass % or less, 2 mass % or less, or even less than 0.1 mass %. The composition A-2 may be substantially free of ZnO.

($Li_2O$, $Na_2O$, and $K_2O$)

In the composition A-2, alkali metal oxides ($Li_2O$, $Na_2O$, and $K_2O$) are components responsible for adjusting the devitrification temperature and viscosity during glass forming.

When ($Li_2O+Na_2O+K_2O$) representing the total content of the alkali metal oxides is 0 mass % or more and 2 mass % or less in the composition A-2, excessive increase in the devitrification temperature of the glass can be prevented, and the devitrification temperature and viscosity of molten glass can be controlled within ranges suitable for production of the glass filler. Additionally, the increase in the melting point of the glass can be limited to achieve more uniform melting of glass raw materials, and at the same time excessive decrease in the glass transition temperature can be avoided to ensure high heat resistance of the glass The lower limit of the ($Li_2O+Na_2O+K_2O$) may be more than 0 mass % and may be 0.1 mass % or more. The upper limit of ($Li_2O+Na_2O+K_2O$) may be 1.5 mass % or less and may be 1 mass % or less, or even 0.8 mass % or less.

($TiO_2$)

The glass composition A-2 may further include $TiO_2$. $TiO_2$ included in the composition A-2 is a component responsible for improving the meltability and chemical durability of the glass and improving the ultraviolet absorption property of the glass. The lower limit of the content of $TiO_2$ in the composition A-2 may be 0 mass % or more and may be 0.1 mass % or more. The upper limit of the content of $TiO_2$ may be 5 mass % or less and may be less than 2 mass %, 1 mass % or less, 0.5 mass % or less, or even 0.2 mass % or less. When the content of $TiO_2$ is below such an upper limit, the devitrification temperature of molten glass can be prevented from being so high due to the inclusion of $TiO_2$ that the production of the glass filler is affected. The composition A-2 may be substantially free of $TiO_2$.

($ZrO_2$)

The glass composition A-2 may further include $ZrO_2$. $ZrO_2$ included in the composition A-2 is a component responsible for adjusting the devitrification temperature and viscosity during glass forming. The upper limit of the content of $ZrO_2$ in the composition A-2 may be 5 mass % or less and may be 2 mass % or less, 1 mass % or less, or even less than 0.1 mass %. When the content of $ZrO_2$ is below such an upper limit, the devitrification temperature of molten glass can be prevented from being so high due to the inclusion of $ZrO_2$ that the production of the glass filler is affected. The composition A-2 may be substantially free of $ZrO_2$.

(Composition A-3) In another specific example of the glass composition A, the composition further includes the following components, in mass %:

$57 \leq SiO_2 \leq 65$,
$8 \leq Al_2O_3 \leq 15$,
$1 \leq MgO \leq 5$,
$15 \leq CaO \leq 30$, and
$0 \leq (Li_2O+Na_2O+K_2O) \leq 4$ (composition A-3).

A glass filler having the glass composition A-3 has high heat resistance and resists deformation upon heating to high temperature. The glass filler has high chemical durability, in particular high acid resistance. The high acid resistance offers a great benefit when, for example, the glass filler is used in an anti-corrosion lining under acidic environments. The high acid resistance offers a great benefit also when a coating is formed on the surface of the glass filler by a liquid-phase process using an acidic solution. For example, a strong acid solution is used to form a coating of titanium oxide.

The components in the glass composition A-3 will be described hereinafter.

($SiO_2$)

$SiO_2$ is a component involved in formation of the skeleton of the glass and is a main component (whose content is highest) in the composition A-3. In the composition A-3, $SiO_2$ is a component responsible for adjusting the devitrification temperature and viscosity during glass forming and for improving the acid resistance. When the content of $SiO_2$ in the composition A-3 is 57 mass % or more and 65 mass % or less, the devitrification temperature of the glass is prevented from being so high as to make production of the glass filler difficult, and the acid resistance of the glass is increased. When the content of $SiO_2$ is in this range, the melting point of the glass cannot be excessively high, and the uniformity of melting of raw materials is improved. The lower limit of the content of $SiO_2$ may be 59 mass % or more and may be more than 60 mass %. The upper limit of the content of $SiO_2$ may be 64 mass % or less and may be 63 mass % or less. The upper and lower limits of the content can be arbitrarily combined, and the same applies to the components described hereinafter (including the components contained in other specific examples of the glass composition A).

($B_2O_3$)

The composition A-3 may further include $B_2O_3$. $B_2O_3$ is a component involved in formation of the skeleton of the glass. $B_2O_3$ included in the composition A-3 is a component responsible for adjusting the devitrification temperature and viscosity during glass forming. The upper limit of the content of $B_2O_3$ in the composition A-3 may be 2 mass % or less and may be 1.5 mass % or less, 1 mass % or less, 0.5 mass % or less, or even less than 0.1 mass %. The composition A-3 may be substantially free of $B_2O_3$.

($Al_2O_3$)

$Al_2O_3$ is a component involved in formation of the skeleton of the glass. $Al_2O_3$ is a component responsible for adjusting the devitrification temperature and viscosity during glass forming and for improving the water resistance of the glass. However, the inclusion of excess $Al_2O_3$ reduces the acid resistance of the glass. When the content of $Al_2O_3$ in the composition A-3 is 8 mass % or more and 15 mass % or less, the devitrification temperature of the glass is prevented from being so high as to make production of the glass filler difficult, and the acid resistance of the glass is increased. Additionally, the melting point of the glass cannot be excessively high, and the uniformity of melting of raw materials is improved. The lower limit of the content of $Al_2O_3$ may be 9 mass % or more and may be 10 mass % or more. The upper limit of the content of $Al_2O_3$ may be 13 mass % or less and may be less than 12 mass %.

($SiO_2$—$Al_2O_3$)

In the composition A-3, the balance between the contents of $SiO_2$ and $Al_2O_3$ is important for the acid resistance of the glass. In order to improve the acid resistance of the glass, the lower limit of ($SiO_2$—$Al_2O_3$) calculated by subtracting the content of $Al_2O_3$ from the content of $SiO_2$ is preferably 47 mass % or more and more preferably more than 49 mass %. The upper limit of ($SiO_2$—$Al_2O_3$) is preferably 57 mass % or less, more preferably 56 mass % or less, even more preferably 55 mass % or less, still even more preferably 54 mass % or less, still even more preferably 53 mass % or less, and still even more preferably 52 mass % or less.

(MgO and CaO)

In the composition A-3, MgO and CaO are components responsible for adjusting the devitrification temperature and viscosity during glass forming.

When the content of MgO in the composition A-3 is 1 mass % or more and 5 mass % or less, excessive increase in the devitrification temperature of the glass can be prevented, and the devitrification temperature and the viscosity at melting of the glass can be controlled within ranges suitable for production of the glass filler. The lower limit of the content of MgO may be 1.5 mass % or more and may be 2 mass % or more. The upper limit of the content of MgO may be 4.5 mass % or less and may be 4 mass % or less.

When the content of CaO in the composition A-3 is 15 mass % or more and 30 mass % or less, excessive increase in the devitrification temperature of the glass can be prevented, and the devitrification temperature and the viscosity at melting of the glass can be controlled within ranges suitable for production of the glass filler. The lower limit of the content of CaO may be 18 mass % or more and may be 19 mass % or more, or even 20 mass % or more. The upper limit of the content of CaO may be 27 mass % or less and may be 25 mass % or less, or even 24 mass % or less.

(SrO)

The composition A-3 may further include SrO. SrO included in the composition A-3 is a component responsible for adjusting the devitrification temperature and viscosity during glass forming. However, the inclusion of excess SrO reduces the acid resistance of the glass. Thus, the upper limit of the content of SrO in the composition A-3 may be 10 mass % or less and may be 5 mass % or less, 2 mass % or less, or even less than 0.1 mass %. The composition A-3 may be substantially free of SrO.

(BaO)

The composition A-3 may further include BaO. BaO included in the composition A-3 is a component responsible for adjusting the devitrification temperature and viscosity during glass forming. However, the inclusion of excess BaO reduces the acid resistance of the glass. Thus, the upper limit of the content of BaO in the composition A-3 may be 10 mass % or less and may be 5 mass % or less, 2 mass % or less, or even less than 0.1 mass %. The composition A-3 may be substantially free of BaO.

(ZnO)

The composition A-3 may further include ZnO. ZnO included in the composition A-3 is a component responsible for adjusting the devitrification temperature and viscosity during glass forming. However, ZnO is prone to evaporation and can be lost into the atmosphere during melting, and the inclusion of excess ZnO therefore increases the evaporation-induced variation in glass component proportions, making difficult control of the glass composition. The upper limit of the content of ZnO in the composition A-3 may be 10 mass % or less and may be 5 mass % or less, 2 mass % or less, or even less than 0.1 mass %. The composition A-3 may be substantially free of ZnO.

($Li_2O$, $Na_2O$, and $K_2O$)

In the composition A-3, alkali metal oxides ($Li_2O$, $Na_2O$, and $K_2O$) are components responsible for adjusting the devitrification temperature and viscosity during glass forming.

When ($Li_2O$+$Na_2O$+$K_2O$) representing the total content of the alkali metal oxides is 0 mass % or more and 4 mass % or less in the composition A-3, excessive increase in the devitrification temperature of the glass can be prevented, and the devitrification temperature and viscosity of molten glass can be controlled within ranges suitable for production of the glass filler. Additionally, the increase in the melting point of the glass can be limited to achieve more uniform melting of glass raw materials, and at the same time excessive decrease in the glass transition temperature can be avoided to ensure high heat resistance of the glass The lower limit of ($Li_2O+Na_2O+K_2O$) may be more than 0 mass % and may be 0.1 mass % or more. The upper limit of ($Li_2O+Na_2O+K_2O$) may be 3 mass % or less and may be less than 2 mass %. When uniform melting of glass raw materials and ease of production of the glass filler are given high priority, ($Li_2O+Na_2O+K_2O$) in the composition A-3 may be 2 mass % or more and 4 mass % or less. When the alkali resistance of the glass filler is given high priority, ($Li_2O+Na_2O+K_2O$) in the composition A-3 may be less than 0.1 mass %.

Among the alkali metal oxides in the composition A-3, lithium oxide ($Li_2O$) makes a particularly significant contribution to the above-described effect attributed to the alkali metal oxides. In view of this, the lower limit of the content of $Li_2O$ in the composition A-3 may be 0.1 mass % or more and may be 0.4 mass % or more. The upper limit of the content of $Li_2O$ may be 3 mass % or less and may be less than 2 mass %, or even 1 mass % or less. When uniform melting of glass raw materials and ease of production of the glass filler are given high priority, the content of $Li_2O$ in the composition A-3 may be 2 mass % or more and 4 mass % or less.

($TiO_2$)

The glass composition A-3 may further include $TiO_2$. $TiO_2$ included in the composition A-3 is a component responsible for improving the meltability and chemical durability of the glass and improving the ultraviolet absorption property of the glass. The lower limit of the content of $TiO_2$ in the composition A-3 may be 0 mass % or more and may be 0.1 mass % or more. The upper limit of the content of $TiO_2$ may be 5 mass % or less and may be less than 2 mass %, 1 mass % or less, or even 0.5 mass % or less. When the content of $TiO_2$ is below such an upper limit, the devitrification temperature of molten glass can be prevented from being so high due to the inclusion of $TiO_2$ that the production of the glass filler is affected. The composition A-3 may be substantially free of $TiO_2$.

($ZrO_2$)

The glass composition A-3 may further include $ZrO_2$. $ZrO_2$ included in the composition A-3 is a component responsible for adjusting the devitrification temperature and viscosity during glass forming. The upper limit of the content of $ZrO_2$ in the composition A-3 may be 5 mass % or less and may be 2 mass % or less, 1 mass % or less, or even less than 0.1 mass %. When the content of $ZrO_2$ is below such an upper limit, the devitrification temperature of molten glass can be prevented from being so high due to the inclusion of $ZrO_2$ that the production of the glass filler is affected. The composition A-3 may be substantially free of $ZrO_2$.

(Composition A-4)

In another specific example of the glass composition A, the composition further includes the following components, in mass %:
65<$SiO_2$≤70,
5≤$Al_2O_3$≤15,
1≤MgO≤10,
10≤CaO≤25, and
0≤($Li_2O+Na_2O+K_2O$)≤4 (composition A-4).

A glass filler having the glass composition A-4 has high heat resistance and resists deformation upon heating to high temperature. The glass filler has high chemical durability, in particular high acid resistance. The high acid resistance offers a great benefit when, for example, the glass filler is used in an anti-corrosion lining under acidic environments. The high acid resistance offers a great benefit also when a coating is formed on the surface of the glass filler by a liquid-phase process using an acidic solution. For example, a strong acid solution is used to form a coating of titanium oxide.

The components in the glass composition A-4 will be described hereinafter.

($SiO_2$)

$SiO_2$ is a component involved in formation of the skeleton of the glass and is a main component (whose content is highest) in the composition A-4. In the composition A-4, $SiO_2$ is a component responsible for adjusting the devitrification temperature and viscosity during glass forming and for improving the acid resistance. When the content of $SiO_2$ in the composition A-4 is more than 65 mass % and 70 mass % or less, the devitrification temperature of the glass is prevented from being so high as to make production of the glass filler difficult, and the acid resistance of the glass is increased. When the content of $SiO_2$ is in this range, the melting point of the glass cannot be excessively high, and the uniformity of melting of raw materials is improved. The lower limit of the content of $SiO_2$ may be 66 mass % or more. The upper limit of the content of $SiO_2$ may be 69 mass % or less and may be 68 mass % or less, or even 67 mass % or less.

($B_2O_3$)

The composition A-4 may further include $B_2O_3$. $B_2O_3$ is a component involved in formation of the skeleton of the glass. $B_2O_3$ included in the composition A-4 is a component responsible for adjusting the devitrification temperature and viscosity during glass forming. The upper limit of the content of $B_2O_3$ in the composition A-4 may be 2 mass % or less and may be 1.5 mass % or less, 1 mass % or less, 0.5 mass % or less, or even less than 0.1 mass %. The composition A-4 may be substantially free of $B_2O_3$.

($Al_2O_3$)

$Al_2O_3$ is a component involved in formation of the skeleton of the glass. $Al_2O_3$ is a component responsible for adjusting the devitrification temperature and viscosity during glass forming and for improving the water resistance of the glass. However, the inclusion of excess $Al_2O_3$ reduces the acid resistance of the glass. When the content of $Al_2O_3$ in the composition A-4 is 5 mass % or more and 15 mass % or less, the devitrification temperature of the glass is prevented from being so high as to make production of the glass filler difficult, and the acid resistance of the glass is increased. Additionally, the melting point of the glass cannot be excessively high, and the uniformity of melting of raw materials is improved. The lower limit of the content of $Al_2O_3$ may be 6 mass % or more and may be 8 mass % or more, or even 10 mass % or more. The upper limit of the content of $Al_2O_3$ may be 13 mass % or less and may be less than 12 mass %.

($SiO_2$—$Al_2O_3$)

In the composition A-4, the balance between the contents of $SiO_2$ and $Al_2O_3$ are important for the acid resistance of the glass. In order to improve the acid resistance of the glass, the lower limit of ($SiO_2$—$Al_2O_3$) calculated by subtracting the content of $Al_2O_3$ from the content of $SiO_2$ is preferably more than 50 mass %, more preferably 51 mass % or more, even more preferably 52 mass % or more, and most preferably more than 53 mass %. The upper limit of ($SiO_2$—$Al_2O_3$) is preferably 60 mass % or less, more preferably 59 mass % or less, even more preferably 58 mass % or less, and still even more preferably 57 mass % or less.

(MgO and CaO)

In the composition A-4, MgO and CaO are components responsible for adjusting the devitrification temperature and viscosity during glass forming.

When the content of MgO in the composition A-4 is 1 mass % or more and 10 mass % or less, excessive increase in the devitrification temperature of the glass can be prevented, and the devitrification temperature and the viscosity at melting of the glass can be controlled within ranges suitable for production of the glass filler. The lower limit of the content of MgO may be 2 mass % or more. The upper limit of the content of MgO may be 8 mass % or less and may be 5 mass % or less, or even 4 mass % or less.

When the content of CaO in the composition A-4 is 10 mass % or more and 25 mass % or less, excessive increase in the devitrification temperature of the glass can be prevented, and the devitrification temperature and the viscosity at melting of the glass can be controlled within ranges suitable for production of the glass filler. The lower limit of the content of CaO may be 12 mass % or more and may be 14 mass % or more, or even more than 15 mass %. The upper limit of the content of CaO may be 23 mass % or less and may be 21 mass % or less, or even 20 mass % or less.

(SrO)

The composition A-4 may further include strontium oxide (SrO). SrO included in the composition A-4 is a component responsible for adjusting the devitrification temperature and viscosity during glass forming. However, the inclusion of excess SrO reduces the acid resistance of the glass. Thus, the upper limit of the content of SrO in the composition A-4 may be 10 mass % or less, 5 mass % or less, 2 mass % or less, or even less than 0.1 mass %. The composition A-4 may be substantially free of SrO.

(BaO)

The composition A-4 may further include barium oxide (BaO). BaO included in the composition A-4 is a component responsible for adjusting the devitrification temperature and viscosity during glass forming. However, the inclusion of excess BaO reduces the acid resistance of the glass. Thus, the upper limit of the content of BaO in the composition A-4 may be 10 mass % or less and may be 5 mass % or less, 2 mass % or less, or even less than 0.1 mass %. The composition A-4 may be substantially free of BaO.

(ZnO)

The composition A-4 may further include zinc oxide (ZnO). ZnO included in the composition A-4 is a component responsible for adjusting the devitrification temperature and viscosity during glass forming. However, ZnO is prone to evaporation and can be lost into the atmosphere during melting, and the inclusion of excess ZnO therefore increases the evaporation-induced variation in glass component proportions, making difficult control of the glass composition. The upper limit of the content of ZnO in the composition A-4 may be 10 mass % or less and may be 5 mass % or less, 2 mass % or less, or even less than 0.1 mass %. The composition A-4 may be substantially free of ZnO.

($Li_2O$, $Na_2O$, and $K_2O$)

In the composition A-4, alkali metal oxides ($Li_2O$, $Na_2O$, and $K_2O$) are components responsible for adjusting the devitrification temperature and viscosity during glass forming.

When ($Li_2O$+$Na_2O$+$K_2O$) representing the total content of the alkali metal oxides is 0 mass % or more and 4 mass % or less in the composition A-4, excessive increase in the devitrification temperature of the glass can be prevented, and the devitrification temperature and viscosity of molten glass can be controlled within ranges suitable for production of the glass filler. Additionally, the increase in the melting point of the glass can be limited to achieve more uniform melting of glass raw materials, and at the same time excessive decrease in the glass transition temperature can be avoided to ensure high heat resistance of the glass The lower limit of ($Li_2O$+$Na_2O$+$K_2O$) may be 0.1 mass % or more, 1 mass % or more, 1.5 mass % or more, or even 2 mass % or more. The upper limit of ($Li_2O$+$Na_2O$+$K_2O$) may be 3.5 mass % or less and may be less than 3 mass %.

Among the alkali metal oxides in the composition A-4, lithium oxide ($Li_2O$) makes a particularly significant contribution to the above-described effect attributed to the alkali metal oxides. In view of this, the lower limit of the content of $Li_2O$ in the composition A-4 may be 0.1 mass % or more and may be 0.5 mass % or more, or even 1 mass % or more. The upper limit of the content of $Li_2O$ may be 3 mass % or less and may be less than 2 mass %, or 1 mass % or less.

($TiO_2$)

The glass composition A-4 may further include titanium oxide ($TiO_2$). $TiO_2$ included in the composition A-4 is a component responsible for improving the meltability and chemical durability of the glass and improving the ultraviolet absorption property of the glass. The lower limit of the content of $TiO_2$ in the composition A-4 may be 0 mass % or more and may be 0.1 mass % or more. The upper limit of the content of $TiO_2$ may be 5 mass % or less and may be less than 2 mass %, 1 mass % or less, or even 0.5 mass % or less. When the content of $TiO_2$ is below such an upper limit, the devitrification temperature of molten glass can be prevented from being so high due to the inclusion of $TiO_2$ that the production of the glass filler is affected. The composition A-4 may be substantially free of $TiO_2$.

($ZrO_2$)

The glass composition A-4 may further include zirconium oxide ($ZrO_2$). $ZrO_2$ contained in composition A-4 is a component responsible for adjusting the devitrification temperature and viscosity during glass forming. The upper limit of the content of $ZrO_2$ in the composition A-4 may be 5 mass % or less and may be 2 mass % or less, 1 mass % or less, or even less than 0.1 mass %. When the content of $ZrO_2$ is below such an upper limit, the devitrification temperature of molten glass can be prevented from being so high due to the inclusion of $ZrO_2$ that the production of the glass filler is affected. The composition A-4 may be substantially free of $ZrO_2$.

(Composition A-5)

In another specific example of the glass composition A, the composition further includes the following components, in mass %:

60≤$SiO_2$≤70,
5≤$Al_2O_3$≤15,
1≤MgO≤10,
10≤CaO≤25, and
4<($Li_2O$+$Na_2O$+$K_2O$)<9 (composition A-5).

A glass filler having the glass composition A-5 has high heat resistance and resists deformation upon heating to high temperature. The glass filler has high chemical durability, in particular high acid resistance. The high acid resistance offers a great benefit when, for example, the glass filler is used in an anti-corrosion lining under acidic environments. The high acid resistance offers a great benefit also when a coating is formed on the surface of the glass filler by a liquid-phase process using an acidic solution. For example, a strong acid solution is used to form a coating of titanium oxide.

The components in the glass composition A-5 will be described hereinafter.

($SiO_2$)

$SiO_2$ is a component involved in formation of the skeleton of the glass and is a main component (whose content is highest) in the composition A-5. In the composition A-5, $SiO_2$ is a component responsible for adjusting the devitrification temperature and viscosity during glass forming and for improving the acid resistance. When the content of $SiO_2$ in the composition A-5 is 60 mass % or more and 70 mass % or less, the devitrification temperature of the glass is prevented from being so high as to make production of the glass filler difficult, and the acid resistance of the glass is increased. When the content of $SiO_2$ is in this range, the melting point of the glass cannot be excessively high, and the uniformity of melting of raw materials is improved. The lower limit of the content of $SiO_2$ may be 63 mass % or more and may be 64 mass % or more or even more than 65 mass %. The upper limit of the content of $SiO_2$ may be 69 mass % or less and may be 68 mass % or less, or even 67 mass % or less.

($B_2O_3$)

The composition A-5 may further include $B_2O_3$. $B_2O_3$ is a component involved in formation of the skeleton of the glass. $B_2O_3$ included in the composition A-5 is a component responsible also for adjusting the devitrification temperature and viscosity during glass forming. The upper limit of the content of $B_2O_3$ in the composition A-5 may be 2 mass % or less and may be 1.5 mass % or less, 1 mass % or less, 0.5 mass % or less, or even less than 0.1 mass %. The composition A-5 may be substantially free of $B_2O_3$.

($Al_2O_3$)

$Al_2O_3$ is a component involved in formation of the skeleton of the glass. $Al_2O_3$ is a component responsible also for adjusting the devitrification temperature and viscosity during glass forming and for improving the water resistance of the glass. However, the inclusion of excess $Al_2O_3$ reduces the acid resistance of the glass. When the content of $Al_2O_3$ in the composition A-5 is 5 mass % or more and 15 mass % or less, the devitrification temperature of the glass is prevented from being so high as to make production of the glass filler difficult, and the acid resistance of the glass is increased. Additionally, the melting point of the glass cannot be excessively high, and the uniformity of melting of raw materials is improved. The lower limit of the content of $Al_2O_3$ may be 6 mass % or more and may be 8 mass % or more, 9 mass % or more, or even 10 mass % or more. The upper limit of the content of $Al_2O_3$ may be 13 mass % or less and may be less than 12 mass %.

($SiO_2$—$Al_2O_3$)

In the composition A-5, the balance between the contents of $SiO_2$ and $Al_2O_3$ are important for the acid resistance of the glass. In order to improve the acid resistance of the glass, the lower limit of ($SiO_2$—$Al_2O_3$) calculated by subtracting the content of $Al_2O_3$ from the content of $SiO_2$ is preferably more than 50 mass %, more preferably 51 mass % or more, even more preferably 52 mass % or more, and most preferably more than 53 mass %. The upper limit of ($SiO_2$—$Al_2O_3$) is preferably 60 mass % or less, more preferably 59 mass % or less, even more preferably 58 mass % or less, and still even more preferably 57 mass % or less.

(MgO and CaO)

In the composition A-5, MgO and CaO are components responsible for adjusting the devitrification temperature and viscosity during glass forming.

When the content of MgO in the composition A-5 is 1 mass % or more and 10 mass % or less, excessive increase in the devitrification temperature of the glass can be prevented, and the devitrification temperature and the viscosity at melting of the glass can be controlled within ranges suitable for production of the glass filler. The lower limit of the content of MgO may be 2 mass % or more. The upper limit of the content of MgO may be 8 mass % or less, 5 mass % or less, or even 4 mass % or less.

When the content of CaO is 10 mass % or more and 25 mass % or less in the composition A-5, excessive increase in the devitrification temperature of the glass can be prevented, and the devitrification temperature and the viscosity at melting of the glass can be controlled within ranges suitable for production of the glass filler. The lower limit of the content of CaO may be 12 mass % or more and may be 13 mass % or more, 14 mass % or more, or even more than 15 mass %. The upper limit of the content of CaO may be 23 mass % or less and may be 21 mass % or less, 20 mass % or less, 19 mass % or less, or even 18 mass % or less.

(SrO)

The composition A-5 may further include SrO. SrO included in the composition A-5 is a component responsible for adjusting the devitrification temperature and viscosity during glass forming. However, the inclusion of excess SrO reduces the acid resistance of the glass. Thus, the upper limit of the content of SrO in the composition A-5 may be 10 mass % or less and may be 5 mass % or less, 2 mass % or less, or even less than 0.1 mass %. The composition A-5 may be substantially free of SrO.

(BaO)

The composition A-5 may further include BaO. BaO included in the composition A-5 is a component responsible for adjusting the devitrification temperature and viscosity during glass forming. However, the inclusion of excess BaO reduces the acid resistance of the glass. Thus, the upper limit of the content of BaO in the composition A-5 may be 10 mass % or less and may be 5 mass % or less, 2 mass % or less, or even less than 0.1 mass %. The composition A-5 may be substantially free of BaO.

(ZnO)

The composition A-5 may further include ZnO. ZnO included in the composition A-5 is a component responsible for adjusting the devitrification temperature and viscosity during glass forming. However, ZnO is prone to evaporation and can be lost into the atmosphere during melting, and the inclusion of excess ZnO therefore increases the evaporation-induced variation in glass component proportions, making difficult control of the glass composition. The upper limit of the content of ZnO in the composition A-5 may be 10 mass % or less and may be 5 mass % or less, 2 mass % or less, or even less than 0.1 mass %. The composition A-5 may be substantially free of ZnO.

($Li_2O$, $Na_2O$, and $K_2O$)

In the composition A-5, alkali metal oxides ($Li_2O$, $Na_2O$, and $K_2O$) are components responsible for adjusting the devitrification temperature and viscosity during glass forming.

When ($Li_2O$+$Na_2O$+$K_2O$) representing the total content of the alkali metal oxides is more than 4 mass % and less than 9 mass % in the composition A-5, excessive increase in the devitrification temperature of the glass can be prevented, and the devitrification temperature and viscosity of molten glass can be controlled within ranges suitable for production of the glass filler. Additionally, the increase in the melting point of the glass can be limited to achieve more uniform melting of glass raw materials, and at the same time excessive decrease in the glass transition temperature can be avoided to ensure high heat resistance of the glass The lower limit of ($Li_2O+Na_2O+K_2O$) may be 4.5 mass % or more and may be 5 mass % or more. The upper limit of ($Li_2O+Na_2O+K_2O$) may be 8.5 mass % or less and may be 8 mass % or less.

Among the alkali metal oxides in the composition A-5, lithium oxide ($Li_2O$) makes a particularly significant contribution to the above-described effect attributed to the alkali metal oxides. In view of this, the lower limit of the content of $Li_2O$ in the composition A-5 may be 0.1 mass % or more and may be 0.5 mass % or more, or even 1 mass % or more. The upper limit of the content of $Li_2O$ may be 3 mass % or less and may be less than 2 mass %.

($TiO_2$)

The glass composition A-5 may further include $TiO_2$. $TiO_2$ included in the composition A-5 is a component responsible for improving the meltability and chemical durability of the glass and improving the ultraviolet absorption property of the glass. The lower limit of the content of $TiO_2$ in the composition A-5 may be 0 mass % or more and may be 0.1 mass % or more. The upper limit of the content of $TiO_2$ may be 5 mass % or less and may be less than 2 mass %, 1 mass % or less, or even 0.5 mass % or less. When the content of $TiO_2$ is below such an upper limit, the devitrification temperature of molten glass can be prevented from being so high due to the inclusion of $TiO_2$ that the production of the glass filler is affected. The composition A-5 may be substantially free of $TiO_2$.

($ZrO_2$)

The glass composition A-5 may further include $ZrO_2$. $ZrO_2$ contained in composition A-5 is a component responsible for adjusting the devitrification temperature and viscosity during glass forming. The upper limit of the content of $ZrO_2$ in the composition A-5 may be 5 mass % or less and may be 2 mass % or less, 1 mass % or less, or even less than 0.1 mass %. When the content of $ZrO_2$ is below such an upper limit, the devitrification temperature of molten glass can be prevented from being so high due to the inclusion of $ZrO_2$ that the production of the glass filler is affected. The composition A-5 may be substantially free of $ZrO_2$.

(Compositions A-6 and A-7)

In another specific example of the glass composition A, the composition further includes the following components, in mass %:

60≤$SiO_2$≤75,
5<$Al_2O_3$≤15,
5≤CaO≤20,
6≤$Na_2O$≤13, and
9≤($Li_2O+Na_2O+K_2O$)≤13 (composition A-6).

In another specific example of the glass composition A, the composition further includes the following components, in mass %:

60≤$SiO_2$≤75,
5<$Al_2O_3$≤15,
3≤CaO≤15,
9≤$Na_2O$≤20, and
13<($Li_2O+Na_2O+K_2O$)≤20 (composition A-7).

A glass filler having the glass composition A-6 or A-7 has high heat resistance and high chemical durability, in particular high acid resistance. The glass filler can be formed to have a more uniform size by controlling the working temperature of the raw glass during the formation of the glass filler. The working temperature is, for example, 1180 to 1300° C.

The components in the glass compositions A-6 and A-7 will be described hereinafter.

($SiO_2$)

$SiO_2$ is a component involved in formation of the skeleton of the glass and is a main component (whose content is highest) in the compositions A-6 and A-7. In the compositions A-6 and A-7, $SiO_2$ is a component responsible for adjusting the devitrification temperature and viscosity during glass forming with retention of the heat resistance of the glass and for improving the acid resistance. When the content of $SiO_2$ in the compositions A-6 and A-7 is 60 mass % or more and 75 mass % or less, the devitrification temperature of the glass is prevented from being so high as to make production of the glass filler difficult, and the acid resistance of the glass is increased. When the content of $SiO_2$ is in this range, the melting point of the glass cannot be excessively high, and the uniformity of melting of raw materials is improved. The lower limit of the content of $SiO_2$ may be 63 mass % or more and may be 64 mass % or more, or even 65 mass % or more. The upper limit of the content of $SiO_2$ may be 70 mass % or less and may be 68 mass % or less, or even 67 mass % or less.

($B_2O_3$)

The compositions A-6 and A-7 may further include $B_2O_3$. $B_2O_3$ is a component involved in formation of the skeleton of the glass. $B_2O_3$ included in the compositions A-6 and A-7 is a component responsible also for adjusting the devitrification temperature and viscosity during glass forming. The upper limit of the content of $B_2O_3$ in the compositions A-6 and A-7 may be 6 mass % or less and may be less than 2 mass %, less than 1 mass %, or even less than 0.1 mass %. The compositions A-6 and A-7 may be substantially free of $B_2O_3$.

($Al_2O_3$)

$Al_2O_3$ is a component involved in formation of the skeleton of the glass. In the compositions A-6 and A-7, $Al_2O_3$ is a component responsible also for adjusting the devitrification temperature and viscosity during glass forming with retention of the heat resistance of the glass and for improving the water resistance of the glass. However, the inclusion of excess $Al_2O_3$ reduces the acid resistance of the glass. When the content of $Al_2O_3$ in the compositions A-6 and A-7 is more than 5 mass % and 15 mass % or less, the inclusion of $Al_2O_3$ provides a sufficient effect on the adjustment of the devitrification temperature and viscosity. Additionally, the devitrification temperature of the glass is prevented from being so high as to make production of the glass filler difficult, and the water resistance and acid resistance of the glass are increased. Further, the melting point of the glass cannot be excessively high, and the uniformity of melting of raw materials is improved. The lower limit of the content of $Al_2O_3$ may be 6 mass % or more and may be 7 mass % or more, or even 8 mass % or more. The upper limit of the content of $Al_2O_3$ may be 13 mass % or less and may be 12 mass % or less, or even less than 12 mass %.

(MgO and CaO)

The compositions A-6 and A-7 may further include MgO. MgO included in the compositions A-6 and A-7 is a component responsible for adjusting the devitrification temperature and viscosity during glass forming with retention of the heat resistance of the glass. That is, MgO may be included in the compositions A-6 and A-7 as a component for adjusting the devitrification temperature and viscosity during glass forming, although the inclusion of MgO is not essential. The lower limit of the content of MgO in the compositions A-6 and A-7 may be 0 mass % or more and may be 0.1 mass % or more, 1 mass % or more, or even 2 mass % or more. The upper limit of the content of MgO may be 10 mass % or less and may be 8 mass % or less, 5 mass % or less, or even 4 mass % or less. When MgO is included in the compositions A-6 and A-7 and the content of MgO is within the above range, excessive increase in the devitrification temperature of the glass can be prevented, and the devitrification temperature and the viscosity at melting of the glass can be controlled within ranges suitable for production of the glass filler.

In the compositions A-6 and A-7, CaO is a component responsible for adjusting the devitrification temperature and viscosity during glass forming with retention of the heat resistance of the glass. The content of CaO varies depending on ($Li_2O+Na_2O+K_2O$) representing the total content of alkali metal oxides.

When ($Li_2O+Na_2O+K_2O$) representing the total content of alkali metal oxides is 9 mass % or more and 13 mass % or less, the content of CaO is 5 mass % or more and 20 mass % or less (composition A-6). For the composition A-6, when the total content of the alkali metal oxides and the content of CaO are within these ranges, excessive increase in the devitrification temperature of the glass can be prevented, and the devitrification temperature and the viscosity at melting of the glass can be controlled within ranges suitable for production of the glass filler. In this case, the lower limit of the content of CaO may be 8 mass % or more and may be 9 mass % or more, 10 mass % or more, or even more than 10 mass %. The upper limit of the content of CaO may be 18 mass % or less and may be 16 mass % or less, or even 15 mass % or less.

When ($Li_2O+Na_2O+K_2O$) representing the total content of alkali metal oxides is more than 13 mass % and 20 mass % or less, the content of CaO is 3 mass % or more and 15 mass % or less (composition A-7). For the composition A-7, when the total content of alkali metal oxides and the content of CaO are within these ranges, excessive increase in the devitrification temperature of the glass can be prevented, and the devitrification temperature and the viscosity at melting of the glass can be controlled within ranges suitable for production of the glass filler. In this case, the lower limit of the content of CaO may be 4 mass % or more and may be 5 mass % or more, or even 6 mass % or more. The upper limit of the content of CaO may be 12 mass % or less and may be 10 mass % or less.

For the compositions A-6 and A-7, when ease of production of the glass filler is given priority, it is conceivable to take into consideration (MgO+CaO) representing the total content of MgO and CaO which are components responsible for adjusting the devitrification temperature and viscosity during glass forming. The preferred value of (MgO+CaO) varies depending on ($Li_2O+Na_2O+K_2O$) representing the total content of the alkali metal oxides in the compositions A-6 and A-7.

When ($Li_2O+Na_2O+K_2O$) representing the total content of the alkali metal oxides is 9 mass % or more and 13 mass % or less, (MgO+CaO) may be 5 mass % or more and 30 mass % or less. For the composition A-6, when the total content of the alkali metal oxides and the total content of MgO and CaO are within these ranges, excessive increase in the devitrification temperature of the glass can be prevented, and the devitrification temperature and the viscosity at melting of the glass can be controlled within ranges suitable for production of the glass filler. Additionally, high acid resistance of the glass can be ensured. In this case, the lower limit of (MgO+CaO) may be 11 mass % or more and may be 12 mass % or more, 13 mass % or more, or even 14 mass % or more. The upper limit of (MgO+CaO) may be 26 mass % or less and may be 23 mass % or less or even 20 mass % or less.

When ($Li_2O+Na_2O+K_2O$) representing the total content of the alkali metal oxides is more than 13 mass % and 20 mass % or less, (MgO+CaO) may be 3 mass % or more and 25 mass % or less. For the composition A-7, when the total content of the alkali metal oxides and the total content of MgO and CaO are within these ranges, excessive increase in the devitrification temperature of the glass can be prevented, and the devitrification temperature and the viscosity at melting of the glass can be controlled within ranges suitable for production of the glass filler. Additionally, high acid resistance of the glass can be ensured. In this case, the lower limit of (MgO+CaO) may be 6 mass % or more and may be 8 mass % or more, 9 mass % or more, or even 10 mass % or more. The upper limit of (MgO+CaO) may be 20 mass % or less and may be 17 mass % or less, or even 15 mass % or less.

(SrO)

The compositions A-6 and A-7 may further include SrO. SrO included in the compositions A-6 and A-7 is a component responsible for adjusting the devitrification temperature and viscosity during glass forming. That is, SrO may be included in the compositions A-6 and A-7 as a component for adjusting the devitrification temperature and viscosity during glass forming, although the inclusion of SrO is not essential. However, the inclusion of excessive SrO reduces the acid resistance of the glass. Thus, the upper limit of the content of SrO in the compositions A-6 and A-7 may be 10 mass % or less and may be 5 mass % or less, 2 mass % or less, or even less than 0.1 mass %. The compositions A-6 and A-7 may be substantially free of SrO.

(BaO)

The compositions A-6 and A-7 may further include barium oxide (BaO). BaO included in the compositions A-6 and A-7 is a component responsible for adjusting the devitrification temperature and viscosity during glass forming. That is, BaO may be included in the compositions A-6 and A-7 as a component for adjusting the devitrification temperature and viscosity during glass forming, although the inclusion of BaO is not essential. However, the inclusion of excessive BaO reduces the acid resistance of the glass. Thus, the upper limit of the content of BaO in the compositions A-6 and A-7 may be 10 mass % or less and may be 5 mass % or less, 2 mass % or less, or even less than 0.1 mass %. The compositions A-6 and A-7 may be substantially free of BaO.

($Li_2O$, $Na_2O$, and $K_2O$)

In the compositions A-6 and A-7, the alkali metal oxides ($Li_2O$, $Na_2O$, and $K_2O$) are components responsible for adjusting the devitrification temperature and viscosity during glass forming with retention of the heat resistance of the glass. ($Li_2O+Na_2O+K_2O$) representing the total content of the alkali metal oxides is 9 mass % or more and 13 mass % or less in the composition A-6 and more than 13 mass % and 20 mass % or less in the composition A-7. When the total content of the alkali metal oxides in the compositions A-6 and A-7 is within these ranges, the devitrification temperature and the viscosity at melting of the glass are decreased, and the formability of the glass is improved, so that the efficiency of production of the glass filler is increased. The adjustment of the total content of the alkali metal oxides, combined with control of the working temperature of the raw glass during formation of the glass filler, can allow the glass filler to have a more uniform size. Further, in this case, more uniform melting of glass raw materials can be achieved, and at the same time excessive decrease in glass transition temperature can be avoided to ensure high heat resistance of the glass.

In the composition A-6, the lower limit of ($Li_2O+Na_2O+K_2O$) may be 9.5 mass % or more and may be 10 mass % or more. In the composition A-6, the upper limit of ($Li_2O+Na_2O+K_2O$) may be 12.5 mass % or less and may be 12 mass % or less. In the composition A-7, the lower limit of ($Li_2O+Na_2O+K_2O$) may be 13.5 mass % or more. In the composition A-7, the upper limit of ($Li_2O+Na_2O+K_2O$) may be 18 mass % or less and may be 16 mass % or less, 15 mass % or less, or even less than 15 mass %.

Among the alkali metal oxides in the compositions A-6 and A-7, $Li_2O$ makes a particularly significant contribution to the above-described effect attributed to the alkali metal oxides. The inclusion of $Li_2O$ can decrease the working temperature of the raw glass during formation of the glass filler, and the decrease in working temperature facilitates the formation of the glass filler, resulting in an increase in production efficiency. However, the inclusion of excess $Li_2O$ lowers the glass transition temperature and reduces the heat resistance of the glass. The lower limit of the content of $Li_2O$ in the compositions A-6 and A-7 may be 0 mass % or more and may be 0.1 mass % or more, 0.5 mass % or more, or even 1 mass % or more. The upper limit of the content of $Li_2O$ may be 5 mass % or less and may be 4 mass % or less, 3 mass % or less, 2 mass % or less, or even less than 2 mass %.

The content of $Na_2O$ is 6 mass % or more and 13 mass % or less for the composition A-6 and 9 mass % or more and 20 mass % or less for the composition A-7. For both of the compositions, when the content of $Na_2O$ is within such a range, the above-described effect attributed to the alkali metal oxides can be more reliably obtained.

In the composition A-6, the lower limit of the content of $Na_2O$ may be 7 mass % or more and may be 8 mass % or more, or even 9 mass % or more. The upper limit of the content of $Na_2O$ may be 12 mass % or less.

In the composition A-7, the lower limit of the content of $Na_2O$ may be 10 mass % or more and may be 11 mass % or more, or even 12 mass % or more. The upper limit of the content of $Na_2O$ may be 17 mass % or less and may be 15 mass % or less, less than 15 mass %, or even 14 mass % or less.

In the compositions A-6 and A-7, the lower limit of the content of $K_2O$ may be 0 mass % or more and may be 0.1 mass % or more, or even 0.5 mass % or more. The upper limit of the content of $K_2O$ may be 5 mass % or less and may be 3 mass % or less, 2 mass % or less, less than 2 mass %, or even 1 mass % or less.

(ZnO)

The glass compositions A-6 and A-7 may further include zinc oxide (ZnO). ZnO included in the compositions A-6 and A-7 is a component responsible for adjusting the devitrification temperature and viscosity during glass forming. However, ZnO is prone to evaporation and can be lost into the atmosphere during melting, and the inclusion of excess ZnO therefore increases the evaporation-induced variation in glass component proportions, making difficult control of the glass composition. The upper limit of the content of ZnO in the compositions A-6 and A-7 may be 10 mass % or less and may be 5 mass % or less, 2 mass % or less, or even less than 0.1 mass %. The compositions A-6 and A-7 may be substantially free of ZnO.

($TiO_2$)

The glass compositions A-6 and A-7 may further include $TiO_2$. $TiO_2$ included in the compositions A-6 and A-7 is a component responsible for improving the meltability and chemical durability of the glass and for adjusting the optical properties of the glass, such as improving the ultraviolet absorption property of the glass. In the compositions A-6 and A-7, the lower limit of the content of $TiO_2$ may be 0 mass % or more and may be 0.1 mass % or more. The upper limit of the content of $TiO_2$ may be 5 mass % or less and may be 2 mass % or less, 1 mass % or less, or even less than 1 mass %. When the content of $TiO_2$ is below such an upper limit, the devitrification temperature of molten glass can be prevented from being so high due to the inclusion of $TiO_2$ that the production of the glass filler is affected. The compositions A-6 and A-7 may be substantially free of $TiO_2$.

($ZrO_2$)

The glass compositions A-6 and A-7 may further include zirconium oxide ($ZrO_2$). $ZrO_2$ included in the compositions A-6 and A-7 is a component responsible for adjusting the devitrification temperature and viscosity during glass forming. The upper limit of the content of $ZrO_2$ in the compositions A-6 and A-7 may be 5 mass % or less and may be 2 mass % or less, 1 mass % or less, or even less than 0.1 mass %. When the content of $ZrO_2$ is below such an upper limit, the devitrification temperature of molten glass can be prevented from being so high due to the inclusion of $ZrO_2$ that the production of the glass filler is affected. The compositions A-6 and A-7 may be substantially free of $ZrO_2$.

(Composition A-8)

In another specific example of the glass composition A, the composition further includes the following components, in mass %:

$60 \leq SiO_2 \leq 80$,
$5 \leq B_2O_3 \leq 20$,
$5 \leq Al_2O_3 \leq 15$,
$0.1 \leq (MgO+CaO) < 1$, and
$9 < Na_2O < 13$ (composition A-8).

A glass filler having the glass composition A-8 can be more suitable for incorporation into resins (in particular, acrylic resin) than glass fillers having any conventional glass composition, in terms of at least one property selected from refractive index, density, and Young's modulus.

The components in the glass composition A-8 will be described hereinafter.

($SiO_2$)

$SiO_2$ is a component involved in formation of the skeleton of the glass and is a main component (whose content is highest) in the composition A-8. In the composition A-8, $SiO_2$ is a component responsible for adjusting the devitrification temperature and viscosity during glass forming. Further, $SiO_2$ is a component responsible also for improving the water resistance of the glass and adjusting the refractive index of the glass. When the content of $SiO_2$ in the composition A-8 is 60 mass % or more and 80 mass % or less, the devitrification temperature of the glass is prevented from being so high as to make production of the glass filler difficult, and the water resistance of the glass is increased. When the content of $SiO_2$ is in this range, the melting point of the glass cannot be excessively high, and the uniformity of melting of raw materials is improved. Additionally, when the content of $SiO_2$ is in this range, the refractive index of the glass can be controlled within a range suitable for incorporation into acrylic resin. The lower limit of the content of $SiO_2$ may be 62 mass % or more and may be 64 mass % or more, or even more than 65 mass %. The upper limit of the content of $SiO_2$ may be 74 mass % or less and may be 73 mass % or less, 72 mass % or less, less than 71 mass %, or even less than 68 mass %.

($B_2O_3$)

$B_2O_3$ is a component involved in formation of the skeleton of the glass and responsible for adjusting the devitrification temperature and viscosity during glass forming. Further, $B_2O_3$ is a component responsible also for adjusting the refractive index of the glass. When the content of $B_2O_3$ in the composition A-8 is 5 mass % or more and 20 mass % or less, the devitrification temperature of the glass is prevented from being so high as to make production of the glass filler difficult, and the refractive index of the glass can be adjusted within a range suitable for incorporation into acrylic resin. Additionally, the melting point of the glass cannot be excessively high, and the uniformity of melting of raw materials is improved. The lower limit of the content of $B_2O_3$ may be 8 mass % or more and may be 10 mass % or more, 11 mass % or more, 12 mass % or more, 13 mass % or more, or even 14 mass % or more. The upper limit of the content of $B_2O_3$ may be 18 mass % or less and may be 17 mass % or less, 16 mass % or less, or even less than 15 mass %.

($Al_2O_3$)

$Al_2O_3$ is a component involved in formation of the skeleton of the glass and responsible for adjusting the devitrification temperature and viscosity during glass forming. Further, $Al_2O_3$ is a component responsible also for improving the water resistance of the glass and adjusting the refractive index of the glass. When the content of $Al_2O_3$ in the composition A-8 is 5 mass % or more and 15 mass % or less, the devitrification temperature of the glass is prevented from being so high as to make production of the glass filler difficult, and the refractive index of the glass can be adjusted within a range suitable for incorporation into acrylic resin. Additionally, the melting point of the glass cannot be excessively high, and the uniformity of melting of raw materials is improved. The lower limit of the content of $Al_2O_3$ may be 6 mass % or more and may be 6.5 mass % or more, or even 7 mass % or more. The upper limit of the content of $Al_2O_3$ may be 13 mass % or less and may be less than 12 mass %, less than 10 mass %, less than 9 mass %, or even less than 8 mass %.

(MgO and CaO)

The composition A-8 may further include MgO. MgO included in the composition A-8 is a component responsible for adjusting the devitrification temperature and viscosity during glass forming and also for adjusting the refractive index of the glass. Thus, the lower limit of the content of MgO in the composition A-8 may be 0.1 mass % or more. The upper limit of the content of MgO may be less than 1 mass % and may be less than 0.7 mass %, less than 0.5 mass %, or less than 0.3 mass %.

The composition A-8 may further include CaO. CaO included in the composition A-8 is a component responsible for adjusting the devitrification temperature and viscosity during glass forming and also for adjusting the refractive index of the glass. Th addition of CaO and the addition of MgO can exert the same effect. From the viewpoint of reduction in refractive index, the addition of MgO is more advantageous than the addition of CaO. The content of CaO is preferably controlled to be lower than the content of MgO. Thus, the upper limit of the content of CaO in the composition A-8 may be less than 1 mass % and may be less than 0.5 mass %, less than 0.3 mass %, or even less than 0.1 mass %.

When (MgO+CaO) representing the sum of the contents of MgO and CaO is 0.1 mass % or more and less than 1 mass % in the composition A-8, excessive increase in the devitrification temperature of the glass can be prevented, and the devitrification temperature and viscosity of molten glass can be controlled within ranges suitable for production of the glass filler. When (MgO+CaO) is in this range, the refractive index of the glass can be adjusted within a range suitable for incorporation into acrylic resin. The lower limit of (MgO+CaO) may be 0.15 mass % or more. The upper limit of (MgO+CaO) may be less than 0.7 mass % and may be less than 0.5 mass % or even less than 0.3 mass %.

(SrO)

The composition A-8 may further include SrO. SrO included in the composition A-8 is a component responsible for adjusting the devitrification temperature and viscosity during glass forming and also for increasing the refractive index of the glass. Thus, the upper limit of the content of SrO in the composition A-8 may be less than 1 mass % and may be less than 0.5 mass %, less than 0.3 mass %, or even less than 0.1 mass %. The composition A-8 may be substantially free of SrO.

(BaO)

The composition A-8 may further include BaO. BaO included in the composition A-8 is a component responsible for adjusting the devitrification temperature and viscosity during glass forming and also for increasing the refractive index of the glass. Thus, the upper limit of the content of BaO in the composition A-8 may be less than 1 mass % and may be less than 0.5 mass %, less than 0.3 mass %, or even less than 0.1 mass %. The composition A-8 may be substantially free of BaO.

(ZnO)

The composition A-8 may further include ZnO. ZnO included in the composition A-8 is a component responsible for adjusting the devitrification temperature and viscosity during glass forming and also for increasing the refractive index of the glass. Thus, the upper limit of the content of ZnO in the composition A-8 may be less than 1 mass % and may be less than 0.5 mass %, less than 0.3 mass %, or even less than 0.1 mass %. The composition A-8 may be substantially free of ZnO.

($Li_2O$, $Na_2O$, and $K_2O$)

In the composition A-8, alkali metal oxides ($Li_2O$, $Na_2O$, and $K_2O$) are components responsible for adjusting the devitrification temperature and viscosity during glass forming.

The composition A-8 may further include $Li_2O$. The upper limit of the content of $Li_2O$ in the composition A-8 may be 5 mass % or less and may be less than 2 mass %, less than 1 mass %, less than 0.75 mass %, or even less than 0.5 mass %.

When the content of $Na_2O$ in the composition A-8 is more than 9 mass % and less than 13 mass %, excessive increase in the devitrification temperature of the glass can be prevented, and the devitrification temperature and viscosity of molten glass can be controlled within ranges suitable for production of the glass filler. Additionally, the increase in melting point of the glass can be limited to achieve more uniform melting of glass raw materials, and at the same time excessive decrease in glass transition temperature can be avoided to ensure high heat resistance of the glass. The lower limit of the content of $Na_2O$ may be 9.5 mass % or more and may be 10 mass % or more. The upper limit of the content of $Na_2O$ may be 12.5 mass % or less and may be 12 mass % or less.

The composition A-8 may further include $K_2O$. The lower limit of the content of $K_2O$ in the composition A-8 may be 0.1 mass % or more and may be more than 0.5 mass %. The upper limit of the content of $K_2O$ may be 5 mass % or less and may be 3 mass % or less, 2 mass % or less, less than 1 mass %, or even 0.8 mass % or less.

When ($Li_2O+Na_2O+K_2O$) representing the total content of the alkali metal oxides is more than 9 mass % and less than 13 mass % in the composition A-8, excessive increase in the devitrification temperature of the glass can be prevented, and the devitrification temperature and viscosity of molten glass can be controlled within ranges suitable for production of the glass filler. Additionally, the increase in melting point of the glass can be limited to achieve more uniform melting of glass raw materials, and at the same time excessive decrease in glass transition temperature can be avoided to ensure high heat resistance of the glass. The lower limit of ($Li_2O+Na_2O+K_2O$) may be 9.5 mass % or more and may be more than 10 mass %, 10.5 mass % or more, or even more than 11 mass %. The upper limit of ($Li_2O+Na_2O+K_2O$) may be 18 mass % or less and may be less than 15 mass % and less than 13 mass %.

($TiO_2$)

The composition A-8 may further include $TiO_2$. $TiO_2$ included in the composition A-8 is a component responsible for adjusting the devitrification temperature and viscosity during glass forming and also for increasing the refractive index of the glass. Thus, the upper limit of the content of $TiO_2$ in the composition A-8 may be less than 5 mass % and may be less than 2 mass %, less than 1 mass %, or even less than 0.5 mass %. When the content of $TiO_2$ is below such an upper limit, the devitrification temperature of molten glass can be prevented from being so high due to the inclusion of $TiO_2$ that the production of the glass filler is affected. The composition A-8 may be substantially free of $TiO_2$.

($ZrO_2$)

The composition A-8 may further include $ZrO_2$. $ZrO_2$ included in the composition A-8 is a component responsible for adjusting the devitrification temperature and viscosity during glass forming and also for increasing the refractive index of the glass. Thus, the upper limit of the content of $ZrO_2$ in the composition A-8 may be less than 5 mass % and may be less than 2 mass %, less than 1 mass %, or even less than 0.5 mass %. When the content of $ZrO_2$ is below such an upper limit, the devitrification temperature of molten glass can be prevented from being so high due to the inclusion of $ZrO_2$ that the production of the glass filler is affected. The composition A-8 may be substantially free of $ZrO_2$.

(Composition A-9)

In another specific example of the glass composition A, the composition further includes the following components, in mass %:

$50 \leq SiO_2 \leq 75$,
$15 \leq Al_2O_3 \leq 30$,
$5 \leq MgO \leq 25$, and
$0 \leq (Li_2O+Na_2O+K_2O) \leq 4$ (composition A-9).

A glass filler having the glass composition A-9 can have excellent mechanical strength and elastic modulus.

The components in the glass composition A-9 will be described hereinafter.

($SiO_2$)

$SiO_2$ is a component involved in formation of the skeleton of the glass and is a main component (whose content is highest) in the composition A-9. In the composition A-9, $SiO_2$ is a component responsible for adjusting the devitrification temperature and viscosity during glass forming and for improving the water resistance of the glass. Further, in the composition A-9, $SiO_2$ is a component responsible also for improving the mechanical strength of the glass. When the content of $SiO_2$ in the composition A-9 is 50 mass % or more and 75 mass % or less, the devitrification temperature of the glass is prevented from being so high as to make production of the glass filler difficult, and the water resistance of the glass is increased. When the content of $SiO_2$ is in this range, the melting point of the glass cannot be excessively high, and the uniformity of melting of raw materials is improved. Further, when the content of $SiO_2$ is in this range, the mechanical strength of the glass is increased. The lower limit of the content of $SiO_2$ may be 53 mass % or more and may be 55 mass % or more, 57 mass % or more, 58 mass % or more, or even 59 mass % or more. The upper limit of the content of $SiO_2$ may be 70 mass % or less and may be 67 mass % or less, 65 mass % or less, 63 mass % or less, less than 62 mass %, or even 61 mass % or less.

($B_2O_3$)

$B_2O_3$ is a component involved in formation of the skeleton of the glass. $B_2O_3$ is a component responsible also for adjusting the devitrification temperature and viscosity during glass forming. However, the inclusion of excess $B_2O_3$ reduces the water resistance of the glass. When the content of $B_2O_3$ in the composition A-9 is 2 mass % or more and 15 mass % or less, the devitrification temperature of the glass is prevented from being so high as to make production of the glass filler difficult, and the water resistance of the glass is increased. Additionally, the melting point of the glass cannot be excessively high, and the uniformity of melting of raw materials is improved. The lower limit of the content of $B_2O_3$ may be 0.1 mass % or more. The upper limit of the content of $B_2O_3$ may be 5 mass % or less and may be 2 mass % or less, 1.5 mass % or less, 1 mass % or less, 0.5 mass % or less, or even 0.1 mass % or less.

($Al_2O_3$)

$Al_2O_3$ is a component involved in formation of the skeleton of the glass. $Al_2O_3$ is a component responsible also for adjusting the devitrification temperature and viscosity during glass forming and for improving the water resistance of the glass. Further, in the composition A-9, $Al_2O_3$ is a component responsible also for increasing the elastic modulus of the glass. When the content of $Al_2O_3$ in the composition A-9 is 15 mass % or more and 30 mass % or less, the devitrification temperature of the glass is prevented from being so high as to make production of the glass filler difficult, and the water resistance of the glass is increased. Additionally, the melting point of the glass cannot be excessively high, and the uniformity of melting of raw materials is improved. Further, the elastic modulus of the glass is increased. The lower limit of the content of $Al_2O_3$ may be 16 mass % or more and may be 17 mass % or more, or even 18 mass % or more. The upper limit of the content of $Al_2O_3$ may be 25 mass % or less and may be 23 mass % or less, 21 mass % or less, or even less than 20 mass %.

(MgO)

In the composition A-9, MgO is a component responsible for adjusting the devitrification temperature and viscosity during glass forming. In the composition A-9, MgO is a component responsible also for increasing the elastic modulus of the glass. When the content of MgO in the composition A-9 is 5 mass % or more and 25 mass % or less, excessive increase in the devitrification temperature of the glass can be prevented, and the devitrification temperature and the viscosity at melting of the glass can be controlled within ranges suitable for production of the glass filler.

Additionally, the elastic modulus of the glass is increased. The lower limit of the content of MgO may be 8 mass % or more and may be 10 mass % or more, 11 mass % or more, or even more than 12 mass %. The upper limit of the content of MgO may be 22 mass % or less and may be 20 mass % or less, 18 mass % or less, 17 mass % or less, or even 16 mass % or less.

(CaO)

The composition A-9 may further include CaO. CaO included in the composition A-9 is a component responsible for adjusting the devitrification temperature and viscosity during glass forming. The lower limit of the content of CaO in the composition A-9 may be 0.1 mass % or more. The upper limit of the content of CaO may be 20 mass % or less and may be 15 mass % or less, 12 mass % or less, 10 mass % or less, 8 mass % or less, or even less than 6 mass %.

(SrO)

The composition A-9 may further include SrO. SrO included in the composition A-9 is a component responsible for adjusting the devitrification temperature and viscosity during glass forming. The upper limit of the content of SrO in the composition A-10 may be 10 mass % or less and may be 5 mass % or less, 2 mass % or less, or even less than 0.1 mass %. The composition A-9 may be substantially free of SrO.

(BaO)

The composition A-9 may further include BaO. BaO included in the composition A-9 is a component responsible for adjusting the devitrification temperature and viscosity during glass forming. The upper limit of the content of BaO in the composition A-9 may be 10 mass % or less and may be 5 mass % or less, 2 mass % or less, or even less than 0.1 mass %. The composition A-9 may be substantially free of BaO.

(ZnO)

The composition A-9 may further include ZnO. ZnO included in the composition A-9 is a component responsible for adjusting the devitrification temperature and viscosity during glass forming. However, ZnO is prone to evaporation and can be lost into the atmosphere during melting, and the inclusion of excess ZnO therefore increases the evaporation-induced variation in glass component proportions, making difficult control of the glass composition. The upper limit of the content of ZnO in the composition A-9 may be 10 mass % or less and may be 5 mass % or less, 2 mass % or less, or even less than 0.1 mass %. The composition A-9 may be substantially free of ZnO.

($Li_2O$, $Na_2O$, and $K_2O$)

In the composition A-9, alkali metal oxides ($Li_2O$, $Na_2O$, and $K_2O$) are components responsible for adjusting the devitrification temperature and viscosity during glass forming.

When ($Li_2O+Na_2O+K_2O$) representing the total content of the alkali metal oxides is 0 mass % or more and 4 mass % or less in the composition A-9, excessive increase in the devitrification temperature of the glass can be prevented, and the devitrification temperature and viscosity of molten glass can be controlled within ranges suitable for production of the glass filler. Additionally, the increase in the melting point of the glass can be limited to achieve more uniform melting of glass raw materials, and at the same time excessive decrease in the glass transition temperature can be avoided to ensure high heat resistance of the glass The lower limit of ($Li_2O+Na_2O+K_2O$) may be more than 0 mass % and may be 0.1 mass % or more. The upper limit of ($Li_2O+Na_2O+K_2O$) may be 3 mass % or less and may be 2 mass % or less, 1 mass % or less, 0.8 mass % or less, or even 0.5 mass % or less.

($TiO_2$)

The glass composition A-9 may further include $TiO_2$. $TiO_2$ included in the composition A-9 is a component responsible for improving the meltability and chemical durability of the glass and improving the ultraviolet absorption property of the glass. The lower limit of the content of $TiO_2$ in the composition A-9 may be 0 mass % or more and may be 0.1 mass % or more. The upper limit of the content of $TiO_2$ may be 5 mass % or less and may be less than 2 mass %, 1 mass % or less, 0.5 mass % or less, or even 0.2 mass % or less. When the content of $TiO_2$ is below such an upper limit, the devitrification temperature of molten glass can be prevented from being so high due to the inclusion of $TiO_2$ that the production of the glass filler is affected. The composition A-9 may be substantially free of $TiO_2$.

($ZrO_2$)

The glass composition A-9 may further include $ZrO_2$. $ZrO_2$ included in the composition A-9 is a component responsible for adjusting the devitrification temperature and viscosity during glass forming. The upper limit of the content of $ZrO_2$ in the composition A-9 may be 5 mass % or less and may be 2 mass % or less, 1 mass % or less, or even less than 0.1 mass %. When the content of $ZrO_2$ is below such an upper limit, the devitrification temperature of molten glass can be prevented from being so high due to the inclusion of $ZrO_2$ that the production of the glass filler is affected. The composition A-9 may be substantially free of $ZrO_2$.

(Composition A-10)

In another specific example of the glass composition A, the composition further includes the following components, in mass %:

60≤$SiO_2$≤75,
0.1≤(MgO+CaO)≤20,
9≤($Li_2O+Na_2O+K_2O$)≤20, and
5≤$ZrO_2$≤20 (composition A-10).

A glass filler having the glass composition A-10 can have high chemical durability.

The components in the glass composition A-10 will be described hereinafter.

($SiO_2$)

$SiO_2$ is a component involved in formation of the skeleton of the glass and is a main component (whose content is highest) in the composition A-10. In the composition A-10, $SiO_2$ is a component responsible for adjusting the devitrification temperature and viscosity during glass forming and for improving the water resistance and acid resistance of the glass. When the content of $SiO_2$ in the composition A-10 is 60 mass % or more and 75 mass % or less, the devitrification temperature of the glass is prevented from being so high as to make production of the glass filler difficult, and the water resistance and acid resistance of the glass are increased. When the content of $SiO_2$ is in this range, the melting point of the glass cannot be excessively high, and the uniformity of melting of raw materials is improved. The lower limit of the content of $SiO_2$ may be 63 mass % or more and may be 64 mass % or more, more than 65 mass %, or even more than 66 mass %. The upper limit of the content of $SiO_2$ may be 74 mass % or less and may be 73 mass % or less, 71 mass % or less, or even 70 mass % or less.

($B_2O_3$)

The composition A-10 may further include $B_2O_3$. $B_2O_3$ included in the composition A-10 is a component involved in formation of the skeleton of the glass. $B_2O_3$ is a component responsible also for adjusting the devitrification temperature and viscosity during glass forming. However, the inclusion of excess $B_2O_3$ reduces the acid resistance of the glass. The upper limit of the content of $B_2O_3$ may be 5 mass % or less and may be less than 3 mass %, less than 2 mass %, less than 1 mass %, or even 0.5 mass % or less.

($Al_2O_3$)

The composition A-10 may further include $Al_2O_3$. $Al_2O_3$ included in the composition A-10 is a component involved in formation of the skeleton of the glass. $Al_2O_3$ is a component responsible also for adjusting the devitrification temperature and viscosity during glass forming and for improving the water resistance of the glass. However, the inclusion of excess $Al_2O_3$ reduces the acid resistance of the glass. The upper limit of the content of $Al_2O_3$ may be 5 mass % or less and may be 4 mass % or less, less than 3 mass %, less than 2 mass %, or even 1.5 mass % or less.

($B_2O_3+Al_2O_3$)

For the composition A-10, ($B_2O_3+Al_2O_3$) representing the sum of the contents of $B_2O_3$ and $Al_2O_3$ can be important when the ease of formation and acid resistance of the glass filler are given priority. In the composition A-10, ($B_2O_3+Al_2O_3$) may be 5 mass % or less. In this case, the devitrification temperature of the glass is prevented from being so high as to make production of the glass filler difficult, and the acid resistance of the glass is increased. Additionally, the melting point of the glass cannot be excessively high, and the uniformity of melting of raw materials is improved. The upper limit of ($B_2O_3+Al_2O_3$) may be 4 mass % or less and may be less than 3 mass %, less than 2 mass %, or even less than 1.5 mass %.

(MgO and CaO)

The composition A-10 may further include MgO. MgO included in the composition A-10 is a component responsible for adjusting the devitrification temperature and viscosity during glass forming. MgO is a component responsible for adjusting the acid resistance and water resistance of a glass composition. The lower limit of the content of MgO may be 0.1 mass % or more and may be 1 mass % or more, or even more than 2 mass %. The upper limit of the content of MgO may be 15 mass % or less and may be 12 mass % or less, 10 mass % or less, 8 mass % or less, 6 mass % or less, or even 5 mass % or less.

The composition A-10 may further include CaO. CaO included in the composition A-10 is a component responsible for adjusting the devitrification temperature and viscosity during glass forming. CaO is a component responsible for adjusting the acid resistance and water resistance of a glass composition. The lower limit of the content of CaO may be 0.1 mass % or more and may be 1 mass % or more, 2 mass % or more, or even more than 3 mass %. The upper limit of the content of CaO may be 15 mass % or less and may be 12 mass % or less, 10 mass % or less, or even 8 mass % or less.

When (MgO+CaO) representing the sum of the contents of MgO and CaO is 0.1 mass % or more and 20 mass % or less in the composition A-10, excessive increase in the devitrification temperature of the glass can be prevented, and the devitrification temperature and viscosity of molten glass can be controlled within ranges suitable for production of the glass filler. Additionally, when (MgO+CaO) is in such a range, the chemical durability of the glass can also be improved. The lower limit of (MgO+CaO) may be 2 mass % or more and may be 4 mass % or more, 6 mass % or more, 8 mass % or more, or even 9 mass % or more. The upper limit of (MgO+CaO) may be 20 mass % or less and may be 18 mass % or less, 16 mass % or less, less than 14 mass %, or even 13 mass % or less.

(SrO)

The composition A-10 may further include SrO. SrO included in the composition A-10 is a component responsible for adjusting the devitrification temperature and viscosity during glass forming. However, the inclusion of excess SrO reduces the acid resistance of the glass. The upper limit of the content of SrO may be 10 mass % or less and may be 5 mass % or less, less than 2 mass %, or even less than 0.1 mass %. The composition A-10 may be substantially free of SrO.

(BaO)

The composition A-10 may further include BaO. BaO included in the composition A-10 is a component responsible for adjusting the devitrification temperature and viscosity during glass forming. However, the inclusion of excess BaO reduces the acid resistance of the glass. The upper limit of the content of BaO may be 10 mass % or less and may be 5 mass % or less, less than 2 mass %, or even less than 0.1 mass %. The composition A-10 may be substantially free of BaO.

(ZnO)

The composition A-10 may further include ZnO. ZnO included in the composition A-10 is a component responsible for adjusting the devitrification temperature and viscosity during glass forming. However, ZnO is prone to evaporation and can be lost into the atmosphere during melting, and the inclusion of excess ZnO therefore increases the evaporation-induced variation in glass component proportions, making difficult control of the glass composition. The upper limit of the content of ZnO may be 10 mass % or less and may be 5 mass % or less, less than 3 mass %, 1 mass % or less, or even less than 0.1 mass %.

($Li_2O$, $Na_2O$, and $K_2O$)

In the composition A-10, alkali metal oxides ($Li_2O$, $Na_2O$, and $K_2O$) are components responsible for adjusting the devitrification temperature and viscosity during glass forming. The alkali metal oxides ($Li_2O$, $Na_2O$, and $K_2O$) are components responsible also for adjusting the acid resistance and water resistance of the glass.

The composition A-10 may further include $Li_2O$. The lower limit of the content of $Li_2O$ in the composition A-10 may be 0.1 mass % or more and may be 0.5 mass % or more, 1 mass % or more, or 1.5 mass % or more. The upper limit of the content of $Li_2O$ may be 5 mass % or less and may be 4 mass % or less, 3.5 mass % or less, or even 3 mass % or less.

In the composition A-10, the content of $Na_2O$ may be 6 mass % or more and 20 mass % or less. In this case, excessive increase in the devitrification temperature of the glass can be prevented, and the devitrification temperature and viscosity of molten glass can be controlled within ranges suitable for production of the glass filler. Additionally, the increase in the melting point of the glass can be limited to achieve more uniform melting of glass raw materials, and at the same time excessive decrease in the glass transition temperature can be avoided to ensure high heat resistance of the glass. Further, when the content of $Na_2O$ is in the above range, the chemical durability of the glass can also be improved. The lower limit of the content of $Na_2O$ may be 7 mass % or more and may be 7.5 mass % or more, or even 8 mass % or more. The upper limit of the content of $Na_2O$ may be 18 mass % or less and may be 16 mass % or less, 15 mass % or less, 14 mass % or less, less than 13 mass %, or even less than 12 mass %.

The composition A-10 may further include $K_2O$. In the composition A-10, the lower limit of the content of $K_2O$ may be 0.1 mass % or more and may be more than 0.5 mass %. In the composition A-10, the upper limit of the content of $K_2O$ may be 5 mass % or less and may be less than 4 mass %, 3 mass % or less, or even less than 2 mass %.

When ($Li_2O+Na_2O+K_2O$) representing the total content of the alkali metal oxides is 9 mass % or more and 20 mass % or less in the composition A-10, excessive increase in the devitrification temperature of the glass can be prevented, and the devitrification temperature and viscosity of molten glass can be controlled within ranges suitable for production of the glass filler. Additionally, the increase in the melting point of the glass can be limited to achieve more uniform melting of glass raw materials, and at the same time excessive decrease in the glass transition temperature can be avoided to ensure high heat resistance of the glass. Further, when ($Li_2O+Na_2O+K_2O$) is in the above range, the chemical durability of the glass can also be improved. The lower limit of ($Li_2O+Na_2O+K_2O$) may be 9.5 mass % or more and may be 10 mass % or more. The upper limit of ($Li_2O+Na_2O+K_2O$) may be 18 mass % or less and may be 16 mass % or less, 15 mass % or less, 14 mass % or less, less than 13 mass %, or even less than 12 mass %.

($TiO_2$)

The glass composition A-10 may further include $TiO_2$. $TiO_2$ included in the composition A-10 is a component responsible for improving the meltability and chemical durability of the glass. The upper limit of the content of $TiO_2$ in the composition A-10 may be 5 mass % or less and may be less than 2 mass %, less than 1 mass %, less than 0.5 mass %, or even less than 0.1 mass %. The composition A-10 may be substantially free of $TiO_2$.

($ZrO_2$)

In the glass composition A-10, $ZrO_2$ is a component responsible for adjusting the devitrification temperature and viscosity during glass forming. $ZrO_2$ is a component responsible for adjusting the acid resistance and water resistance of a glass composition. When the content of $ZrO_2$ in the composition A-10 is 5 mass % or more and 20 mass % or less, the devitrification temperature of the glass is prevented from being so high as to make production of the glass filler difficult, and the water resistance and acid resistance of the glass are increased. The lower limit of the content of $ZrO_2$ in the composition A-10 is more than 5 mass % and may be 5.5 mass % or more, 6 mass % or more, 6.5 mass % or more, or even 7 mass % or more. The upper limit of the content of $ZrO_2$ may be 18 mass % or less and may be 15 mass % or less, 12 mass % or less, less than 10 mass %, 9.5 mass % or less, 9 mass % or less, 8.5 mass % or less, or even 8 mass % or less.

The glass composition A may further include the following components, in mass %:

45≤$SiO_2$≤65,
21≤$B_2O_3$≤35,
5≤$Al_2O_3$≤15, and
4≤$Na_2O$≤9 (composition A-11).

The glass composition A may further include the following components, in mass %:

45≤$SiO_2$≤70,
10≤$B_2O_3$≤40,
0.1≤$Al_2O_3$≤20,
0.1≤($MgO+CaO$)≤10, and
0≤($Li_2O+Na_2O+K_2O$)≤5 (composition A-12).

The glass composition A may further include components described below, as long as the effect of the present invention is obtained. It should be noted that, among the following components, those already mentioned for the specific glass composition selected from A-1 to A-12 can be present in a content described in the explanation for the specific composition.

(Additional Component)

The glass composition A may include, as an additional component, at least one selected from $P_2O_5$, $La_2O_3$, $WO_3$, $Nb_2O_5$, $Y_2O_3$, $MoO_3$, $Ta_2O_3$, and $Cr_2O_3$, provided that the content of the or each additional component is 0 mass % or more and 1 mass % or less. The glass composition A may be substantially free of the at least one additional component.

The glass composition A may include, as an additive, at least one selected from $SO_3$, F, Cl, $SnO_2$, $CeO_2$, $As_2O_3$, and $Sb_2O_3$, provided that the content of the or each additive is 0 mass % or more and 1 mass % or less. The glass composition A may be substantially free of the at least one additive.

The glass composition A may include at least one substance selected from $H_2O$, OH, $H_2$, $CO_2$, CO, He, Ne, Ar, and $N_2$, provided that the content of the or each substance is 0 mass % or more and 0.1 mass % or less. The glass composition A may be substantially free of these substances.

The glass composition A may include a trace amount of noble metal element. For example, the glass composition A may include at least one noble metal element such as Pt, Rh, Au, and Os, provided that the content of the or each noble metal element is 0 mass % or more and 0.1 mass % or less.

The glass composition A may consist essentially of the components described above. The glass compositions A-1 to A-10 may each consist essentially of the components described above for the composition. In this case, the contents of the components included in the glass composition and the balance between the contents of the components may be such that the contents of the components are within the above numerical ranges including the preferred ranges. The term "consist essentially of" as used herein is intended to mean that impurities such as those derived from glass raw materials, the apparatus for producing a glass composition, and the apparatus for shaping the glass composition may be contained in an amount of less than 0.1%, preferably less than 0.05 mass %, more preferably less than 0.01 mass %, even more preferably less than 0.005 mass %, particularly preferably less than 0.003 mass %, most preferably less than 0.001 mass %.

The glass composition A may be substantially free of CuO. Further, the glass composition A may be substantially free of CoO. The term "substantially free" as used herein means that the content of a substance is less than 0.1%, preferably less than 0.05 mass %, more preferably less than 0.01 mass %, even more preferably less than 0.005 mass %, particularly preferably less than 0.003 mass %, and most preferably less than 0.001 mass %. This term is intended to mean that impurities such as those derived from glass raw materials, the apparatus for producing a glass composition, and the apparatus for shaping the glass composition may be contained.

<Properties>

The properties that the glass filler of the present invention can have will be described hereinafter.

(Light Transmittance)

A visible transmittance as calculated for a thickness of 15 μm of the glass filler is, for example, 87% or more and may, depending on the details of the glass composition A, be 88% or more, 89% or more, 90% or more, or even 90.5% or more. The upper limit of the visible transmittance may be 95% or less and may be 93% or less, 92% or less, or 91.5% or less. Illuminant A can be used as a light source for evaluation of the visible transmittance.

(Melting Properties)

The temperature at which the viscosity of molten glass reaches 1000 dPa·sec (1000 poise) is called "working temperature" of the glass and is the most appropriate temperature for forming of the glass. When the glass filler is produced in the form of glass flakes or glass fibers, a working temperature of 1100° C. or higher of the glass can lead to reduced variation in the thickness of the glass flakes or the diameter of the glass fibers. A working temperature of 1500° C. or lower can lead to reduced fuel cost in melting of the glass and also to reduced likelihood of thermal corrosion of the glass production apparatus and hence lengthened life of the apparatus. The lower limit of the working temperature of the glass composition A may be 1100° C. or higher and may be 1150° C. or higher, or 1160° C. or higher. The upper limit of the working temperature of the glass composition A may be 1500° C. or lower and may be 1450° C. or lower, 1400° C. or lower, 1350° C. or lower, 1300° C. or lower, 1288° C. or lower, 1280° C. or lower, or 1250° C. or lower.

With an increase in the temperature difference ΔT calculated by subtracting the devitrification temperature from the working temperature, the occurrence of devitrification during glass forming is reduced, so that homogeneous glass can be produced in a high yield. Therefore, ΔT of the glass composition A is preferably 0° C. or more, more preferably 25° C. or more, even more preferably 50° C. or more, particularly preferably 100° C. or more, and most preferably 150° C. or more. The ΔT of 500° C. or less can make the adjustment of the glass composition easy. ΔT of the glass composition A may be 500° C. or less and may be 400° C. or less, 300° C. or less, or even 200° C. or less.

(Glass Transition Temperature)

With an increase in the glass transition temperature (glass-transition point, Tg) of the glass composition forming a glass filler, the filler has higher heat resistance and become more resistant to deformation caused by a process involving heating at high temperature. When the glass transition temperature is 500° C. or higher, the glass filler is less likely to undergo a change in shape during a process in which a coating containing a metal or a metal oxide as a main component is formed on the surface of the glass filler. Additionally, the glass filler or coated glass filler can be suitably incorporated in a paint for use in applications such as baking finishing. The lower limit of the glass transition temperature of the glass composition A may be 500° C. or higher and may be 520° C. or higher, 540° C. or higher, 549° C. or higher, or even 550° C. or higher. The upper limit of the glass transition temperature of 900° C. or lower makes the adjustment of the glass composition easy. The upper limit of the glass transition temperature of the glass composition A may be 900° C. or lower and may be 850° C. or lower, 800° C. or lower, or even 750° C. or lower.

(Chemical Durability)

One property relevant to the chemical durability is acid resistance. An index of the acid resistance is a weight decrease ΔW induced by immersion of the glass filler in an acidic aqueous solution. The weight decrease ΔW is determined as follows: raw glass for forming the glass filler is crushed; from the crushed pieces, a certain size of glass powder particles that pass through an auxiliary 710-μm mesh sieve and a standard 590-μm mesh sieve as specified in JIS Z 8801 but fail to pass through a standard 420-μm mesh sieve as specified in JIS Z 8801 are weighed in grams equivalent to the specific gravity of the glass; and the weighed glass powder is immersed in a given amount of an aqueous acid solution having a given temperature and concentration for a given period of time. A smaller weight decrease ΔW indicates higher acid resistance of the glass filler. This measurement method of the weight decrease ΔW is in accordance with the Japan Optical Glass Industrial Standard (JOGIS) 06-1975 "Measurement Method (Powder Method) for Chemical Durability of Optical Glass". It should be noted that in the present specification including examples described later, a 10 mass % aqueous sulfuric acid solution is used in place of a 0.01 N (mol/L) aqueous nitric acid solution as used in the JOGIS measurement method. The temperature of the aqueous sulfuric acid solution is 80° C., and the amount of the solution is 100 mL instead of 80 mL as specified in the JOGIS. Further, the immersion time is 72 hours instead of 60 minutes as specified in the JOGIS. The raw glass used can be a glass sample prepared by melting common glass raw materials so as to achieve a glass composition identical to that of the glass filler to be evaluated. When, for example, a paint or the like containing the glass filler is used in an anti-corrosion lining under acidic environments, the weight decrease ΔW is desirably small. A large weight decrease ΔW leads to deterioration of the anti-corrosion property of the anti-corrosion lining under acidic environments. The upper limit of the weight decrease ΔW of the glass composition A may be 1.5 mass % or less and may be 0.8 mass % or less, or 0.4 mass % or less. The lower limit of the weight decrease ΔW of the glass composition A is typically about 0.05 mass % and may be 0.08 mass % or more, or even 0.1 mass % or more.

For the water resistance, the amount of alkali dissolution can be used as an index. A smaller amount of alkali dissolution indicates higher water resistance of the glass filler. When the glass filler is dispersed in a resin matrix, the amount of alkali dissolution of the glass composition forming the glass filler may be 0.4 mg or less in order to prevent the strength decrease of the resulting resin composition. The upper limit of the amount of alkali dissolution of the glass composition A may be 0.4 mg or less, 0.35 mg or less, 0.3 mg or less, or 0.26 mg or less. The lower limit of the amount of alkali dissolution of the glass composition A is typically about 0.001 mg and may be 0.01 mg or more, or 0.06 mg or more.

[Method for Producing Glass Filler]

The method for producing the glass filler of the present invention is not particularly limited. A known method and apparatus can be used to produce the glass filler of the present invention.

Figure 2:
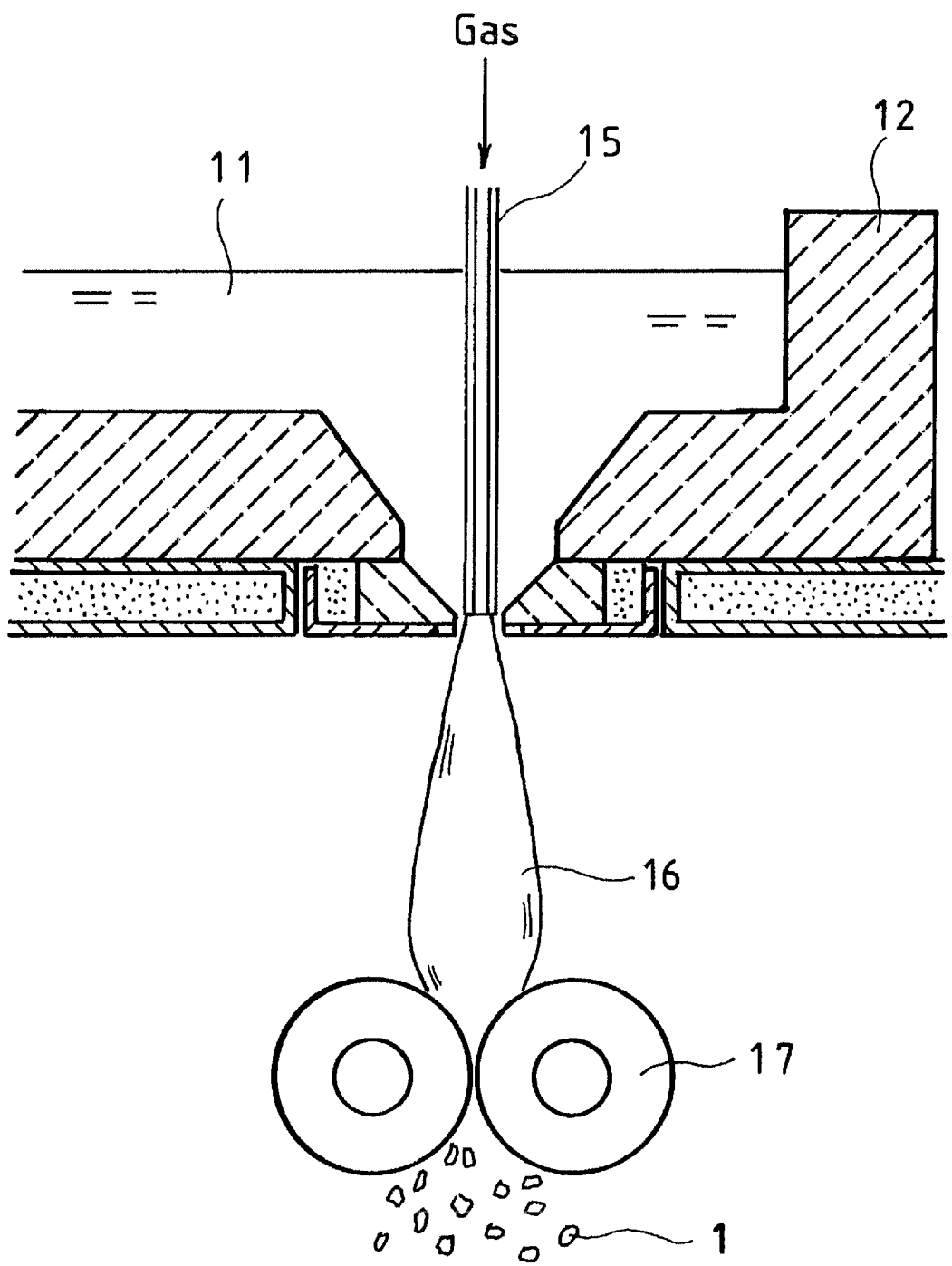
FIG. 2 is a schematic diagram for illustrating an exemplary apparatus and method for producing glass flakes.

Glass flakes 1 can be produced, for example, by using an apparatus as shown in FIG. 2. In the apparatus shown in FIG. 2, raw glass 11 having been melted in a refractory furnace 12 is expanded into a balloon by a gas delivered into a blow nozzle 15, and thus a hollow glass body 16 is formed. The hollow glass body 16 is then crushed by pressure rolls 17 to give the glass flakes 1.

Figure 3:
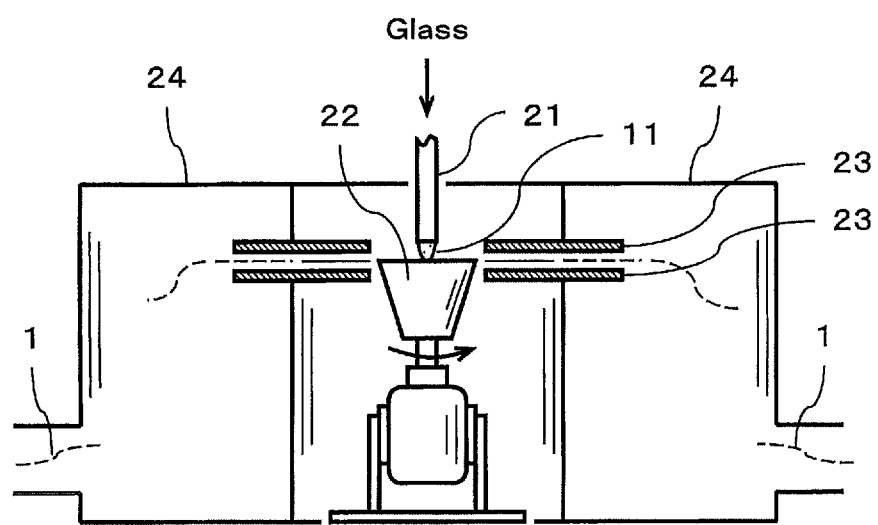
FIG. 3 is a schematic diagram for illustrating another exemplary apparatus and method for producing glass flakes.

The glass flakes 1 can also be produced, for example, by an apparatus as shown in FIG. 3. In the apparatus shown in FIG. 3, molten raw glass 11 is poured into a rotating cup 22 through a nozzle 21, and a centrifugal force generated by rotation of the rotating cup causes the molten raw glass to flow out from the upper edge of the cup 22. The raw glass 11, having flowed out of the cup 22, is drawn by an air stream and introduced into an annular cyclone collector 24 through upper and lower annular plates 23. The glass cools and solidifies into a thin film while passing through the annular plates 23, and the thin film is crushed into fines pieces, which are obtained as the glass flakes 1.

Figure 4:
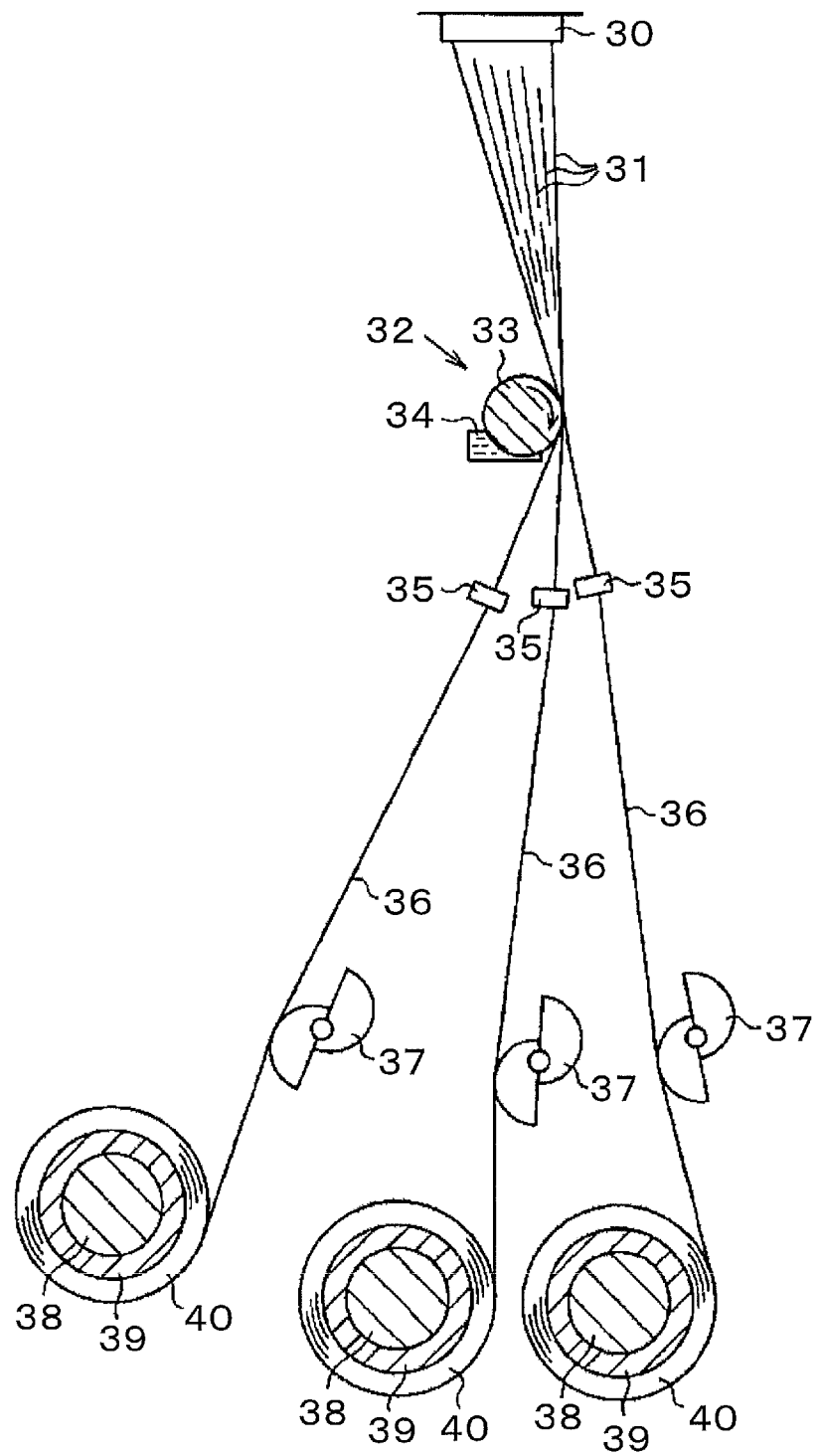
FIG. 4 is a schematic diagram for illustrating an exemplary strand formation apparatus that can be used for production of chopped strands.
Figure 5:
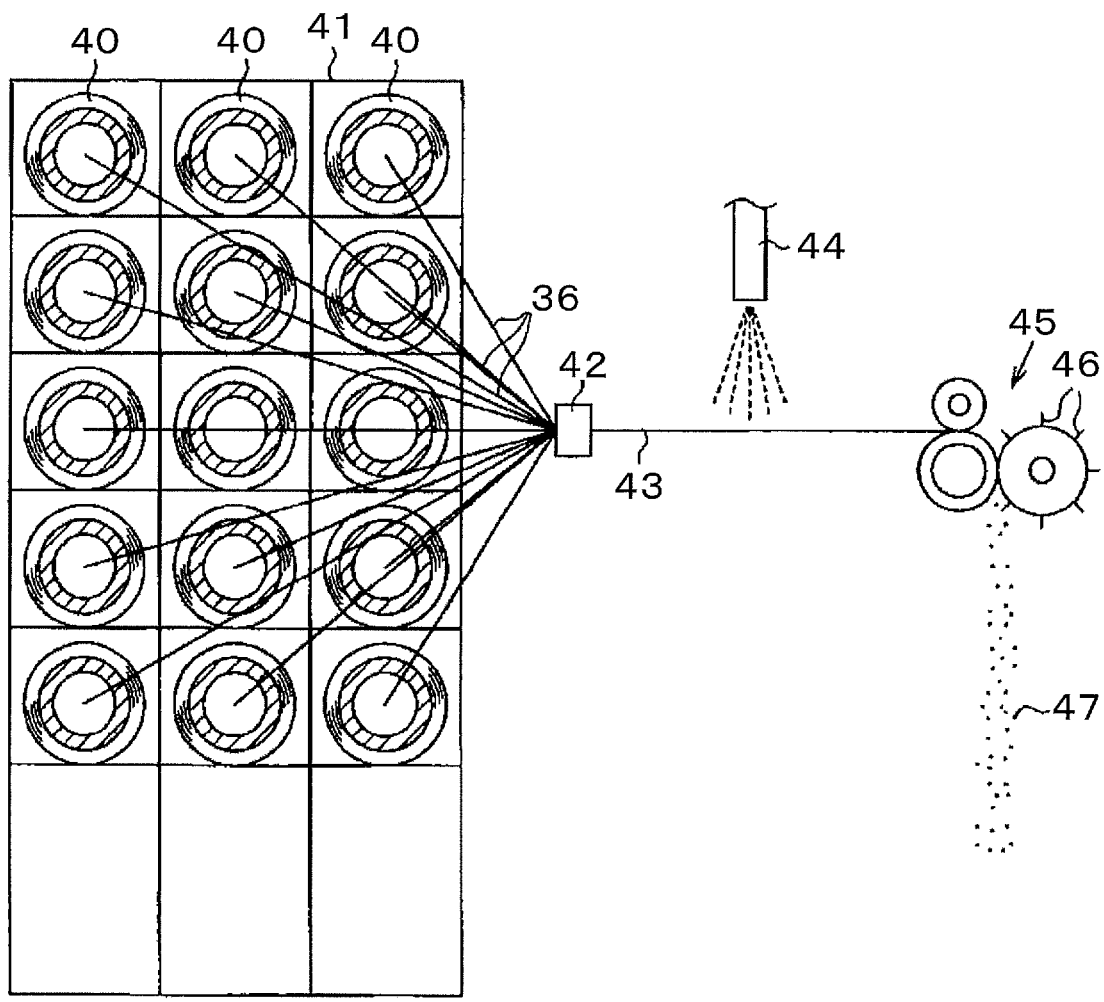
FIG. 5 is a schematic diagram for illustrating an exemplary apparatus for producing chopped strands from a wound strand obtained by the strand formation apparatus shown in FIG. 4.

Chopped strands can be produced, for example, by using apparatuses as shown in FIG. 4 and FIG. 5. First, as shown in FIG. 4, raw glass with a given composition, which has been melted in a refractory furnace, is drawn through a bushing 30 having a large number of nozzles (e.g., 2400 nozzles) to form a large number of glass filaments 31. Cooling water is sprayed on the glass filaments 31, to which a binder (sizing agent) 34 is then applied by an application roller 33 of a binder applicator 32. The large number of glass filaments 31 with the applied binder 34 are bundled into strands 36 through reinforcing pads 35, the strands 36 each being composed of, for example, about 800 glass filaments 31. While being traversed by a traverse finger 37, each strand 36 is wound on a cylindrical tube 39 mounted on a collet 38. The cylindrical tube 39 with the wound strand 36 is detached from the collet 38 to obtain a cake (wound strand body) 40.

Next, as shown in FIG. 5, the cakes 40 are placed in creels 41, and the strands 36 are drawn from the cakes 40 and bundled into a strand bundle 43 through a bundling guide 42. This strand bundle 43 is sprayed with water or a treating liquid using a spray device. Further, the strand bundle 43 is cut by a rotating blade 46 of a cutting device 45 to give chopped strands 47.

Milled fibers can be produced according to a known method.

A glass powder can be produced by crushing glass. The glass powder can be produced according to a known method.

Glass beads can be produced by forming a glass composition into a spherical or nearly spherical shape. The glass beads can be produced according to a known method.

The raw glass 11 has the glass composition A. For the iron oxide in the composition of the glass, the content of FeO, the content of T-$Fe_2O_3$, and $Fe^{2+}/(Fe^{2+}+Fe^{3+})$ are controlled. That is, the content and oxidation-reduction state of the iron oxide are controlled. Thus, the method for producing the glass filler of the present invention includes the step of controlling the content of FeO, the content of T-$Fe_2O_3$, and $Fe^{2+}/(Fe^{2+}+Fe^{3+})$ for the iron oxide in the composition of the glass. This results in a glass filler having a high visible transmittance and a controlled color (glass filler having a desired color).

The control of the content and oxidation-reduction state of iron oxide in the raw glass 11 can be accomplished, for example, by controlling glass raw materials when mixing the glass raw materials to form the raw glass 11, in particular by controlling the types and amounts of the glass raw materials. In a more specific example, the control of the content and oxidation-reduction state of the iron oxide can be accomplished by adding a reductant and/or oxidant when mixing glass raw materials to form the molten raw glass 11. In this example, the content of T-$Fe_2O_3$, the content of FeO, and $Fe^{2+}/(Fe^{2+}+Fe^{3+})$ in the glass composition can be controlled by selecting and controlling the type and amount of the raw material to be converted to iron oxide in the glass and by controlling the type and amount of the reductant and/or oxidant to be added. The reductant is, for example, a carbon-based reductant such as carbon and may be sugar or tin oxide. The oxidant is, for example, a sulfuric acid salt such as sodium sulfate or calcium sulfate or a nitric acid salt such as sodium nitrate or potassium nitrate.

In another specific example, the control of the oxidation-reduction state of iron oxide can be accomplished by controlling a formation temperature and formation atmosphere where the glass filler is formed. The formation temperature is, for example, the temperature of the atmosphere with which the molten raw glass 11 shown in FIGS. 2 and 3 is in contact until it is finally processed into a glass filler. The formation atmosphere is, for example, the atmosphere with which the molten raw glass 11 shown in FIGS. 2 and 3 is in contact until it is finally processed into a glass filler. An atmosphere that allows iron in the molten raw glass to undergo oxidation is an oxidizing atmosphere, an example of which is an atmosphere containing an oxidizing gas such as air or oxygen gas. An atmosphere that allows iron in the molten raw glass to undergo reduction is a reducing atmosphere or an inert atmosphere. The reducing atmosphere is, for example, an atmosphere of a reducing gas such as a mixed gas containing hydrogen, and the inert atmosphere is, for example, an atmosphere of an inert gas such as nitrogen gas, helium gas, or argon gas. A reductant and/or oxidant may be used in conjunction with control of the formation atmosphere where the glass filler is formed.

The control of the content and oxidation-reduction state of iron oxide in the glass composition A and the raw glass 11 can be carried out also in the method for producing the coated glass filler of the present invention, as seen from the fact that this method uses the glass filler of the present invention as a base material.

[Coated Glass Filler]

Figure 6:
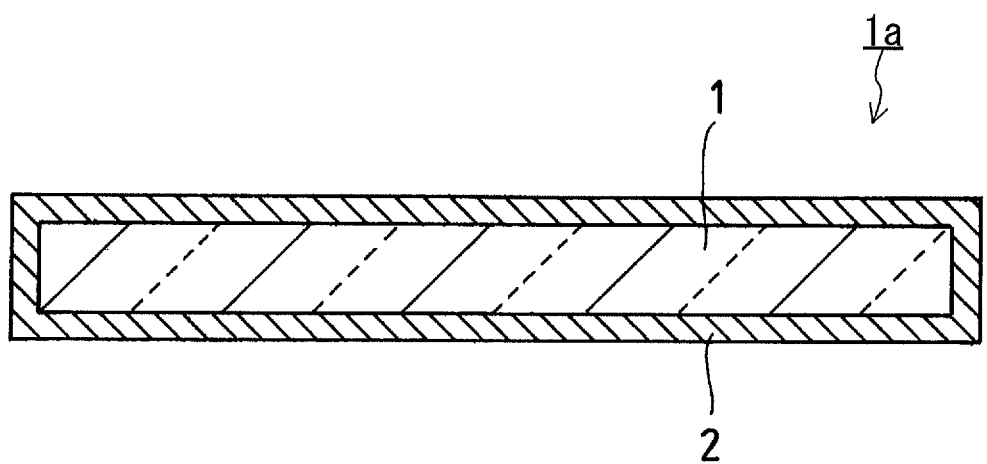
FIG. 6 is a cross-sectional view schematically showing an exemplary coated glass flake which is a type of the coated glass filler of the present invention.

FIG. 6 shows an exemplary coated glass flake 1a which is a type of the coated glass filler of the present invention. In the coated glass flake 1a, the glass flake 1 of the present invention is used as a base material, and a coating 2 is formed on the surface of the glass flake 1. The coating 2 contains a metal or a metal oxide as a main component. The coating 2 may consist essentially of a metal or a metal oxide or may consist of a metal or a metal oxide. The coating 2 may be a single-layer coating, a composite coating, or a multi-layer coating.

The metal forming the coating 2 is not limited and is, for example, at least one selected from silver, gold, platinum, palladium, and nickel.

The metal oxide forming the coating 2 is not limited and is, for example, at least one selected from titanium oxide, aluminum oxide, iron oxide, cobalt oxide, zirconium oxide, zinc oxide, tin oxide, and silicon dioxide. Preferred among these are titanium oxide which allows formation of the coating 2 having high refractive index and high transparency and exhibiting a good interference color, and iron oxide which allows formation of the coating 2 exhibiting a characteristic interference color.

An example of the coating 2 in the form of a multi-layer coating is a coating 2 including a first layer containing a metal as a main component and a second layer containing a metal oxide as a main component.

It suffices for the coating 2 to be formed on at least a portion of the surface of the glass filler serving as a base material. The coating 2 may be formed over the entire surface of the glass filler.

The thickness of the coating 2 can be chosen as appropriate depending on the purpose of the coated glass filler.

The method for forming the coating 2 on the surface of the glass filler is not limited, and a known thin film formation technique can be used. Examples of the method include sputtering, sol-gel process, chemical vapor deposition (CVD), and liquid-phase deposition (LPD). In the LPD, a metal or a metal oxide is deposited from a reaction solution to form a coating on the surface of the base material. The reaction solution is, for example, a solution containing a metal salt.

The coated glass filler of the present invention exhibits a color derived from the high visible transmittance and controlled color of the base material, i.e., of the glass filler of the present invention, and from the configuration of the coating 2. The color of the coated glass filler of the present invention can be affected not only by reflected light from the glass filler serving as the base material but also by transmitted light through the glass filler.

The coated glass filler of the present invention exhibits a color such as metallic color or interference color derived from the coating 2 and can therefore be used also as a bright pigment.

[Incorporation of Glass Filler into Various Compositions Such as Resin Composition, Paint, Ink Composition, and Cosmetic]

The applications of the glass filler of the present invention and the coated glass filler of the present invention are not limited (the glass filler and coated glass filler will be collectively referred to as "glass filler" hereinafter, unless otherwise stated). The glass filler of the present invention can be used as a pigment and/or a reinforcing filler. More specifically, the glass filler of the present invention can be incorporated as a pigment and/or a reinforcing filler, for example, into a composition such as a resin composition, a paint, an ink composition, or a cosmetic. The inclusion of the glass filler of the present invention offers benefits such as improvements in color and gloss and increases in dimensional accuracy and strength of the composition.

Specifically, the incorporation of the glass filler of the present invention into a resin composition can result in, for example, a resin molded product with improved mechanical properties such as high dimensional accuracy and strength. The incorporation of the glass filler of the present invention into a paint can provide improvement in mechanical properties of a paint film or impart a color, gloss, metallic color, or interference color to the paint film. The incorporation of the glass filler of the present invention into an ink composition can impart a color, gloss, metallic color, or interference color to images, geometrical figures, and letters formed by the composition. The incorporation of the glass filler of the present invention into a cosmetic can impart a color and gloss to the cosmetic applied, for example, to the face.

Figure 7:
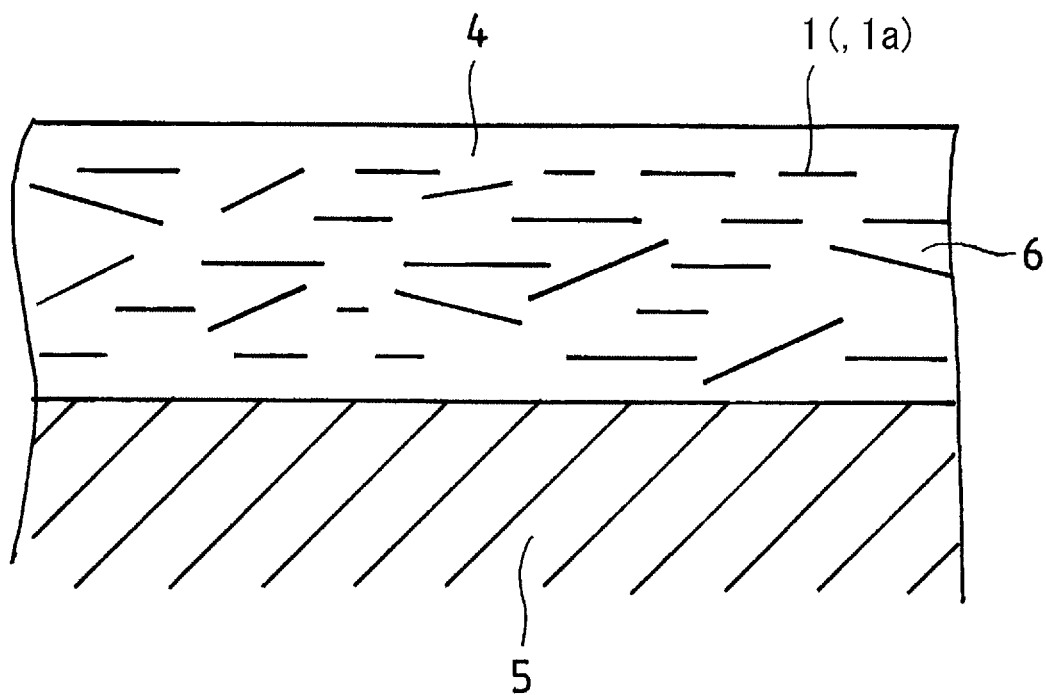
FIG. 7 is a cross-sectional view schematically showing an exemplary use of glass flakes which are a type of the glass filler of the present invention.

FIG. 7 shows an example where a paint incorporating the glass filler of the present invention is applied to a surface of an object 5. A paint film 6 formed on the surface of the object 5 as a result of application and drying of the paint has a resin matrix 4, in which the glass flakes 1 (or the coated glass flakes 1a) which are a type of the glass filler of the present invention are dispersed. The glass flakes 1 can act to improve the color tone and gloss of the paint film 6 and enhance the mechanical properties of the paint film 6.

The type and constitution of the composition into which the glass filler of the present invention is incorporated are not limited, and the composition may be of a known type with known constitution. More specifically, the type and constitution of a resin composition, a paint, an ink composition, and a cosmetic into which the glass filler of the present invention is incorporated are not limited, and they may be of a known type with known constitution. The mixing ratio between the glass filler and these products is not limited and can be chosen as appropriate. The method for mixing the glass filler and these products is not limited either, and a known method can be used.

The paint incorporating the glass filler of the present invention may further include a matrix resin and may further include at least one selected from a thermosetting resin, a thermoplastic resin, and a curing agent.

Examples of the thermosetting resin include acrylic resin, polyester resin, epoxy resin, phenolic resin, urea resin, fluorine resin, polyester-urethane curable resin, epoxy-polyester curable resin, acrylic-polyester resin, acrylic-urethane curable resin, acrylic-melamine curable resin, and polyester-melamine curable resin.

Examples of the thermoplastic resin include polyethylene resin, polypropylene resin, petroleum resin, thermoplastic polyester resin, and thermoplastic fluorine resin.

Examples of the curing agent include polyisocyanate, amine, polyamide, polybasic acid, acid anhydride, polysulfide, trifluoroborate, acid dihydrazide, and imidazole.

The paint incorporating the glass filler of the present invention may, if necessary, further include a material other than those described above.

The resin composition incorporating the glass filler of the present invention further includes a matrix resin. The matrix resin is, for example, any of various thermosetting resins and thermoplastic resins and may be a thermosetting resin or thermoplastic resin as mentioned above for the paint film.

The resin composition incorporating the glass filler of the present invention may, if necessary, further include a material other than those described above.

The type of the ink composition incorporating the glass filler of the present invention is not limited, and the ink composition is, for example, an ink composition for various writing instruments such as ballpoint pens and felt-tipped pens or an ink composition for printing such as a gravure ink or an offset ink.

The ink composition incorporating the glass filler of the present invention further includes a vehicle. The vehicle serves to disperse a pigment and/or dye in the ink composition and fixedly attach the ink composition to paper. The vehicle is composed of, for example, a resin, an oil, and a solvent.

The vehicle of the ink composition for writing instruments includes a resin, examples of which include acrylic resin, styrene-acrylic copolymer, polyvinyl alcohol, polyacrylic acid salt, acrylic-vinyl acetate copolymer, microbially-produced polysaccharides such as xanthan gum, and water-soluble plant-derived polysaccharides such as guar gum. The vehicle may further include a solvent, examples of which include water, an alcohol, a hydrocarbon, and an ester.

The vehicle for the gravure ink includes a resin, examples of which include resins or resin mixture such as gum rosin, wood rosin, tall oil rosin, lime rosin, rosin ester, maleic acid resin, polyamide resin, vinyl resin, nitrocellulose, cellulose acetate, ethyl cellulose, chlorinated rubber, cyclized rubber, ethylene-vinyl acetate copolymer, urethane resin, polyester resin, alkyd resin, gilsonite, dammar, and shellac, mixtures of these resins or resin mixtures, and water-soluble resins or aqueous emulsions prepared by rendering these resins or resin mixtures water-soluble. The vehicle may further include a solvent, examples of which include a hydrocarbon, an alcohol, an ether, an ester, and water.

The vehicle for the offset ink includes a resin, examples of which include rosin-modified phenolic resin, petroleum resin, alkyd resin, and dry modified resins derived from these resins. The vehicle may further include an oil, examples of which include vegetable oils such as linseed oil, tung oil, and soybean oil. The vehicle may further include a solvent, examples of which include n-paraffin, isoparaffin, Aromatic, naphthene, α-olefin, and water.

The ink composition may, if necessary, further contain an additive such as a dye, a pigment, a surfactant, a lubricant, an anti-foaming agent, or a leveling agent and may, if necessary, further contain a material other than those described above.

The type of the cosmetic incorporating the glass filler of the present invention is not limited, and examples of the cosmetic include a wide variety of cosmetics such as facial cosmetics, make-up cosmetics, and hair cosmetics. In particular, the glass filler of the present invention is suitable for use in make-up cosmetics such as foundation, facial powder, eyeshadow, brusher, makeup foundation, nail enamel, eyeliner, mascara, lipstick, and fancy powder.

When the glass filler is incorporated in a cosmetic, the glass filler may be subjected to hydrophobization depending on the purpose of the cosmetic. Examples of the method for the hydrophobization include the following five treatments.

(1) Treatment with a silicone compound such as methyl hydrogen polysiloxane, high-viscosity silicone oil, or silicone resin.

(2) Treatment with a surfactant such as an anionic surfactant or a cationic surfactant.

(3) Treatment with a polymer compound such as nylon, polymethyl methacrylate, polyethylene, a fluorine resin (e.g., polytetrafluoroethylene (PTFE), tetrafluoroethylene-perfluoroalkyl vinyl ether copolymer (PFA), tetrafluoroethylene-hexafluoropropylene copolymer (FEP), tetrafluoroethylene-ethylene copolymer (ETFE), polyvinylidene fluoride (PVDF), polychlorotrifluoroethylene (PCTFE)), or polyamino acid.

(4) Treatment with a perfluoro group-containing compound, lecithin, collagen, a metallic soap, a lipophilic wax, or a partial or full ester of a polyol.

(5) Treatment with any combination of the treatments (1) to (4).

In addition to these treatments (1) to (5), any method applicable to hydrophobization of powders can be used.

A cosmetic incorporating the glass filler may, if necessary, further contain materials commonly used for cosmetics. Examples of the materials include an inorganic powder, an organic powder, a pigment, a colorant, a hydrocarbon, an ester, an oily component, an organic solvent, a resin, a plasticizer, an ultraviolet absorber, an antioxidant, a preservative, a surfactant, a moisturizer, a flavor, water, an alcohol, and a thickener.

Examples of the inorganic powder include talc, kaolin, sericite, white mica, brown mica, red mica, black mica, lepidolite, vermiculite, magnesium carbonate, calcium carbonate, diatomite, magnesium silicate, calcium silicate, aluminum silicate, barium sulfate, metal tungstate, silica, hydroxyapatite, zeolite, boron nitride, and ceramic powder.

Examples of the organic powder include nylon powder, polyethylene powder, polystyrene powder, benzoguanamine powder, polytetrafluoroethylene powder, distyrenebenzene polymer powder, epoxy powder, acrylic powder, and microcrystalline cellulose.

Pigments can be broadly classified into inorganic pigments and organic pigments.

Examples of the inorganic pigments are listed below according to the color.

Inorganic white pigment: Titanium oxide and zinc oxide
Inorganic red pigment: Iron oxide (colcothar) and iron titanate
Inorganic brown pigment: γ-iron oxide
Inorganic yellow pigment: Yellow iron oxide and ocher
Inorganic black pigment: Black iron oxide and carbon black
Inorganic purple pigment: Mango violet and cobalt violet
Inorganic green pigment: Cobalt titanate
Inorganic blue pigment: Ultramarine blue and Prussian blue Inorganic pigments include pearl pigments and metal powder pigments. Examples of the pearl pigments include titanium oxide-coated mica, titanium oxide-coated bismuth oxychloride, bismuth oxychloride, titanium oxide-coated talc, fish scale flake, and colored titanium oxide-coated mica. Examples of the metal powder pigments include aluminum powder and copper powder.

Examples of the organic pigments include Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404.

Another example of the organic pigments is a lake pigment produced by a reaction between an extender pigment such as talc, calcium carbonate, barium sulfate, zirconium oxide, or aluminum white and a dye such as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, or Blue No. 1.

Examples of the colorant include natural colorants such as chlorophyll and ß-carotene.

Examples of the hydrocarbon include squalane, liquid paraffin, vaseline, microcrystalline wax, ozokerite, ceresin, myristic acid, palmitic acid, stearic acid, oleic acid, isostearic acid, cetyl alcohol, hexadecyl alcohol, oleyl alcohol, cetyl 2-ethylhexanoate, 2-ethylhexyl palmitate, 2-octyldodecyl myristate, neopentyl glycol di-2-ethylhexanoate, glycerol tri-2-ethylhexanoate, 2-octyldodecyl oleate, isopropyl myristate, glycerol triisostearate, glycerol tricocoate, olive oil, avocado oil, beeswax, myristyl myristate, mink oil, and lanolin.

Examples of the oily component include silicone oil, higher fatty acids, esters such as fats and oils, higher alcohols, and waxes. Examples of the organic solvent include acetone, toluene, butyl acetate, and acetate esters. Examples of the plasticizer include resins such as alkyd resin and urea resin, camphor, and acetyl tributyl citrate.

The form of the cosmetic is not particularly limited. For example, the cosmetic may be in the form of a powder, a cake, a pencil, a stick, an ointment, a liquid, a milky liquid, or a cream.

EXAMPLES

Hereinafter, the present invention will be described in more detail by Examples and Comparative Examples. The present invention is not limited to Examples described below.

Examples 1 to 58 and Comparative Examples 1 to 4

Glass raw materials were blended to give glass compositions shown in Tables 1 to 11, and a glass raw material batch was prepared for each of Examples and Comparative Examples. The raw materials used were silica sand, boron oxide, aluminum oxide, magnesium oxide, calcium carbonate, zinc oxide, lithium carbonate, sodium carbonate, potassium carbonate, titanium oxide, zirconium oxide, ferric oxide, calcium fluoride, and carbon. Carbon was added as a reductant to the raw material batches so as to achieve iron oxide oxidation-reduction states shown in Tables 1 to 11. The amounts of carbon added to the raw material batches are shown as "Amount of added carbon" in Tables 1 to 11. Next, each raw material batch was melted by heating it to a melting temperature of 1500 to 1580° C. using an electric furnace, and the molten glass was left for a melting time of 0.5 to 4 hours until the composition of the molten glass became uniform. After that, part of the molten glass was poured onto an iron plate, and the poured glass was slowly cooled to an ordinary temperature in an electric furnace. Thus, a glass composition (sheet-shaped product) was obtained as a bulk.

The sheet-shaped products (samples) thus produced in Examples and Comparative Examples were measured for their thermal expansion coefficient using a commercially-available dilatometer (thermomechanical analyzer manufactured by Rigaku Corporation, TMA 8510), and the glass transition temperature of each glass composition was determined from the obtained thermal expansion curve. For each sample, the relationship between viscosity and temperature was examined based on a common platinum ball-drawing method, and the working temperature of the glass composition was determined from the result of the examination. The platinum ball-drawing method is a method that measures the viscosity of molten glass by dipping a platinum ball in the molten glass, drawing the platinum ball upward at a uniform velocity, determining the relationship between the load (friction) during the drawing of the platinum ball and the gravity or buoyancy acting on the platinum ball, and applying the determined relationship to the Stokes' law which states the relationship between the viscosity of a fluid and the fall velocity at which a small particle settles down in the fluid.

Besides the above procedure, the sample prepared was crushed, and a certain size of glass pieces that passed through a standard 1.0-mm mesh sieve as specified in JIS Z 8801 but failed to pass through a standard 2.8-mm mesh sieve as specified in JIS Z 8801 were put into a platinum boat. The glass in the boat was heated by an electric furnace with a temperature gradient (900 to 1400° C.) for 2 hours, and the devitrification temperature of the glass composition was determined as the maximum temperature at a location inside the electric furnace where a crystal appeared in the glass. In order to compensate for variation in temperature behavior from site to site in the electric furnace, the temperature behavior was measured beforehand at given sites in the electric furnace, and the sample was placed at the given sites to measure the devitrification temperature of the sample.

The weight decrease $\Delta W$, as previously described, is an index of the acid resistance. The weight decrease $\Delta W$ was determined as follows: the prepared sample was crushed; from the crushed pieces, a certain size of glass powder particles that passed through an auxiliary 710-μm mesh sieve and a standard 590-μm mesh sieve as specified in JIS Z 8801 but failed to pass through a standard 420-μm mesh sieve as specified in JIS Z 8801 were weighed in grams equivalent to the specific gravity of the glass; and the weighed glass powder was immersed in 100 mL of an aqueous sulfuric acid solution having a temperature of 80° C. and a concentration of 10 mass % for 72 hours. A smaller weight decrease $\Delta W$ indicates higher acid resistance of the glass filler.

The measurement of the amount of alkali dissolution was conducted by a method according to Japanese Industrial Standard (JIS) R 3502-1995 "Test method of glass apparatus for chemical analysis". The prepared sample was crushed to obtain a glass powder, which was sieved through standard mesh sieves as specified in JIS Z 8801. Glass powder particles that passed through a standard mesh sieve with an opening size of 420 μm but were retained on a standard mesh sieve with an opening size of 250 μm were weighed in grams equivalent to the specific gravity of glass. The weighed glass powder was immersed in 50 mL of distilled water at 100° C. for 1 hour, after which alkaline components in the aqueous solution were titrated with 0.01 N sulfuric acid. The milliliters of 0.01 N sulfuric acid consumed for the titration were multiplied by 0.31 to determine the milligrams of the alkaline components calculated as $Na_2O$. The determined milligrams were adopted as the amount of alkali dissolution. The smaller the amount of alkali dissolution is, the higher the water resistance of the glass composition is.

The FeO content, T-$Fe_2O_3$ content, and $Fe^{2+}/(Fe^{2+}+Fe^{3+})$ of the glass composition were determined by the o-phenanthroline spectrophotometric method previously described.

Next, the sheet-shaped product produced was processed to a thickness of 1 mm, and both surfaces of the sheet-shaped product were mirror-polished to obtain a sample for evaluation of light transmittance. For each of the samples thus prepared in Examples and Comparative Examples, the light transmittances $T_{750nm}$, $T_{550nm}$, and $T_{350nm}$ at wavelengths of 750 nm, 550 nm, and 350 nm were determined using a spectrophotometer (manufactured by Shimadzu Corporation, UV 3100PC).

Next, glass flakes were produced from each of the glass compositions of Examples 1 to 58 and Comparative Examples 1 to 4. Specifically, the glass compositions of Examples 1 to 58 and Comparative Examples 1 to 4 were each placed in an production apparatus as shown in FIG. 2, and glass flakes having an average thickness t of 0.5 μm, 1 μm, or 5 μm were produced. For evaluation of the average thickness t of glass flakes, 100 of the glass flakes were used. The evaluation of the average thickness t was carried out using Real Surface View Microscope VE-7800, manufactured by Keyence Corporation.

$Fe^{2+}/(Fe^{2+}+Fe^{3+})$ of the produced glass flakes was determined by the o-phenanthroline spectrometric method previously described.

The produced glass flakes were evaluated for their visible transmittance. The visible transmittance was determined for a thickness of 15 μm according to JIS R 3106 using a spectrophotometer (manufactured by Shimadzu Corporation, UV 3100PC) with illuminant A. The evaluated visible transmittances are shown in the row headed "Glass flakes" of Tables 1 to 11.

The average thickness t of the glass flakes produced in the examples was much smaller than 15 μm. Thus, the following method was used to calculate the visible transmittance for a thickness of 15 μm of the glass flakes from an approximate equation.

First, light of the illuminant A was applied perpendicularly to the principal surface (the surface perpendicular to the thickness direction) of the glass flake. Next, an optical microscope was used to take a photograph of the glass flake viewed in plan from the side opposite to the illuminant A with respect to the glass flake. The lightness L* of the glass flake was read from this photograph, where the lightness of a photograph observed in the absence of the illuminant was defined as 0, and the lightness of a photograph observed in the presence of the illuminant alone without any glass flake was defined as 100. The lightness L* can be read, for example, by converting such a photograph to an image file of a personal computer and analyzing the image file with means such as an image editing application. The read lightness L* of the glass flake can be converted to Y/Yn according to JIS Z 8729, and this Y/Yn was determined as an approximation of the visible transmittance. Y is one of the tristimulus values in the XYZ color system and a stimulus value representing the brightness. Yn is the value of Y as determined for standard light from a perfect reflecting diffuser. The above procedure was conducted for two glass flakes having different thicknesses close to 15 μm, and an approximate equation representing the relationship between thickness and visible transmittance was created on the basis of the Lambert-Beer law. This equation was used to calculate the visible transmittance (a converted value) for a thickness of 15 μm.

The results of evaluation of Examples and Comparative Examples are shown in Tables 1 to 11 below. For the glass compositions shown in the tables, the contents of the components are all expressed in units of mass %. ΔT shown in Tables 1 to 11, as previously described, is a temperature difference calculated by subtracting the devitrification temperature from the working temperature of the glass composition. ΔW is a weight decrease of the glass composition and serves as an index of the acid resistance of the glass composition.

TABLE 1

| Component (mass %) or property | Example 1 | Example 2 | Example 3 | Example 4 | Example 5 |
|---|---|---|---|---|---|
| $SiO_2$ | 66.14 | 67.89 | 66.94 | 67.81 | 67.78 |
| $B_2O_3$ | 4.62 | 4.74 | 4.68 | 4.74 | 4.74 |
| $Al_2O_3$ | 3.96 | 4.07 | 4.01 | 4.06 | 4.06 |
| MgO | 2.56 | 3.28 | 2.59 | 3.24 | 3.25 |
| CaO | 6.49 | 8.29 | 6.55 | 8.19 | 8.23 |
| ZnO | 3.58 | — | 3.61 | — | — |
| $Li_2O$ | — | 0.60 | 0.59 | 0.60 | 0.60 |
| $Na_2O$ | 10.03 | 10.30 | 10.16 | 10.29 | 10.29 |
| $K_2O$ | 2.59 | 0.78 | 0.77 | 0.78 | 0.78 |
| $Li_2O + Na_2O + K_2O$ | 12.62 | 11.68 | 11.52 | 11.67 | 11.67 |
| $TiO_2$ | — | — | — | 0.13 | — |
| FeO | 0.009 | 0.022 | 0.020 | 0.081 | 0.109 |
| $T-Fe_2O_3$ | 0.03 | 0.05 | 0.10 | 0.16 | 0.27 |
| $Fe^{2+}/(Fe^{2+} + Fe^{3+})$ | 0.32 | 0.48 | 0.22 | 0.56 | 0.45 |
| Melting temperature [° C.] | 1500 | 1500 | 1500 | 1500 | 1500 |
| Melting time [hours] | 0.5 | 1 | 0.5 | 0.5 | 0.5 |

TABLE 1-continued

| Component (mass %) or property | Example 1 | Example 2 | Example 3 | Example 4 | Example 5 |
|---|---|---|---|---|---|
| Amount of added carbon [%] | 0.10 | 0.10 | — | 0.10 | 0.07 |
| Glass composition | | | | | |
| Glass transition temperature [° C.] | 558 | 552 | 549 | 552 | 552 |
| Devitrification temperature [° C.] | 990 | 1021 | 986 | 1021 | 1021 |
| Working temperature [° C.] | 1189 | 1160 | 1165 | 1160 | 1160 |
| ΔT [° C.] | 199 | 139 | 179 | 139 | 139 |
| ΔW [mass %] | 0.31 | 0.37 | 0.50 | 0.37 | 0.37 |
| Amount of alkali dissolution [mg] | 0.08 | 0.12 | 0.11 | 0.12 | 0.12 |
| Color of glass | Blue | Blue | Yellowish green | Blue | Blue |
| $T_{750nm}$ [%] (thickness: 1 mm) | 90.7 | 88.9 | 89.2 | 83.2 | 80.2 |
| $T_{550nm}$ [%] (thickness: 1 mm) | 91.3 | 91.0 | 91.1 | 90.8 | 90.4 |
| $T_{350nm}$ [%] (thickness: 1 mm) | 83.3 | 82.3 | 77.5 | 78.6 | 72.1 |
| Glass flakes | | | | | |
| $Fe^{2+}/(Fe^{2+} + Fe^{3+})$ | 0.34 | 0.50 | 0.18 | 0.56 | 0.44 |
| Visible transmittance [%] (thickness: 15 μm) | 91.4 | 91.4 | 91.2 | 91.1 | 91.4 |

TABLE 2

| Component (mass %) or property | Example 6 | Example 7 | Example 8 | Example 9 | Example 10 | Example 11 |
|---|---|---|---|---|---|---|
| $SiO_2$ | 54.92 | 54.87 | 54.87 | 54.72 | 55.46 | 54.86 |
| $B_2O_3$ | 5.95 | 5.95 | 5.95 | 5.93 | 6.01 | 5.95 |
| $Al_2O_3$ | 14.53 | 14.52 | 14.53 | 14.48 | 14.68 | 14.52 |
| MgO | 0.38 | 0.38 | 0.38 | 0.38 | 3.61 | 0.38 |
| CaO | 22.90 | 22.78 | 22.85 | 23.45 | 19.34 | 24.19 |
| $Na_2O$ | 0.49 | 0.49 | 0.49 | 0.49 | 0.50 | — |
| $K_2O$ | 0.30 | 0.30 | 0.30 | 0.30 | 0.30 | — |
| $Li_2O + Na_2O + K_2O$ | 0.79 | 0.79 | 0.79 | 0.79 | 0.80 | — |
| $TiO_2$ | — | 0.13 | — | — | — | — |
| FeO | 0.024 | 0.065 | 0.081 | 0.076 | 0.058 | 0.035 |
| $T-Fe_2O_3$ | 0.05 | 0.10 | 0.15 | 0.25 | 0.10 | 0.10 |
| $Fe^{2+}/(Fe^{2+} + Fe^{3+})$ | 0.53 | 0.72 | 0.60 | 0.34 | 0.64 | 0.39 |
| $F_2$ | 0.48 | 0.48 | 0.48 | — | — | — |
| Melting temperature [° C.] | 1550 | 1550 | 1550 | 1550 | 1550 | 1550 |
| Melting time [hours] | 0.5 | 0.5 | 0.5 | 1 | 0.5 | 0.5 |
| Amount of added carbon [%] | 0.10 | 0.10 | 0.10 | — | 0.20 | 0.01 |
| Glass composition | | | | | | |
| Glass transition temperature [° C.] | 681 | 681 | 681 | 698 | 691 | 708 |
| Devitrification temperature [° C.] | 1090 | 1090 | 1090 | 1090 | 1127 | 1087 |
| Working temperature [° C.] | 1205 | 1205 | 1205 | 1205 | 1210 | 1205 |
| ΔT [° C.] | 115 | 115 | 115 | 115 | 83 | 118 |
| Amount of alkali dissolution [mg] | 0.12 | 0.12 | 0.12 | 0.12 | 0.12 | — |
| Color of glass | Blue | Blue | Blue | Yellowish green | Blue | Yellowish green |
| $T_{750nm}$ [%] (thickness: 1 mm) | 89.1 | 86.0 | 85.0 | 85.4 | 86.8 | 88.3 |

TABLE 2-continued

| Component (mass %) or property | Example 6 | Example 7 | Example 8 | Example 9 | Example 10 | Example 11 |
|---|---|---|---|---|---|---|
| $T_{550nm}$ [%] (thickness: 1 mm) | 90.5 | 89.9 | 89.8 | 89.9 | 90.3 | 90.4 |
| $T_{350nm}$ [%] (thickness: 1 mm) | 77.4 | 75.8 | 65.5 | 40.5 | 73.3 | 65.2 |
| Glass flakes | | | | | | |
| $Fe^{2+}/(Fe^{2+} + Fe^{3+})$ | 0.49 | 0.76 | 0.62 | 0.36 | 0.60 | 0.36 |
| Visible transmittance [%] (thickness: 15 μm) | 90.9 | 90.7 | 90.7 | 90.7 | 91.0 | 90.8 |

TABLE 3

| Component (mass %) or property | Example 12 | Example 13 | Example 14 | Example 15 | Example 16 | Example 17 | Example 18 | Example 19 | Example 20 | Example 21 |
|---|---|---|---|---|---|---|---|---|---|---|
| $SiO_2$ | 63.52 | 64.60 | 63.28 | 63.28 | 61.54 | 61.55 | 61.54 | 61.47 | 60.67 | 60.65 |
| $B_2O_3$ | 1.15 | 0.58 | 1.15 | 1.15 | — | — | — | — | — | — |
| $Al_2O_3$ | 11.28 | 11.39 | 11.25 | 11.24 | 11.19 | 11.20 | 11.19 | 11.18 | 11.31 | 11.30 |
| MgO | 2.05 | 2.56 | 2.03 | 2.04 | 3.18 | 3.22 | 3.22 | 3.21 | 3.33 | 3.32 |
| CaO | 20.39 | 18.37 | 20.13 | 20.24 | 22.87 | 23.30 | 23.27 | 23.20 | 23.85 | 23.83 |
| $Li_2O$ | 1.58 | 2.39 | 1.43 | 1.43 | 0.14 | — | — | — | 0.79 | 0.79 |
| $Na_2O$ | — | — | 0.20 | 0.20 | 0.30 | 0.39 | 0.39 | 0.39 | — | — |
| $K_2O$ | — | — | 0.16 | 0.16 | 0.45 | 0.29 | 0.29 | 0.29 | — | — |
| $Li_2O + Na_2O + K_2O$ | 1.58 | 2.39 | 1.79 | 1.79 | 0.89 | 0.68 | 0.68 | 0.68 | 0.79 | 0.79 |
| $TiO_2$ | — | — | 0.26 | — | 0.25 | — | — | — | — | — |
| FeO | 0.009 | 0.056 | 0.042 | 0.140 | 0.040 | 0.015 | 0.044 | 0.094 | 0.015 | 0.055 |
| $T-Fe_2O_3$ | 0.03 | 0.11 | 0.11 | 0.26 | 0.08 | 0.05 | 0.10 | 0.26 | 0.05 | 0.11 |
| $Fe^{2+}/(Fe^{2+} + Fe^{3+})$ | 0.35 | 0.57 | 0.42 | 0.60 | 0.55 | 0.34 | 0.49 | 0.40 | 0.34 | 0.56 |
| Melting temperature [° C.] | 1550 | 1550 | 1550 | 1550 | 1550 | 1550 | 1550 | 1550 | 1550 | 1550 |
| Melting time [hours] | 0.5 | 0.5 | 0.5 | 0.5 | 0.5 | 0.5 | 0.5 | 0.5 | 0.5 | 0.5 |
| Amount of added carbon [%] | — | 0.10 | 0.01 | 0.08 | — | 0.07 | 0.04 | 0.01 | — | 0.09 |
| Glass composition | | | | | | | | | | |
| Glass transition temperature [° C.] | 650 | 619 | 653 | 653 | 729 | 749 | 749 | 749 | 697 | 697 |
| Devitrification temperature [° C.] | 1173 | 1162 | 1176 | 1177 | 1207 | 1216 | 1216 | 1216 | 1210 | 1210 |
| Working temperature [° C.] | 1228 | 1210 | 1223 | 1223 | 1250 | 1253 | 1253 | 1253 | 1214 | 1214 |
| ΔT [° C.] | 55 | 48 | 47 | 46 | 43 | 37 | 37 | 37 | 4 | 4 |
| ΔW [mass %] | 0.26 | 0.12 | 0.26 | 0.28 | 0.41 | 0.25 | 0.25 | 0.25 | 0.28 | 0.28 |
| Color of glass | Yellowish green | Blue | Yellowish green | Blue | Blue | Yellowish green | Blue | Yellowish green | Yellowish green | Blue |
| $T_{750nm}$ [%] (thickness: 1 mm) | 90.4 | 87.2 | 88.3 | 81.4 | 88.2 | 89.8 | 87.5 | 84.6 | 89.9 | 87.1 |
| $T_{550nm}$ [%] (thickness: 1 mm) | 90.9 | 90.3 | 90.6 | 89.2 | 90.5 | 90.7 | 90.1 | 89.9 | 90.8 | 90.2 |
| $T_{350nm}$ [%] (thickness: 1 mm) | 80.2 | 71.0 | 66.3 | 54.6 | 74.0 | 74.2 | 68.1 | 43.5 | 74.3 | 70.5 |
| Glass flakes | | | | | | | | | | |
| $Fe^{2+}/(Fe^{2+} + Fe^{3+})$ | 0.37 | 0.54 | 0.46 | 0.58 | 0.58 | 0.38 | 0.45 | 0.39 | 0.36 | 0.56 |
| Visible transmittance [%] (thickness: 15 μm) | 90.7 | 91.0 | 90.9 | 90.9 | 90.8 | 90.7 | 91.0 | 90.9 | 90.9 | 90.6 |

TABLE 4

| Component (mass %) or property | Example 22 | Example 23 | Example 24 | Example 25 | Example 26 | Example 27 |
|---|---|---|---|---|---|---|
| $SiO_2$ | 60.40 | 61.51 | 61.43 | 61.15 | 60.75 | 60.12 |
| $B_2O_3$ | — | — | — | — | — | 0.57 |
| $Al_2O_3$ | 11.26 | 11.28 | 10.42 | 11.21 | 11.23 | 11.21 |
| MgO | 3.28 | 3.20 | 3.43 | 3.34 | 3.43 | 3.41 |
| CaO | 23.59 | 22.96 | 24.59 | 23.94 | 24.54 | 24.43 |
| $Li_2O$ | 0.59 | 0.79 | — | — | — | — |
| $Na_2O$ | 0.20 | — | — | — | — | — |
| $K_2O$ | 0.31 | — | — | — | — | — |
| $Li_2O + Na_2O + K_2O$ | 1.10 | 0.79 | — | — | — | — |

TABLE 4-continued

| Component (mass %) or property | Example 22 | Example 23 | Example 24 | Example 25 | Example 26 | Example 27 |
|---|---|---|---|---|---|---|
| $TiO_2$ | 0.26 | — | — | 0.26 | — | — |
| FeO | 0.048 | 0.147 | 0.041 | 0.044 | 0.023 | 0.094 |
| T-$Fe_2O_3$ | 0.11 | 0.26 | 0.13 | 0.10 | 0.05 | 0.26 |
| $Fe^{2+}/(Fe^{2+} + Fe^{3+})$ | 0.48 | 0.63 | 0.35 | 0.49 | 0.52 | 0.40 |
| Melting temperature [° C.] | 1550 | 1550 | 1550 | 1550 | 1550 | 1550 |
| Melting time [hours] | 0.5 | 0.5 | 0.5 | 0.5 | 0.5 | 0.5 |
| Amount of added carbon [%] | 0.04 | 0.10 | — | 0.04 | 0.09 | 0.01 |
| Glass composition | | | | | | |
| Glass transition temperature [° C.] | 702 | 697 | 749 | 750 | 754 | 744 |
| Devitrification temperature [° C.] | 1192 | 1205 | 1223 | 1200 | 1218 | 1221 |
| Working temperature [° C.] | 1210 | 1221 | 1248 | 1255 | 1247 | 1237 |
| ΔT [° C.] | 18 | 16 | 25 | 55 | 29 | 16 |
| ΔW [mass %] | 0.27 | 0.21 | 0.43 | 0.41 | 0.55 | 0.84 |
| Color of glass | Blue | Blue | Yellowish green | Blue | Blue | Yellowish green |
| $T_{750nm}$ [%] (thickness: 1 mm) | 87.6 | 80.7 | 87.9 | 87.7 | 89.2 | 84.2 |
| $T_{550nm}$ [%] (thickness: 1 mm) | 90.2 | 88.9 | 90.3 | 90.3 | 90.6 | 89.5 |
| $T_{350nm}$ [%] (thickness: 1 mm) | 67.9 | 56.3 | 59.3 | 68.3 | 77.3 | 43.1 |
| Glass flakes | | | | | | |
| $Fe^{2+}/(Fe^{2+} + Fe^{3+})$ | 0.43 | 0.59 | 0.40 | 0.48 | 0.54 | 0.39 |
| Visible transmittance [%] (thickness: 15 μm) | 90.8 | 90.8 | 90.8 | 90.7 | 91.0 | 90.9 |

TABLE 5

| Component (mass %) or property | Example 28 | Example 29 | Example 30 | Example 31 |
|---|---|---|---|---|
| $SiO_2$ | 65.30 | 65.71 | 65.48 | 65.69 |
| $B_2O_3$ | — | — | — | 1.14 |
| $Al_2O_3$ | 11.07 | 11.14 | 11.10 | 9.30 |
| MgO | 2.65 | 2.23 | 2.63 | 2.62 |
| CaO | 16.41 | 18.98 | 17.22 | 17.15 |
| ZnO | 1.34 | — | — | — |
| $Li_2O$ | 1.71 | 1.89 | 1.71 | — |
| $Na_2O$ | 1.15 | — | 1.15 | 3.68 |
| $K_2O$ | 0.34 | — | 0.34 | 0.26 |
| $Li_2O + Na_2O + K_2O$ | 3.20 | 1.89 | 3.20 | 3.94 |
| $TiO_2$ | — | — | 0.26 | — |
| FeO | 0.012 | 0.024 | 0.034 | 0.059 |
| T-$Fe_2O_3$ | 0.03 | 0.05 | 0.11 | 0.16 |
| $Fe^{2+}/(Fe^{2+} + Fe^{3+})$ | 0.44 | 0.53 | 0.34 | 0.41 |
| Melting temperature [° C.] | 1550 | 1550 | 1550 | 1550 |
| Melting time [hours] | 0.5 | 0.5 | 0.5 | 0.5 |
| Amount of added carbon [%] | 0.04 | 0.10 | — | 0.01 |
| Glass composition | | | | |
| Glass transition temperature [° C.] | 642 | 655 | 644 | 682 |
| Devitrification temperature [° C.] | 1178 | 1170 | 1181 | 1224 |
| Working temperature [° C.] | 1261 | 1258 | 1253 | 1288 |
| ΔT [° C.] | 83 | 88 | 72 | 64 |
| ΔW [mass %] | 0.11 | 0.13 | 0.17 | 0.28 |
| Color of glass | Blue | Blue | Yellowish green | Yellowish green |
| $T_{750nm}$ [%] (thickness: 1 mm) | 90.1 | 89.0 | 88.8 | 87.0 |
| $T_{550nm}$ [%] (thickness: 1 mm) | 90.7 | 90.4 | 90.6 | 90.3 |
| $T_{350nm}$ [%] (thickness: 1 mm) | 80.9 | 77.4 | 63.9 | 57.6 |
| Glass flakes | | | | |
| $Fe^{2+}/(Fe^{2+} + Fe^{3+})$ | 0.41 | 0.57 | 0.29 | 0.40 |
| Visible transmittance [%] (thickness: 15 μm) | 90.8 | 90.7 | 90.8 | 90.9 |

TABLE 6

| Component (mass %) or property | Example 32 | Example 33 | Example 34 | Example 35 | Example 36 |
|---|---|---|---|---|---|
| $SiO_2$ | 66.57 | 63.21 | 67.28 | 64.23 | 65.04 |
| $B_2O_3$ | — | — | — | 1.15 | — |
| $Al_2O_3$ | 11.20 | 10.88 | 9.52 | 11.06 | 11.02 |
| MgO | 2.09 | 2.78 | 2.21 | 2.18 | 2.17 |
| CaO | 16.03 | 14.81 | 16.36 | 16.10 | 15.11 |
| ZnO | — | — | — | — | 1.34 |
| $Li_2O$ | 3.07 | — | 2.33 | 1.80 | 1.80 |
| $Na_2O$ | — | 7.48 | 2.22 | 2.89 | 2.88 |
| $K_2O$ | 1.01 | 0.53 | — | 0.48 | 0.48 |
| $Li_2O + Na_2O + K_2O$ | 4.08 | 8.01 | 4.55 | 5.17 | 5.16 |
| $TiO_2$ | — | 0.26 | — | — | — |
| FeO | 0.009 | 0.017 | 0.017 | 0.042 | 0.040 |
| T-$Fe_2O_3$ | 0.03 | 0.05 | 0.08 | 0.11 | 0.16 |
| $Fe^{2+}/(Fe^{2+} + Fe^{3+})$ | 0.32 | 0.37 | 0.23 | 0.42 | 0.28 |
| Melting temperature [° C.] | 1550 | 1550 | 1550 | 1550 | 1550 |
| Melting time [hours] | 0.5 | 0.5 | 0.5 | 0.5 | 0.5 |
| Amount of added carbon [%] | 0.10 | 0.10 | — | 0.10 | 0.01 |

TABLE 6-continued

| Component (mass %) or property | Example 32 | Example 33 | Example 34 | Example 35 | Example 36 |
|---|---|---|---|---|---|
| Glass composition | | | | | |
| Glass transition temperature [° C.] | 605 | 652 | 607 | 616 | 617 |
| Devitrification temperature [° C.] | 1157 | 1227 | 1187 | 1172 | 1171 |
| Working temperature [° C.] | 1226 | 1268 | 1232 | 1215 | 1247 |
| ΔT [° C.] | 69 | 41 | 45 | 43 | 76 |
| ΔW [mass %] | 0.08 | 0.40 | 0.08 | 0.26 | 0.12 |
| Amount of alkali dissolution [mg] | — | — | — | — | — |
| Color of glass | Blue | Blue | Yellowish green | Blue | Yellowish green |
| $T_{750nm}$ [%] (thickness: 1 mm) | 90.5 | 89.8 | 89.6 | 87.6 | 87.5 |
| $T_{550nm}$ [%] (thickness: 1 mm) | 91.0 | 91.1 | 90.8 | 90.6 | 90.5 |
| $T_{350nm}$ [%] (thickness: 1 mm) | 81.5 | 78.3 | 72.3 | 72.4 | 62.5 |
| Glass flakes | | | | | |
| $Fe^{2+}/(Fe^{2+} + Fe^{3+})$ | 0.36 | 0.35 | 0.25 | 0.42 | 0.33 |
| Visible transmittance [%] (thickness: 15 μm) | 90.9 | 91.1 | 91.0 | 91.0 | 91.0 |

TABLE 7

| Component (mass %) or property | Example 37 | Example 38 | Example 39 | Example 40 | Example 41 | Example 42 | Example 43 | Example 44 | Example 45 | Example 46 |
|---|---|---|---|---|---|---|---|---|---|---|
| $SiO_2$ | 66.63 | 63.22 | 63.30 | 63.22 | 66.32 | 66.61 | 65.92 | 65.61 | 66.45 | 65.32 |
| $B_2O_3$ | 1.27 | — | — | — | 1.13 | — | — | — | — | — |
| $Al_2O_3$ | 9.10 | 10.88 | 10.89 | 10.88 | 8.11 | 8.02 | 9.71 | 9.66 | 9.78 | 8.11 |
| MgO | 3.18 | 3.84 | 2.73 | 2.76 | 3.03 | — | 2.98 | 2.99 | 3.03 | 3.49 |
| CaO | 8.17 | 9.88 | 12.15 | 11.82 | 7.58 | 11.67 | 7.47 | 7.48 | 7.58 | 7.82 |
| ZnO | — | — | — | 0.66 | — | — | — | — | — | 1.33 |
| $Li_2O$ | 0.56 | — | 0.50 | 0.50 | — | — | — | 0.48 | 0.49 | — |
| $Na_2O$ | 10.24 | 11.32 | 9.32 | 9.31 | 13.12 | 12.98 | 13.04 | 9.98 | 12.57 | 13.12 |
| $K_2O$ | 0.82 | 0.81 | 0.75 | 0.75 | 0.68 | 0.67 | 0.67 | 3.70 | — | 0.68 |
| $Li_2O + Na_2O + K_2O$ | 11.62 | 12.13 | 10.57 | 10.56 | 13.80 | 13.65 | 13.71 | 14.16 | 13.06 | 13.80 |
| $TiO_2$ | — | — | 0.26 | — | — | — | 0.13 | — | — | — |
| FeO | 0.009 | 0.017 | 0.024 | 0.038 | 0.008 | 0.016 | 0.017 | 0.025 | 0.035 | 0.048 |
| $T-Fe_2O_3$ | 0.03 | 0.05 | 0.10 | 0.10 | 0.03 | 0.05 | 0.08 | 0.10 | 0.10 | 0.13 |
| $Fe^{2+}/(Fe^{2+} + Fe^{3+})$ | 0.32 | 0.37 | 0.27 | 0.42 | 0.31 | 0.36 | 0.23 | 0.28 | 0.39 | 0.41 |
| Melting temperature [° C.] | 1550 | 1550 | 1550 | 1550 | 1550 | 1550 | 1550 | 1550 | 1550 | 1550 |
| Melting time [hours] | 0.5 | 0.5 | 0.5 | 0.5 | 0.5 | 0.5 | 0.5 | 0.5 | 0.5 | 0.5 |
| Amount of added carbon [%] | — | 0.10 | 0.02 | 0.10 | 0.07 | 0.05 | 0.02 | 0.01 | 0.07 | 0.07 |
| Glass composition | | | | | | | | | | |
| Glass transition temperature [° C.] | 579 | 614 | 605 | 601 | 582 | 594 | 591 | 560 | 568 | 585 |
| Devitrification temperature [° C.] | 1133 | 1175 | 1190 | 1187 | 1082 | 1177 | 1110 | 1114 | 1104 | 1103 |
| Working temperature [° C.] | 1264 | 1263 | 1247 | 1245 | 1244 | 1238 | 1274 | 1275 | 1265 | 1242 |
| ΔT [° C.] | 131 | 88 | 57 | 58 | 162 | 61 | 164 | 161 | 161 | 139 |
| ΔW [mass %] | 0.17 | 0.35 | 0.29 | 0.25 | 0.22 | 0.18 | 0.24 | 0.16 | 0.23 | 0.13 |
| Amount of alkali dissolution [mg] | — | — | — | — | — | — | — | — | — | — |
| Color of glass | Blue | Blue | Yellowish green | Blue | Blue | Blue | Yellowish green | Yellowish green | Blue | Blue |
| $T_{750nm}$ [%] (thickness: 1 mm) | 90.8 | 89.6 | 88.6 | 87.2 | 90.6 | 89.7 | 89.5 | 88.6 | 87.5 | 86.3 |
| $T_{550nm}$ [%] (thickness: 1 mm) | 91.3 | 91.2 | 91.0 | 91.0 | 91.1 | 91.2 | 91.0 | 91.1 | 91.0 | 90.9 |
| $T_{350nm}$ [%] (thickness: 1 mm) | 83.3 | 81.9 | 77.6 | 79.4 | 83.1 | 81.9 | 79.1 | 78.1 | 79.1 | 77.9 |
| Glass flakes | | | | | | | | | | |
| $Fe^{2+}/(Fe^{2+} + Fe^{3+})$ | 0.28 | 0.38 | 0.26 | 0.46 | 0.34 | 0.32 | 0.26 | 0.29 | 0.38 | 0.40 |
| Visible transmittance [%] (thickness: 15 μm) | 91.1 | 91.1 | 91.1 | 91.2 | 91.3 | 91.1 | 91.1 | 91.4 | 91.1 | 91.4 |

TABLE 8

| Component (mass %) or property | Example 47 | Example 48 | Example 49 | Example 50 |
|---|---|---|---|---|
| $SiO_2$ | 67.78 | 66.45 | 66.27 | 66.22 |
| $B_2O_3$ | 13.33 | 15.45 | 14.20 | 14.20 |
| $Al_2O_3$ | 7.19 | 7.15 | 7.81 | 7.81 |
| MgO | 0.11 | 0.10 | 0.18 | 0.21 |
| CaO | 0.05 | 0.04 | — | — |
| $Li_2O$ | 0.30 | — | — | — |
| $Na_2O$ | 10.40 | 10.13 | 10.76 | 10.76 |
| $K_2O$ | 0.79 | 0.58 | 0.55 | 0.55 |
| $Li_2O + Na_2O + K_2O$ | 11.49 | 10.71 | 11.31 | 11.31 |
| $TiO_2$ | — | — | 0.13 | — |
| FeO | 0.019 | 0.016 | 0.030 | 0.083 |
| $T-Fe_2O_3$ | 0.05 | 0.10 | 0.10 | 0.25 |
| $Fe^{2+}/(Fe^{2+} + Fe^{3+})$ | 0.42 | 0.18 | 0.33 | 0.37 |
| Melting temperature [° C.] | 1580 | 1580 | 1580 | 1580 |
| Melting time [hours] | 0.5 | 0.5 | 0.5 | 0.5 |
| Amount of added carbon [%] | 0.21 | — | 0.08 | 0.13 |
| Glass composition | | | | |
| Devitrification temperature [° C.] | 980 | 974 | 942 | 940 |
| Working temperature [° C.] | 1262 | 1272 | 1266 | 1272 |
| ΔT [° C.] | 282 | 298 | 324 | 332 |
| Amount of alkali dissolution [mg] | 0.01 | 0.02 | 0.01 | 0.03 |
| Color of glass | Blue | Yellow | Yellowish green | Yellowish green |
| $T_{750nm}$ [%] (thickness: 1 mm) | 89.3 | 89.5 | 88.2 | 82.4 |
| $T_{550nm}$ [%] (thickness: 1 mm) | 91.1 | 91.1 | 91.2 | 90.8 |
| $T_{350nm}$ [%] (thickness: 1 mm) | 82.1 | 77.0 | 78.5 | 70.8 |
| Glass flakes | | | | |
| $Fe^{2+}/(Fe^{2+} + Fe^{3+})$ | 0.39 | 0.22 | 0.35 | 0.41 |
| Visible transmittance [%] (thickness: 15 μm) | 91.0 | 91.1 | 91.4 | 91.3 |

TABLE 9

| Component (mass %) or property | Example 51 | Example 52 | Example 53 | Example 54 |
|---|---|---|---|---|
| $SiO_2$ | 57.72 | 58.19 | 59.52 | 58.83 |
| $B_2O_3$ | 1.15 | — | — | — |
| $Al_2O_3$ | 19.47 | 19.30 | 19.42 | 19.51 |
| MgO | 15.11 | 12.34 | 13.46 | 15.12 |
| CaO | 5.72 | 9.35 | 7.55 | 5.73 |
| $Na_2O$ | 0.41 | 0.41 | — | 0.41 |
| $K_2O$ | 0.16 | 0.15 | — | 0.16 |
| $Li_2O + Na_2O + K_2O$ | 0.57 | 0.56 | — | 0.57 |
| $TiO_2$ | — | — | — | 0.13 |
| FeO | 0.157 | 0.110 | 0.023 | 0.048 |
| $T-Fe_2O_3$ | 0.26 | 0.26 | 0.05 | 0.11 |
| $Fe^{2+}/(Fe^{2+} + Fe^{3+})$ | 0.67 | 0.47 | 0.52 | 0.48 |
| Melting temperature [° C.] | 1580 | 1580 | 1580 | 1580 |
| Melting time [hours] | 0.5 | 0.5 | 0.5 | 0.5 |
| Amount of added carbon [%] | 0.18 | — | 0.06 | 0.04 |
| Glass composition | | | | |
| Devitrification temperature [° C.] | 1272 | 1226 | 1257 | 1283 |
| Working temperature [° C.] | 1272 | 1275 | 1286 | 1284 |
| ΔT [° C.] | 0 | 49 | 29 | 1 |
| Color of glass | Bluish green | Yellowish green | Yellowish green | Yellowish green |
| $T_{750nm}$ [%] (thickness: 1 mm) | 86.5 | 87.8 | 90.2 | 89.5 |
| $T_{550nm}$ [%] (thickness: 1 mm) | 89.6 | 89.2 | 90.5 | 90.1 |
| $T_{350nm}$ [%] (thickness: 1 mm) | 38.1 | 23.1 | 68.0 | 51.5 |
| Glass flakes | | | | |
| $Fe^{2+}/(Fe^{2+} + Fe^{3+})$ | 0.65 | 0.49 | 0.50 | 0.44 |
| Visible transmittance [%] (thickness: 15 μm) | 90.7 | 90.8 | 90.8 | 90.7 |

TABLE 10

| Component (mass %) or property | Example 55 | Example 56 | Example 57 | Example 58 |
|---|---|---|---|---|
| $SiO_2$ | 69.63 | 68.98 | 69.67 | 69.54 |
| $Al_2O_3$ | 1.47 | 1.46 | 1.47 | 1.47 |
| MgO | 2.57 | 2.79 | 2.79 | 2.55 |
| CaO | 6.44 | 6.94 | 6.96 | 6.38 |
| $Li_2O$ | 1.96 | — | 0.98 | 1.95 |
| $Na_2O$ | 9.13 | 13.06 | 11.16 | 9.11 |
| $K_2O$ | 0.68 | 0.67 | 0.68 | 0.68 |
| $Li_2O + Na_2O + K_2O$ | 11.77 | 13.73 | 12.82 | 11.74 |
| $TiO_2$ | — | — | 0.13 | — |
| $ZrO_2$ | 8.07 | 6.00 | 6.06 | 8.06 |
| FeO | 0.019 | 0.041 | 0.031 | 0.089 |
| $T-Fe_2O_3$ | 0.05 | 0.10 | 0.10 | 0.26 |
| $Fe^{2+}/(Fe^{2+} + Fe^{3+})$ | 0.42 | 0.46 | 0.34 | 0.38 |
| Melting temperature [° C.] | 1550 | 1550 | 1550 | 1550 |
| Melting time [hours] | 0.5 | 0.5 | 0.5 | 0.5 |
| Amount of added carbon [%] | 0.02 | 0.04 | — | 0.01 |
| Glass composition | | | | |
| Devitrification temperature [° C.] | 1024 | 1078 | 1023 | 1024 |
| Working temperature [° C.] | 1228 | 1256 | 1232 | 1228 |
| ΔT [° C.] | 204 | 178 | 209 | 204 |
| ΔW [mass %] | 0.08 | 0.09 | 0.09 | 0.08 |
| Amount of alkali dissolution [mg] | 0.09 | 0.14 | 0.14 | 0.09 |
| Color of glass | Blue | Blue | Blue | Yellowish green |
| $T_{750nm}$ [%] (thickness: 1 mm) | 89.1 | 86.6 | 87.9 | 82.2 |
| $T_{550nm}$ [%] (thickness: 1 mm) | 90.9 | 90.8 | 90.9 | 90.8 |
| $T_{350nm}$ [%] (thickness: 1 mm) | 81.9 | 79.6 | 78.3 | 71.0 |
| Glass flakes | | | | |
| $Fe^{2+}/(Fe^{2+} + Fe^{3+})$ | 0.39 | 0.51 | 0.39 | 0.41 |
| Visible transmittance [%] (thickness: 15 μm) | 91.3 | 91.1 | 91.2 | 91.1 |

TABLE 11

| Component (mass %) or property | Comparative Example 1 | Comparative Example 2 | Comparative Example 3 | Comparative Example 4 |
|---|---|---|---|---|
| $SiO_2$ | 67.05 | 66.59 | 66.75 | 47.20 |
| $B_2O_3$ | 4.68 | 4.65 | 4.66 | — |
| $Al_2O_3$ | 4.02 | 3.99 | 4.00 | 5.70 |
| MgO | 2.58 | 2.51 | 2.54 | 5.40 |
| CaO | 6.53 | 6.35 | 6.45 | 11.40 |
| ZnO | 3.61 | 3.55 | 3.59 | — |
| $Li_2O$ | 0.59 | 0.58 | 0.59 | — |
| $Na_2O$ | 10.17 | 10.10 | 10.13 | — |
| $K_2O$ | 0.77 | 0.77 | 0.77 | — |

TABLE 11-continued

| Component (mass %) or property | Comparative Example 1 | Comparative Example 2 | Comparative Example 3 | Comparative Example 4 |
|---|---|---|---|---|
| $TiO_2$ | — | — | — | 5.60 |
| FeO | — | 0.213 | 0.314 | — |
| T-$Fe_2O_3$ | — | 0.91 | 0.52 | 24.70 |
| $Fe^{2+}/(Fe^{2+} + Fe^{3+})$ | — | 0.26 | 0.67 | — |
| Melting temperature [° C.] | 1500 | 1500 | 1500 | 1500 |
| Melting time [hours] | 0.5 | 0.5 | 0.5 | 4 |
| Amount of added carbon [%] | — | 0.01 | 0.15 | — |
| Glass transition temperature [° C.] | 549 | 549 | 549 | — |
| Devitrification temperature [° C.] | 986 | 986 | 986 | — |
| Working temperature [° C.] | 1165 | 1165 | 1165 | — |
| ΔT [° C.] | 179 | 179 | 179 | — |
| ΔW [mass %] | 0.50 | 0.50 | 0.50 | — |
| Amount of alkali dissolution [mg] | 0.11 | 0.11 | 0.11 | — |
| Color of glass | Colorless | Green | Blue | Blackish brown |
| $T_{750nm}$ [%] (thickness: 1 mm) | 91.5 | 70.2 | 62.3 | <1.0 |
| $T_{550nm}$ [%] (thickness: 1 mm) | 91.3 | 89.6 | 89.1 | <1.0 |
| $T_{350nm}$ [%] (thickness: 1 mm) | 84.9 | 39.5 | 70.1 | <1.0 |
| Glass flakes | | | | |
| $Fe^{2+}/(Fe^{2+} + Fe^{3+})$ | — | 0.27 | 0.64 | 0.34 |
| Visible transmittance [%] (thickness: 15 μm) | 91.2 | 91.3 | 91.2 | 17.7 |

As shown in Tables 1 to 11, the glass flakes of Examples 1 to 58, for which the content and oxidation-reduction state of iron oxide were controlled as described above, had a visually observed color ranging from blue to yellow and had a light transmittance $T_{750nm}$ of 80.2 to 90.8% and a light transmittance $T_{350nm}$ of 23.1 to 83.3%. The visible transmittance (as calculated for a thickness of 15 μm) of the glass flakes of Examples 1 to 58 was as high as 90.6 to 91.4%.

Examples 1 to 5 correspond to glass and glass flakes having C-glass composition, Examples 6 to 11 correspond to glass and glass flakes having E-glass composition, Examples 12 to 27 correspond to glass and glass flakes having the glass composition A-3, Examples 28 to 31 correspond to glass and glass flakes having the glass composition A-4, Examples 32 to 36 correspond to glass and glass flakes having the glass composition A-5, Examples 37 to 40 correspond to glass and glass flakes having the glass composition A-6, Examples 41 to 46 correspond to glass and glass flakes having the glass composition A-7, Examples 47 to 50 correspond to glass and glass flakes having the glass composition A-8, Examples 51 to 54 correspond to glass and glass flakes having the glass composition A-9, and Examples 55 to 58 correspond to glass and glass flakes having the glass composition A-10. With any of the glass compositions A, glass flakes having a high visible transmittance and a controlled color were obtained by controlling the content and oxidation-reduction state of iron oxide as described above. The color of these glass flakes was quite different from that of glass flakes of Patent Literature 3 which contain iron oxide as a coloring component.

By contrast, the glass flakes of Comparative Example 1 had conventional C-glass composition, and as regards iron oxide the content of T-$Fe_2O_3$ was outside the T-$Fe_2O_3$ content range specified for the glass composition A. The glass flakes of Comparative Example 1 were colorless, and the color of these glass flakes was not able to be adjusted. Additionally, the glass flakes of Comparative Example 1 had a $T_{750nm}$ of 91.5%, which was higher than that of the glass flakes of Examples 1 to 58. Furthermore, the glass flakes of the Comparative Example 1 had a $T_{350nm}$ of 84.9%, which was higher than that of the glass flakes of Examples 1 to 58.

As for the glass flakes of Comparative Example 2, in particular iron oxide contained therein, the content of T-$Fe_2O_3$ was outside the T-$Fe_2O_3$ content range specified for the glass composition A. The glass flakes of Comparative Example 2 had a $T_{750nm}$ of 70.2%, which was lower than that of the glass flakes of Examples 1 to 58.

As for the glass flakes of Comparative Example 3, in particular iron oxide contained therein, the content of FeO was outside the FeO content range specified for the glass compositions A. The glass flakes of Comparative Example 3 had a $T_{750nm}$ of 62.3%, which was lower than that of the glass flakes of Examples 1 to 58. The glass flakes of Comparative Examples 2 and 3 showed a decrease in both $T_{750nm}$ and $T_{350nm}$ as compared to the glass flakes of Examples 1 to 58, and this means that the glass flakes of Comparative Examples 2 and 3 allowed lower flexibility in color control than the glass flakes of Examples 1 to 58.

The glass flakes of Comparative Example 4 were glass flakes as described in Example 7 of Patent Literature 3, and as regards iron oxide the content of T-$Fe_2O_3$ was outside the T-$Fe_2O_3$ content range specified for the glass compositions A. The color of the glass flakes of Comparative Example 4 was blackish brown. The glass flakes of Comparative Example 4 had a $T_{750nm}$ of less than 1.0%, which was lower than that of the glass flakes of Examples 1 to 58. Additionally, the glass flakes of Comparative Example 4 had a $T_{350nm}$ of less than 1.0%, which was lower than that of the glass flakes of Examples 1 to 58. Further, the glass flakes of Comparative Example 4 had a visible transmittance (as calculated for a thickness of 15 μm) of 17.7%, which was lower than that of the glass flakes of Examples 1 to 58.

Examples 59 to 116

Using the glass flakes 1 of Examples 1 to 58 produced as described above, glass flakes 1a with a titanium dioxide coating 2 were produced by liquid-phase deposition (Examples 59 to 116). The details of the procedures were as follows.

First, tin(II) chloride dihydrate was used as a metal salt and dissolved in ion-exchanged water, and dilute hydrochloric acid was added to the solution to adjust the pH of the solution to 2.0 to 2.5. Next, the glass flakes 1 of Examples 1 to 31 ground to an appropriate particle diameter were added to the pH-adjusted solution under stirring and, after 10 minutes, the solution containing the glass flakes 1 was filtered. Next, the glass flakes 1 filtered out were introduced, under stirring, into a solution prepared by dissolving hexachloroplatinic acid hexahydrate in ion-exchanged water and, after 10 minutes, the solution containing the glass flakes 1 was filtered. Next, the glass flakes 1 filtered out were introduced, under stirring, into an acidic hydrochloric acid solution with a pH of 0.7 prepared by adding a hydrochloric acid solution (35 mass %) to ion-exchanged water, and the temperature of the solution was raised to 75° C. To the solution was then added an aqueous titanium tetrachloride (TiCl$_4$) solution at a rate of 0.2 g/min on a titanium basis while an aqueous sodium hydroxide solution was simultaneously added to prevent change in the solution pH. Subsequently, neutralization reaction of the solution was allowed to proceed for 2 hours to cause titanium dioxide (TiO$_2$) and/or its hydrate to be deposited on the surface of the glass flakes 1. After that, the glass flakes 1 with the titanium dioxide coating 2 formed on the surface thereof were collected by filtration and dried at 180° C. for 2 hours to obtain coated glass flakes 1a.

Observation of the thus-produced coated glass flakes 1a with an electron microscope demonstrated for all the examples that the titanium dioxide coating 2 was formed on the surface of the glass flakes 1.

Examples 117 to 174

Using the glass flakes 1 of Examples 1 to 58 produced as described above, glass flakes 1a with a silver coating 2 were produced by electroless plating (Examples 117 to 174). The details of the procedures were as follows.

First, as in Examples 32 to 62, the glass flakes 1 ground to an appropriate particle diameter were subjected to the pretreatments with tin(II) chloride dihydrate and hexachloroplatinic acid hexahydrate. Next, 1 kg of the pretreated glass flakes 1 were introduced, under stirring, into a silver-containing solution prepared by adding 200 g of silver nitrate and an appropriate amount of aqueous ammonia to 10 L of ion-exchanged water. Next, a 14 mass % aqueous potassium sodium tartrate solution was further added as a reducing solution to cause silver to be deposited on the surface of the glass flakes 1. After that, the glass flakes 1a with the silver coating 2 formed on the surface thereof were collected by filtration and dried at 400° C. for 2 hours to obtain coated glass flakes 1a.

Observation of the thus-produced coated glass flakes 1a with an electron microscope demonstrated for all the examples that the silver coating 2 was formed on the surface of the glass flakes 1.

Examples 175 to 232

The glass flakes 1 of Examples 1 to 58 were ground to a given particle diameter, and the glass flakes were then mixed with a polyester resin to obtain polyester resin compositions of Examples 175 to 232 which contained the glass flakes 1. These polyester resin compositions and resin molded products obtained by molding of the compositions showed good dispersion of the glass flakes 1 and had a favorable color and appearance.

Examples 233 to 290

The coated glass flakes 1a of Examples 59 to 116 were mixed with epoxy acrylate to obtain vinyl ester paints of Examples 233 to 290 which contained the coated glass flakes 1a. These vinyl ester paints showed good dispersion of the coated glass flakes 1a, and paint films formed by application and drying of the paints had a favorable color and appearance.

Examples 291 to 348

The coated glass flakes 1a of Examples 59 to 116 were mixed with a facial cosmetic, in particular foundation, to obtain cosmetics of Examples 291 to 348 which contained the coated glass flakes 1a. These cosmetics showed good dispersion of the coated glass flakes 1a and were superior as cosmetics in terms of color and other properties.

Examples 349 to 406

The coated glass flakes 1a of Examples 59 to 116 were mixed with an ink composition composed of given amounts of colorant, resin, and organic solvent to obtain ink compositions of Examples 349 to 406 which contained the coated glass flakes 1a. These ink compositions showed good dispersion of the coated glass flakes 1a and were superior as ink compositions in terms of color and other properties.

Examples 407 to 464

In Examples 407 to 464, the glass compositions produced in Examples 1 to 58 were used to produce chopped strands usable as a glass filler. Specifically, the glass composition (bulk) was re-melted by an electric furnace, and the melt was formed into pellets under cooling. Next, these pellets were introduced into an production apparatuses as shown in FIG. 4 and FIG. 5 to produce chopped strands having an average fiber diameter of 10 to 20 μm and a length of 3 mm.

The present invention may be embodied in other forms without departing from the spirit or essential characteristics thereof. The embodiments disclosed in this specification are to be considered in all respects as illustrative and not limiting. The scope of the present invention is indicated by the appended claims rather than by the foregoing description, and all changes which come within the meaning and range of equivalency of the claims are intended to be embraced therein.

INDUSTRIAL APPLICABILITY

The glass filler of the present invention can be used in the same applications as conventional glass fillers.

The invention claimed is:

1. A glass filler comprising glass having a composition comprising iron oxide, wherein
for the content of the iron oxide in mass %, the following are satisfied:
$0.005 \leq FeO \leq 0.30$; and
$0.01 \leq T\text{-}Fe_2O_3 < 0.50$, wherein $T\text{-}Fe_2O_3$ represents total iron oxide calculated as $Fe_2O_3$,
for the iron oxide in the composition, $Fe^{2+}/(Fe^{2+}+Fe^{3+})$ is 0.45 or more and 1.00 or less, wherein $Fe^{2+}/(Fe^{2+}+Fe^{3+})$ represents the proportion by mass of $Fe^{2+}$ to total iron;
the composition further comprises the following components, in mass %:
$50 \leq SiO_2 \leq 60$,
$2 \leq B_2O_3 \leq 15$,
$10 \leq Al_2O_3 \leq 20$,
$15 \leq CaO \leq 30$, and
$0 \leq (Li_2O+Na_2O+K_2O) \leq 2$; and
the glass filler is a glass flake.

2. A glass filler comprising glass having a composition comprising iron oxide, wherein
for the content of the iron oxide in mass %, the following are satisfied:
$0.005 \leq FeO \leq 0.30$; and
$0.01 \leq T\text{-}Fe_2O_3 < 0.50$, wherein $T\text{-}Fe_2O_3$ represents total iron oxide calculated as $Fe_2O_3$, for the iron oxide in the composition, $Fe^{2+}/(Fe^{2+}+Fe^{3+})$ is 0.45 or more and 1.00 or less, wherein $Fe^{2+}/(Fe^{2+}+Fe^{3+})$ represents the proportion by mass of $Fe^{2+}$ to total iron;
the composition further comprises the following components, in mass %:
$57 \leq SiO_2 \leq 65$,
$0 \leq B_2O_3 \leq 2$,
$8 \leq Al_2O_3 \leq 15$,
$1 \leq MgO \leq 5$,
$15 \leq CaO \leq 30$, and
$0 \leq (Li_2O+Na_2O+K_2O) \leq 4$; and
the glass filler is a glass flake.

3. A glass filler comprising glass having a composition comprising iron oxide, wherein
for the content of the iron oxide in mass %, the following are satisfied:
$0.005 \leq FeO \leq 0.30$; and
$0.01 \leq T\text{-}Fe_2O_3 < 0.50$, wherein $T\text{-}Fe_2O_3$ represents total iron oxide calculated as $Fe_2O_3$,
for the iron oxide in the composition, $Fe^{2+}/(Fe^{2+}+Fe^{3+})$ is 0.45 or more and 1.00 or less, wherein $Fe^{2+}/(Fe^{2+}+Fe^{3+})$ represents the proportion by mass of $Fe^{2+}$ to total iron;
the composition further comprises the following components, in mass %:
$65 < SiO_2 \leq 70$,
$5 \leq Al_2O_3 \leq 15$,
$1 \leq MgO \leq 10$,
$10 \leq CaO \leq 25$, and
$0 \leq (Li_2O+Na_2O+K_2O) \leq 4$; and
the glass filler is a glass flake.

4. A glass filler comprising glass having a composition comprising iron oxide, wherein
for the content of the iron oxide in mass %, the following are satisfied:
$0.005 \leq FeO \leq 0.30$; and
$0.01 \leq T\text{-}Fe_2O_3 \leq 0.50$, wherein $T\text{-}Fe_2O_3$ represents total iron oxide calculated as $Fe_2O_3$,
for the iron oxide in the composition, $Fe^{2+}/(Fe^{2+}+Fe^{3+})$ is 0.45 or more and 1.00 or less, wherein $Fe^{2+}/(Fe^{2+}+Fe^{3+})$ represents the proportion by mass of $Fe^{2+}$ to total iron;
the composition further comprises the following components, in mass %:
$50 \leq SiO_2 \leq 75$,
$0 \leq B_2O_3 \leq 2$,
$15 \leq Al_2O_3 \leq 30$,
$5 \leq MgO \leq 25$, and
$0 \leq (Li_2O+Na_2O+K_2O) \leq 4$; and
the glass filler is a glass flake.

5. The glass filler according to claim 2, wherein a visible transmittance, as calculated for a thickness of 15 μm of the glass filler, is 87% or more.

6. The glass filler according to claim 2, wherein a light transmittance $T_{750nm}$ at a wavelength of 750 nm, as calculated for a thickness of 1 mm of the glass filler, is 71 to 91%.

7. The glass filler according to claim 2, wherein a light transmittance $T_{350nm}$ at a wavelength of 350 nm, as calculated for a thickness of 1 mm of the glass filler, is 5 to 84%.

8. A coated glass filler comprising the glass filler according to claim 2 and a coating formed on a surface of the glass filler, wherein
the coating contains a metal or a metal oxide as a main component.

9. A resin composition comprising the glass filler according to claim 2 and a matrix resin.

10. A paint comprising the glass filler according to claim 2 and at least one selected from the group consisting of (a) a matrix resin and (b) at least one component selected from the group consisting of a thermosetting resin, a thermoplastic resin, and a curing agent.

11. An ink composition comprising the glass filler according to claim 6 and a vehicle in which is dispersed at least one selected from the group consisting of a pigment and a dye.

12. A cosmetic comprising the glass filler according to claim 2 and a cosmetic additive.

13. A method for producing the glass filler according to claim 2,
the method comprising controlling glass raw materials and/or an atmosphere where the glass filler is formed, thereby controlling, for the iron oxide in the composition of glass, the content of FeO, the content of $T\text{-}Fe_2O_3$, and $Fe^{2+}/(Fe^{2+}+Fe^{3+})$ representing the proportion by mass of $Fe^{2+}$ to total iron to obtain the glass filler having a desired color.

14. A resin composition comprising the coated glass filler according to claim 8 and a matrix resin.

15. A paint comprising the coated glass filler according to claim 8 and at least one selected from the group consisting of (a) a matrix resin and (b) at least one component selected from the group consisting of a thermosetting resin, a thermoplastic resin, and a curing agent.

16. An ink composition comprising the coated glass filler according to claim 8 and a vehicle in which is dispersed at least one selected from the group consisting of a pigment and a dye.

17. A cosmetic comprising the coated glass filler according to claim 8 and a cosmetic additive.

18. A method for producing the coated glass filler according to claim 8,
the method comprising controlling glass raw materials and/or an atmosphere where the glass filler is formed, thereby controlling, for the iron oxide in the composition of glass, the content of FeO, the content of $T\text{-}Fe_2O_3$, and $Fe^{2+}/(Fe^{2+}+Fe^{3+})$ representing the proportion by mass of $Fe^{2+}$ to total iron to obtain the glass filler having a desired color.

* * * * *